(12) United States Patent
Spetz-Holmgren et al.

(10) Patent No.: US 6,506,596 B2
(45) Date of Patent: Jan. 14, 2003

(54) METHOD OF DNA TRANSFER

(76) Inventors: Anna-Lena Spetz-Holmgren, Snäckvägen 14, SE-167 53 Bromma (SE); Lars Holmgren, Snäckvägen 14, SE-167 53 Bromma (SE); Jan Andersson, c/o Huddinge Sjukhus, Dept. for Infectious Diseases, SE-141 86 Huddinge (SE); Judah Folkman, Children's Hospital, Dept. of Surgery, Boston, MA (US) 02101

( * ) Notice: Subject to any disclaimer, the term of this patent is extended or adjusted under 35 U.S.C. 154(b) by 0 days.

(21) Appl. No.: 09/842,073

(22) Filed: Apr. 26, 2001

(65) Prior Publication Data

US 2002/0031521 A1 Mar. 14, 2002

Related U.S. Application Data

(60) Provisional application No. 60/208,326, filed on Jun. 1, 2000.

(51) Int. Cl.[7] .............................. C12N 5/00; C12Q 1/68; G01N 33/53
(52) U.S. Cl. ........................... 435/325; 435/6; 435/7.24
(58) Field of Search ........................... 435/6, 7.24, 325

(56) References Cited

FOREIGN PATENT DOCUMENTS

| WO | 9942564 | 8/1999 |
|---|---|---|
| WO | 9958645 | 11/1999 |
| WO | 0073415 A2 | 12/2000 |

OTHER PUBLICATIONS

Spetz et al., The Journal of Immunology, (1999), vol. 163, pp. 736–742.

Holmgren et al., Blood, vol. 93, No. 11 (Jun. 1, 1999, pp. 3956–3963.

Bergsmedh et al., PNAS, vol. 98, No. 11, (May 22, 2001), pp. 6407–6411.

de la Taille et al., Cancer Research, vol. 59, (1999), pp. 5461–5463.

Savill et al., Immunology Today, vol. 14, No. 3, (1993). pp. 131–136.

*Primary Examiner*—Hankyel T. Park
(74) *Attorney, Agent, or Firm*—Birch, Stewart, Kolasch & Birch, LLP

(57) ABSTRACT

The present invention relates to a method of of transferring genomic DNA from apoptotic bodies to engulfing cells, wherein DNA is transferred from a donor cell to a recipient cell. More specifically the method includes providing somatic donor cells comprising desired DNA; generating apoptotic bodies of said donor cells; incubation of the apoptotic bodies with engulfing recipient cells under biological conditions allowing uptake of DNA from the apoptotic bodies by said recipient cells; and optionally selecting recipient cells which have integrated DNA from the apoptotic bodies. The present method is useful in various pharmaceutical applications, such as in vaccine preparations and gene identification procedures. Further, the present invention also relates to a method of preventing and/or treating a clinical condition in a patient, which comprises isolating cells comprising genomic DNA; generating apoptotic bodies of said isolated cells; incubation of said apoptotic bodies with engulfing recipient cells under biological conditions allowing uptake of DNA from the apoptotic bodies, optionally, selecting cells containing DNA originating from the isolated cells; and administering cells in a pharmaceutically acceptable carrier to the patient, thus enabling a protective and/or therapeutic reaction against the clinical condition.

28 Claims, 21 Drawing Sheets

Vaccination with apoptotic MuLV-HIV infected syngeneic cells

A

B

Anti-p24 serum ELISA

A

Apoptotic MuLV-HIV        Apoptotic control

B

METHOD OF DNA TRANSFER

This application claims priority on provisional Application No. 60/208,326 filed on Jun. 1, 2000, the entire contents of which are hereby incorporated by reference.

TECHNICAL FIELD

The present invention relates to a method of DNA transfer between cells, resulting in protein expression in the recipient cell. Further, the invention also relates to the use of such DNA transfer in a method of treating and/or preventing clinical conditions.

BACKGROUND

Cell death in multicellular organisms is known to follow one of two pathways, namely necrosis or apoptosis. Necrosis is known to be the pathological form of cell death, and usually the result of physical injury, while apoptosis is genetically controlled and the deliberate cellular response to specific environmental and developmental stimuli. Apoptotic cell death is characterized by plasma blebbing, cell volume loss, nuclear condensation, DNA fragmentation and the generation of membrane enclosed apoptotic bodies. These apoptotic bodies are rapidly removed by phagocytosis of neighboring cells. The recognition of apoptotic bodies by macrophages, dendritic or neighboring cells is mediated by several different pathways. Surface receptors such as the vitronectin receptor (av$\beta$3) and thrombospondin receptor (CD36) located on the macrophages may recognize apoptotic cells via the binding of thrombospondin (Savill J, Fadok V, Henson P, Haslett C: Phagocyte recognition of cells undergoing apoptosis. *Immunol Today* 14:131, 1993). Translocation of phosphatidylserine from the inner to outer side of the cell membrane serves as recognition signals for phagocytosis. Not only macrophages are capable of phagocytosing apoptotic bodies. Injection of apoptotic liver cells in the portal vein in the mouse liver results in uptake of apoptotic bodies in the liver endothelial cells. In vitro, apoptotic macrophages are rapidly phagocytosed by human fibroblast cells within 1 h.

Since it has now been shown that apoptosis plays an essential role not only in the embryonic development, as previously thought, but also occurs normally in healthy adult individuals, the latter has attracted a great interest during the past decades. More specifically, it has been shown that apoptosis is involved in a large number of wide spread diseases, such as infections, cancer and autoimmune diseases.

Thus, the control of cell number in multicellular organisms depends on the fine balance between cell proliferation and cell death. As mentioned above, cell death by apoptosis plays a key role in the elimination of cells during embryonic development as well as in adults. It is for example involved in the negative selection of neural cells, removing redundant cells during organ formation. In adults, apoptosis plays an important role in the maintenance of tissue homeostasis. Apoptosis is also of importance in tumor development. It may serve as an anticancer mechanism by restricting the expansion of cells with unleashed proliferative potential.

Thus, since too much or too little apoptosis is believed to play a role in the most common diseases, research is directed to find new forms of treatment based on a more thorough understanding thereof. A much desired goal would be to understand the mechanism behind as well as consequenses of apoptosis well enough to enable control of such disorders.

SUMMARY OF THE PRESENT INVENTION

Accordingly, one object of the present invention is to provide a method of DNA transfer by the uptake and reuse of apoptotic bodies by somatic cells. A specific object is to provide a method of preventing and/or treating a clinical condition in a patient, which in an advantageous embodiment enables use of an antigen derived from the said patient as a therapeutical vaccine. Accordingly, the present invention also encompasses a process for the manufacture of a pharmaceutical composition, which composition can be specifically designed for each patient to be treated. Thus, yet another object of the present invention is such a personalized, therapeutic vaccine. The different objects are achieved as detailed in the appended claims.

DEFINITIONS

Figure 1:
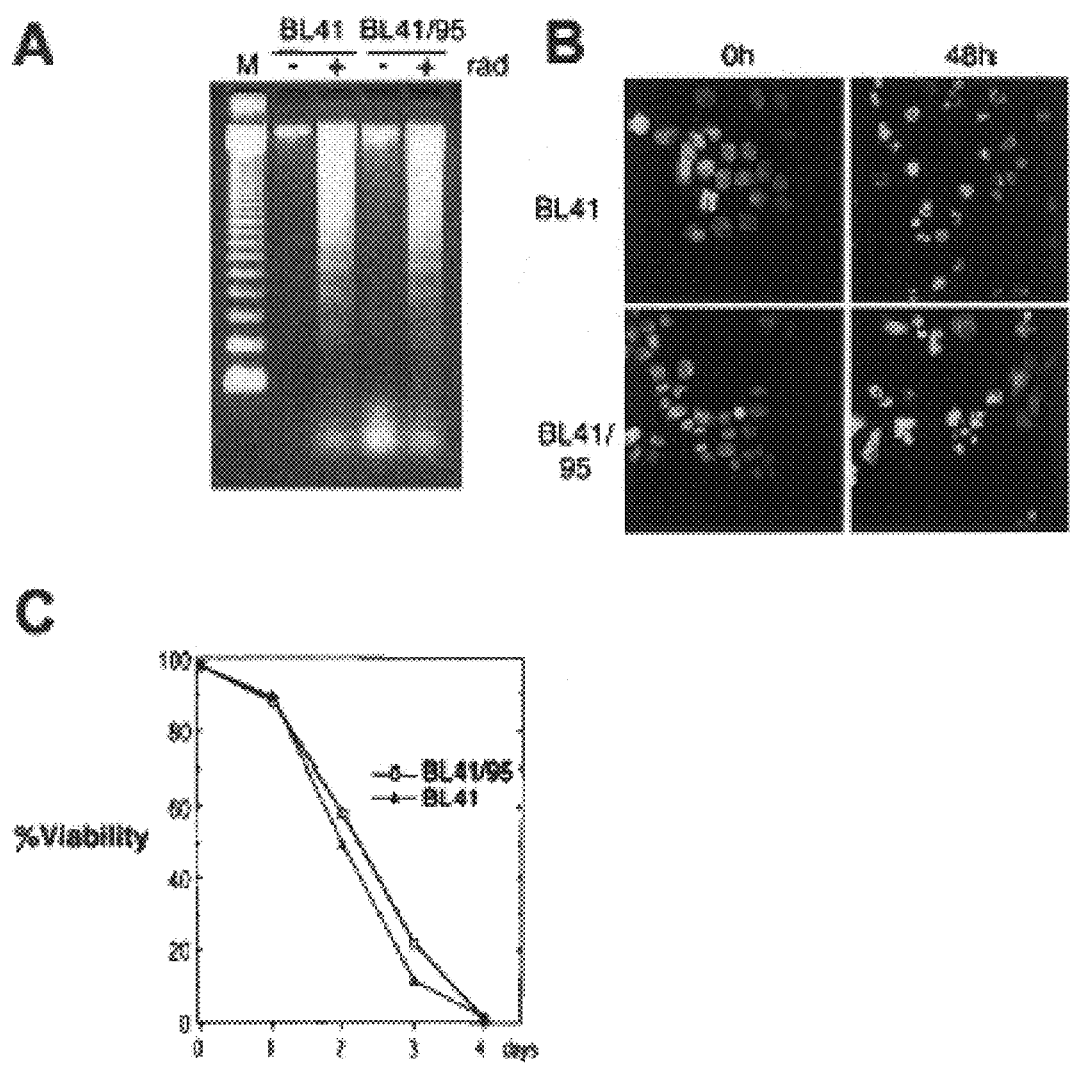
FIGS. 1A–C illustrates the induction of apoptosis in BL41 and BL41/B95 cells.

In the present invention, the term "genomic DNA" means any DNA present in a cell, either naturally or after introduction by genetic engineering techniques. Thus, it may be a complete gene, a regulatory DNA sequence etc.

The term "engulfment" comprises any uptake of DNA from apoptotic bodies, such as phagocytosis, endocytosis and pinocytosis comprising processes where small or large fragments of DNA are internalized into the engulfing cells genome without any substantial damage thereof The term "apoptotic bodies" includes as used in the present specification any cell expressing a native or foreign antigen undergoing apoptosis due to any condition, including those which usually are associated with causing necrosis. Thus, an apoptotic body is identified based on its characteristics described i.e. in the section "Background" above rather than by any method used leading to cell death. Accordingly, it is to be understood that included in the term "apoptotic bodies" as used herein is any apoptotic fragments or apoptotic cell material, bodies, blebs, vesicles, particles etc.

As used herein, a "biological sample" is a sample of biological tissue or fluid that, in a healthy and/or pathological state, contains cells comprising genomic DNA. Such samples include, but are not limited to, peripheral blood, liver cells, bone marrow, resected tumor cells or cells cultured in vitro.

DETAILED DESCRIPTION OF THE INVENTION

The present invention relates to a method of transferring genomic DNA from apoptotic bodies to engulfing cells, wherein DNA is transferred from donor cells to recipient cells, which method includes (a) providing somatic donor cells comprising genomic DNA;

(b) generation of apoptotic bodies of said donor cells;

(c) incubation of the apoptotic bodies with engulfing recipient cells under biological conditions allowing uptake of DNA from the apoptotic bodies by said recipient cells: god, optionally, (d) selecting recipient cells which have integrated DNA from the apoptotic bodies. Preferably, said recipient cells are capable of expression of protein product(s) encoded by the transferred DNA.

Step (d) is included or excluded depending on the future use of the hybrid cells produced from the present uptake of DNA from apoptotic bodies. For example, in the application of the present method in schemes for the treatment of clinical conditions in patients as discussed below, a high degree of specificity of the population of hybrid cells may be desired or even required, while for use for various research application, such as the gene identification described below, in an alternative embodiment step (d) may then be excluded. However, the skilled in this field who works the present invention will easily determine whether or not to use a selection step. Also, suitable selection pressures are applied depending on the prevailing conditions, as discussed in more detail below. The present method may be performed in vitro or in vivo for various applications, as will be disclosed in more detail below. The DNA to be transferred to the recipient cell may be any coding or non-coding sequence. For example, the encoded gene product(s) expressed by the recipient cells are proteins or peptides, including bound carbohydrates, lipids etc. Alternatively, the DNA to be transferred is a regulatory element useful to control expression.

Thus, a general objective of the present invention is to provide a method of using apoptotic cells, blebs, bodies or fragments to transfer DNA to antigen presenting cells which will synthezise, process and present said proteins (encoded by the transferred DNA) on their surface for stimulation or tolerization of T cells.

In one aspect the present invention relates to the transfer of DNA by use of apoptotic bodies and thereby direct antigen to the MHC class I antigen presenting pathway. An advantage of transferring DNA by the use of apoptotic bodies is that poorly defined or undefined antigens can be routed to the appropriate antigen processing compartment of the antigen presenting cell to generate antigen-specific T cell responses.

Even though DNA transfer from bacteria to somatic cells have been shown, the present invention shows for the first time that genomic DNA can be transferred from somatic cells to engulfing, e.g. phagocytosing, cells capable of expression thereof in vivo or in vitro. An especially advantageous feature of the invention is that much larger DNA fragments than what was possible with conventional vectors, such as viral vectors, can now be transferred. Thus, in a specific embodiment, the method according to the invention relates to the transfer of a whole chromosome from a donor tumor cell to an engulfing cell, as is evidenced below in example 3. An advantage with the present invention is that it also provides a stable propagation, which is an important feature in gene transfer.

Further, even though WO 99/42564 discloses apoptotic cell-mediated antigen presentation to dendritic cells, it fails to define the DNA transfer shown in the present specification. Thus, WO 99/42564 relates to providing antigen presenting cells, while the present inventors for the first time have shown DNA transfer using apoptotic bodies as a carrier of DNA from donor to recipient cells. Accordingly, the present invention enables a broad field of applications, which may be specifically adapted for various situations.

Donor cells are obtained from a biological sample from any suitable source and prepared into a form suitable for step (b). They may for example be transfected, transduced or transformed to contain the gene to be transferred to recipient cells prior to induction of apoptosis. The donor cells diluted in a suitable solvent (such as culture medium (for example RPMI) or physiologic salt solution (for example phosphate buffered saline PBS)) and/or pretreated in a way easily determined by the skilled in this field, depending e.g. on the cell types used and the aim of the procedure. In general, apoptosis can be induced by physical, for example, heat, Fas, UV-B and gamma radiation, and chemical, for example ethanol or etoposide, treatments. Apoptosis can also be induced by cytokines, virus infection or Fas-Fas ligand interactions. (See, e.g., Mincheff, M., et al., Blood Transfusion and Immunomodulation: A Possible Mechanism, Vox Sang, 65:18–24, 1993; Thompson, C. D., Apoptosis in the Pathogenesis and Treatment of Disease, Science, 267:1456–1462, 1995) In the most preferred embodiment, the present donor cells are subject to radiation. Alternatively, serum depriviation, e.g. as shown in the present examples, is used.

The extent of apoptosis generated may be measured by any one of a variety of techniques, for example, by determination of annexin V and propidium iodide uptake by flow cytometry. Determination of apoptosis by flow cytometry is well within the ability of one with ordinary skill in the art.

Further, there are also a number of biochemical assays that can be used to detect apoptosis, such as "laddering" of the cellular DNA. When testing compounds for the ability to induce apoptosis, cell death (not cytostasis) is an end point of compound application to the cell. A classic signature of apoptosis is the cleavage of nuclear DNA into nucleosomal subunits. On gels, this gives rise to the appearance of a ladder as nucleosomal units are sequentially cleaved from the DNA. Observation of a classic DNA ladder is indicative of apoptosis. For example, cells are lysed and the high molecular DNA is removed by centrifugation. The aqueous phase is treated with proteinase K to digest proteins. After a phenol/chloroform extraction, the DNA is precipitated with salt and ethanol. The pellet is dissolved in deionized water and treated with 500 mu.g/ml RNase A. The DNA is run on a 2% agarose minigel. Observation for a classic DNA ladders is made. A gel photograph can be taken. Cell death is verified by the demonstration of DNA fragmentation as represented by the ladder configurations on the gel. (See Gavrieli, Y., et al. (1992) J. Cell Biol. 119:493). There are also a variety of other assays available for apoptosis such as "TUNEL" assays (see White, E., et al. (1984) J. Virol. 52:410). See also Example 7, herein, for a demonstration of the determination of apoptosis.

When included, the selection according to step (d) is achieved by any suitable, conventional method known to those skilled in the art, such as fluorescence activated cell sorting (FACS), panning, techniques using monoclonal antibodies, magnetic bead separation etc.

In a specific embodiment, apoptotic bodies are contacted with immature cells, such as dendritic cells, capable of engulfing apoptotic bodies, followed by addition of a suitable signal that promotes maturation of said dendritic cells into efficient antigen presenting cells. This embodiment may e.g. comprise necrotic cells and cytokines as maturation signals, since it is speculated by the present inventors that both apoptosis and necrosis may be essential for an efficient DNA transfer according to the invention. (For a reference to details regarding this embodiment, see WO 99/42564 in the name of Albert et at).

As regards dendritic cells, example 4 below shows that such cells are capable of expressing an antigen after uptake of apoptotic cells from HIV-1 infected lymphoma T cell lines and are capable of inducing T cell responses in vitro. Thus, the present invention provides evidence that dendritic cells are functional carriers of virus capable of keeping the virus alive.

In an alternative embodiment, the present invention is restricted to non-proliferative cells, e.g. dendritic cells, which will not propagate transferred DNA. Biological conditions allowing engulfment according to the present invention are also well known to the skilled and may e.g. be as given below in the experimental section. More specifically, as regards dendritic cells, the generation thereof can be isolation by methods well known to those skilled in the art. Human dendritic cells are used from an appropriate tissue source, preferably skin, blood or bone marrow. The immature dendritic cells with capacity to engulf apoptotic bodies used in this invention were derived from precursors present in blood as peripheral blood mononuclear cells. When the precursors are cultured in the presence of GM-CSF and IL-4 (Romani et al 1994, J.Exp.Med. 180, 83, Sallusto et al 1994, J.Exp.Med. 179, 1109, Lore et al 1998, J. Immunol. Methods 214, 97), the non-proliferating precursors give rise to immature dendritic cells. The immature dendritic cells are cocultured with the apoptotic cells to allow transfer of DNA. To fully become mature dendritic cells with capacity to present antigen to T cells the immature dendritic cells require a maturation factor. The maturation factor can be added to the medium and may be selected from monocyte conditioned medium and/or factors including TNF-alpha, IL-6, IFN-alpha and IL-1b or material from necrotic cells. In the present invention it is preferably derived from the apoptotic cells added to the coculture which undergo secondary necrosis. As regards further examples of engulfing cells, for details regarding fibroblasts and macrophages, see below, section "Experimental".

In an advantageous embodiment of the present method, the donor cell is a cell that contain genomic DNA with various advantageous pharmaceutical uses thereof and may e.g. be a lymphoid cell, a fibroblast, a macrophage, tumor cells, such as fibrosarcoma, chronic or acute myeloid leukemia, acute lymphatic leukemia, liver cell, bone marrow derived stem cell, liver cell, pancreatic cells etc. However, the donor cells are not restricted to the examples given above. The donor cell may previously been subject to methods of genetic manipulation to internalize non-native DNA, such as genes, various regulatory elements etc. The nature of the recipient cell is chosen depending on the intended purpose, while the only limiting criterion is that it must be capable of engulfing DNA from apoptotic bodies. Thus, in one embodiment, it may be any antigen presenting cell or a phagocytic cell, which for example may be selected from the group consisting of macrophages, dendritic cells, endothelial cells and fibroblasts. Engulfing cells may possess the capability of engulfment in their native form or be induced to engulf DNA by methods well known in this field.

One specific embodiment of the present invention relates to the use of tumor cells as donor cells, Tumor formation involves the accumulation of a series of genetic alterations that are required for malignant growth. In most malignancies, genetic changes can be observed at the chromosomal level as losses or gains of whole or large portions of chromosomes. The present invention provides for the first time evidence that tumor-DNA may be horizontally transferred by the uptake of apoptotic bodies. As shown in example 3 below, phagocytosis of apoptotic bodies derived from H-ras$^{V12}$ and human c-myc transfected rat fibroblasts resulted in the loss of contact inhibition in vitro and a tumorigenic phenotype in vivo. Fluorescence in situ hybridization analysis revealed the presence of rat chromosomes or of rat and mouse fusion chromosomes in the nuclei of the recipient murine cells. The transferred DNA was propagated provided that the transferred DNA conferred a selective advantage to the cell and that the phagocytotic host cell was p53-negative. Accordingly, this embodiment of the present method includes providing tumor cells comprising genomic DNA which has been rendered capable of conferring a selective advantage to the cell in accordance to methods well known in this field. The results presented in example 3 below suggest that lateral transfer of DNA between eukaryotic cells may result in aneuploidy and the accumulation of genetic changes that are necessary for tumor formation.

The present method is advantageously used in cases where the recipient cell is an antigen presenting cell that lack receptors for the protein, such as the proteinous coat of a virus. This is an especially advantageous feature in the context of HIV-1. Antigen presenting cells, such as dendritic cells, can engulf HIV-DNA containing apoptotic cells, bodies, blebs or fragments independently of free virus or expression of HIV-1 specific receptors. The viral DNA present in for example latently infected cells can, hence, be taken up by dendritic cells. The transferred DNA is after engulfment used by the denritic cells and the newly formed protein(s) are accessible for the MHC processing and presentation pathways. The processed antigens synthesised following DNA transfer are presented on the cell surface of the antigen presenting cells leading to stimulation or tolerization of T cells.

In a second aspect, the present invention relates to the use of the present method to formulate a pharmaceutical composition, e.g. a vaccine composition or a composition for inducing tolerance in a patient, as will be disclosed in detail below in the context of treatment methods.

Accordingly, in general, the invention relates to a process for the manufacture of a pharmaceutical composition comprising the steps of (a) providing first cells comprising desired genomic DNA, (b) generating apoptotic bodies of said first cells;

(c) incubation of the apoptotic bodies with second cells under biological conditions allowing uptake of DNA from the apoptotic bodies by said second recipient cells;

(d) an optional step of selecting recipient cells containing DNA transferred from the first cells and capable of expression of protein product(s) encoded by said transferred DNA; and (e) formulating a pharmaceutical composition, such as a vaccine, from the expressed protein product(s) and a pharmaceutically acceptable carrier.

In one illustrating embodiment, the present method is used in the context of tumor treatment, such as acute myelotic leukemia (AML). Current treatment is performed by minitransplants, wherein a patient is given peripheral blood cells originating from an MHC compatible donor. The purpose of such treatment is for the administered T cells to kill tumor cells in the patient. However, these methods have not shown to be sufficiently efficient for a practical use. Thus, the present invention now enables an improvement of T cell function by activation thereof using DNA from apoptotic bodies. There are several optional useful methods, such as 1) incubation of donor cells with apoptotic bodies before the administration thereof to the patient; 2) culture of dendritic cells from the donor, which are allowed to engulf apoptotic bodies and subsequently are administered to the patient with the other blood cells; and 3) in vitro use of dendritic cells having engulfed apoptotic bodies to stimulate T cells before administration thereof to the patient. The basic principles for such treatment schemes are discussed in the above mentioned WO 99/42564 in the name of Albert et al, to which reference is made for flier details. However, it is again noted that Albert et al have not disclosed transfer of DNA by apoptotic bodies.

The pharmaceutical composition according to the invention may alternatively be formulated by the steps above, but excluding also step (c), in which case the final composition will comprise apoptotic cells, bodies, blebs or fragments and a pharmaceutically acceptable carrier. Cell samples may be pretreated, e.g. by washing, depending on the source and method of isolation.

In general, the formulation of pharmaceutical compositions is for example described in general in Remington's Pharmaceutical Sciences, Mack Publishing Company, Philadelphia, Pa., $17^{th}$ ed (1985). The steps correspond to what has been discussed above, and the details given above will also apply to this aspect.

In a third aspect, the present invention also provides a way to generate cell lines which have stably incorporated genomic DNA derived from apototic bodies. In one embodiment, this requires that the recipient cell line is deficient or has inactivated the tumor suppresor genes p53 or p21. These genes may be inactivated e.g. by homologous recombination or inactivated by gene transfer of a dominant negative inhibitor thereof, such as the SV40 large T-antigen, adenovirus E1B55k or the human papilloma protein E6. Cells wit transferred DNA may then be selected by using well known resistance to drug selection, other positive selections may be applies such as loss of contact inhibition, tumorigenicity in mice etc. Resulting cell lines are then analyzed for expression of protein encoded by the apoptotic DNA. This may analyzed by presence of DNA, mRNA expression and protein expression by southern, northern or western blot techniques. Accordingly, the present invention relates to the use of the present method for identification of genes involved in pathological or biological processes, e.g. as will be discussed in detail below in the context of the method of treatment, e.g. in the field of functional genomics, wherein new genes and the functions thereof are studied. The invention also encompasses a kit for performing such a method, which comprises means for generating apoptotic bodies from donor cells; a compartment for coincubation of apoptotic bodies with engulfing recipient cells; a compartment for expression of protein products from recipient cell lines and means for identification of expression products. The cell types used to this end will depend on the specific process to be studied, but are usually well know.

Thus, an especially advantageous embodiment is a stable cell ine as discussed above which is useful as a universal donor cell line. Such a cell line can for example have been transfected with HIV gene(s) and will be useful for preventive and/or therapeutic purposes. The gene used for transfection will naturally need to be truncated in a way so as to avoid expression of the virus itself. As a proof-of-principle of this aspect, example 5 below provides evidence of a successful immunisation of mice with syngenic cells.

Further, in a fourth aspect, the present invention relates to a method of preventing and/or treating a clinical condition in a patient, which comprises (a) isolating cells that comprise genomic DNA;

(b) generating apoptotic bodies of said cells;

(c) incubation of the apoptotic bodies so produced with engulfing cells under biological conditions allowing uptake of DNA from the apoptotic bodies by said cells;

(d) optionally selecting cells comprising DNA originating from the cells isolated according to step (a); and (e) administering such cells comprising DNA from the apoptotic bodies in a pharmaceutically acceptable carrier to the patient, thus enabling a protective and/or therapeutic reaction.

In general, the same factors apply here as already discussed above in view of the apoptosis, the possibility of including a step for selection, the nature of isolated donor cells and recipient cells etc. The isolation is performed by standard procedures well known to the skilled in this field depending on the source. In a specific embodiment, the direct source is the patient who is to receive the treatment. Biological samples comprising cells are e.g. blood, such as peripheral blood, liver cells, bone marrow, resected tumor cells etc, depending on the intended treatment. Cell preparations are treated by conventional techniques well known to those of skill in this field, see e.g. the experimental section below. In some cases, purification of cell samples may be needed. However, a great advantage of the present method is its simplicity, and especially in cases where an immunological response is desired, it may even be a technical advantage not to perform any purification, since the response may be induced by impurities, or undefined components, of the sample. The skilled in this field will decide whether or not some separation or purification step should be added for each specific case.

In another embodiment of the present invention apoptotic cells containing DNA to be transferred that will lead to presentation of the encoded protein by dendritic cells are administered to an individual in an amount and in a location so as to prime dendritic cells in vivo.

In one specific embodiment, the present invention relates to a method of treatment as defined above, which however, includes a direct reintroduction of a therapeutically effective amount of generated apoptotic bodies without any incubation with cells in vitro. This embodiment is due to its simplicity very advantageous, but requires however that the apoptotic bodies are actually taken up by the intended recipient cells within the patients body. Such uptake may be performed by any suitable method. It is envisaged that in some cases, a larger amount of apoptotic bodies should be reintroduced in order to allow a sufficient uptake, as compared to the amount of incubated recipient cells otherwise administered. A further requirement is that the apoptotic bodies used are not harmful to the patient to the extent they are not taken up by the intended cells. Using this embodiment, subsequent control tests are recommended whereby the actual engulfment in the patient is controlled to a satisfactorily extent.

In one embodiment, the engulfing cells are antigen presenting cells, in which case the method is used for vaccination against pathogens, e.g. virus, protozoa or bacteria, microbial or tumors. In an advantageous embodiment, the virus is human immune deficiency virus (HIV). In the case of use as a therapeutic vaccine for the treatment of HIV infected patients, the great advantage is that a new dose can be given as often as required due to the HIVs frequent change of conformation. By administering cells that are capable of expressing HIV protein to the patient, a vaccination is provided which is specific to the nature of the virus conformation at that specific time. Thus, the present method does not require any exact knowledge as to the exact structure of the virus, as long as the establishment of its DNA in specific cells have occurred.

However, according to the present invention, when the present method is utilized to provide a therapeutic vaccination, the infected donor cells must be taken from the patient at such an early stage to comprise the virus while the level of the virus must be sufficiently low not to suppress the engulfing cells (see example 4 below.) Accordingly, the vaccine should be prepared either at an early stage of infection, or at a point in time when the patient's virus levels have been down-regulated to a sufficiently low level. Whether or not the virus level is too high for an efficient immunisation can be tested by the skilled in this field by studying the engulfing cells and any suppression thereof. An especially advantageous embodiment of the present invention is accordingly a personalized i.e. a patient specific vaccine composition. In this context, example 5 below provides evidence of a successful vaccination of mice with HIV-1 containing apoptotic bodies, inducing a systemic HIV-1 specific immunity therein.

Highly active anti-retroviral therapy (HAART) has lead to a pronounced decrease in mortality of HIV-1 infected patients in the western societies. Unfortunately, not even thee years of treatment seem to lead to a cure or controlling immunity. Withdrawal of HAART, despite effective viral suppression (<50 viral copies/ml in plasma), leads to a rapid viral rebound in most patients studied so far. Latently infected cells containing HIV-DNA can be detected in lymphoid tissue despite <50 viral copies/ml in plasma in many patients. HIV-1 downregulates MHC class I molecules, hence disturbing antigen presentation. The generation of anti-HIV specific immune responses may hence be facilitated if vaccinations are performed when viral replication is suppressed after antiretroviral therapy. An improved HIV-1 specific immunity generated by a therapeutic vaccine may be able to control viral replication and allow withdrawal of antiretroviral therapy. A vaccine resulting in an immune activation, which mimics that during natural viral infections by the cognate pathogen, would appear to have the highest probability of success by generating broad both humoral and cellular immunity.

As mentioned above, this method may also be used for vaccination against tumor cells. Cancer cells are genomically instable and therefore show a significant degree of heterogenity in the expression of antigens. The advantage with the present method is that it can be used to generate a vaccine that is specific for the repertoire of proteins expressed by the tumor in the individual cancer patient.

In another embodiment, the method is used to induce tolerance in a patient. The phagocytic cells are then e.g. selected from the group consisting of macrophages, dendritic cells, endothelial cells and fibroblasts, in which case the method is used in the context of autoimmune disorders, such as for example rheumatoid arthritis (RA), multiple sclerosis (MS), systemic lupus erythematosus (SLE), diabetes, Crohn's syndrome or ulcerous colitis, or in transplantation procedures in order to induce tolerance against the transplant. In case of transplantation, the sample of donor cells is not taken from the patient but from the organ donor.

In yet another embodiment, the present method is used in the context of gene therapy, e.g. to introduce genes for the purpose of reconstituting absent or malfunctioning genes. For a general review of gene therapy procedures, see e.g. Anderson, *Science* (1992) 256:808–813; Nabel and Felgner (1993) *TIBTECH* 11:211–217; Mitani and Caskey (1993) *TIBTECH* 11:162–166; Mulligan (1993) *Science* 926–932, Dillon (1993) *TIBTECH* 11:167–175; Miller (1992) *Nature* 357:455–460; Van Brunt (1988) *Biotechnology* 6(10): 1149–1154; Vigne (1995) *Restorative Neurology and Neuroscience* 8:35–36; Kremer and Perricaudet (1995) *British Medical Bulletin* 51(1) 31–44; Haddada et al. (1995) in *Current Topics in Microbiology and Immunology* Doerfler and Böhm (eds) Springer-Verlag, Heidelberg Germany; and Yu et al., *Gene Therapy*(1994) 1:13–26. The present invention also encompasses methods of cell therapy, see for a general review of such methods e.g. Nature, vol. 392, Apr. 30, 1998: Fred H. Gage: Cell therapy.

The administration of the cells or apoptotic bodies as a pharmaceutical composition may be any suitable route, intravenous, intramuscular, subcutaneously, intradermal, intraperitoneal, nasal, vaginal. For example, cell amounts in the range of about $10^7$ cells, depending on cell type, clinical condition to be treated etc, are injected in the area of the lymph nodes of the patient within a short period of time after transfer of DNA has been performed. Booster injections may be given after a few weeks, such as 5–10 weeks, also depending on the factors mentioned above. Advantageously, reevaluation of patients is performed at a later stage, such as after 1–2 months. Kugler et al discloses in Nature Medicine, vol. 6, no. 3, March 2000, vaccination with hybrid cells. Even though uptake of apoptotic bodies is distinct from hybrid cell formation, the general aspects of delivery of cells also apply in the present context. (For a general reference to methods of drug delivery, see e.g. Langer, Science 249:1527–1533.) Thus, the present method of treatment will be adapted to the specific clinical condition. The present method does not require any exact knowledge as to the exact structure of the genomic DNA which is transferred and expressed, as long as its presence in specific cells is known or suspected. Hence, there is no need for a vector in the present method. Functional methods for the production of apoptotic bodies thereof may be optimised for each case in order not to ham the DNA. A further advantage of the present method is that it is quick, as there is no need to express the antigens that provoke the immune response outside the body. Instead, the present inventors have surprisingly found that such expression can be achieved in vivo, in the patient. In addition, the present method provides an efficient way of introducing genes at high transfection rates as compared to standard DNA transfection. As an illustration, the present method has a transfection rate of approximately 50% in macrophages and dendritic cells compared to 1–2% with DNA transfection methods. Another advantage is that the present method enables an efficient way of introducing large fragments of genomic DNA.

DETAILED DESCRIPTION OF THE DRAWINGS

FIG. 1 shows the induction of apoptosis in BL41 and BL41/B95 cells. (A) Analysis of DNA fragmentation 48 hours after irradiation with 150 Gy by DNA gel electrophoresis. M, 123-bp DNA-ladder (GIBCO). (B) Apoptotic morphology was examined with Hoechst 33258 DNA staining. (C) Viability of irradiated cells was analyzed by trypan blue exclusion.

Figure 2:
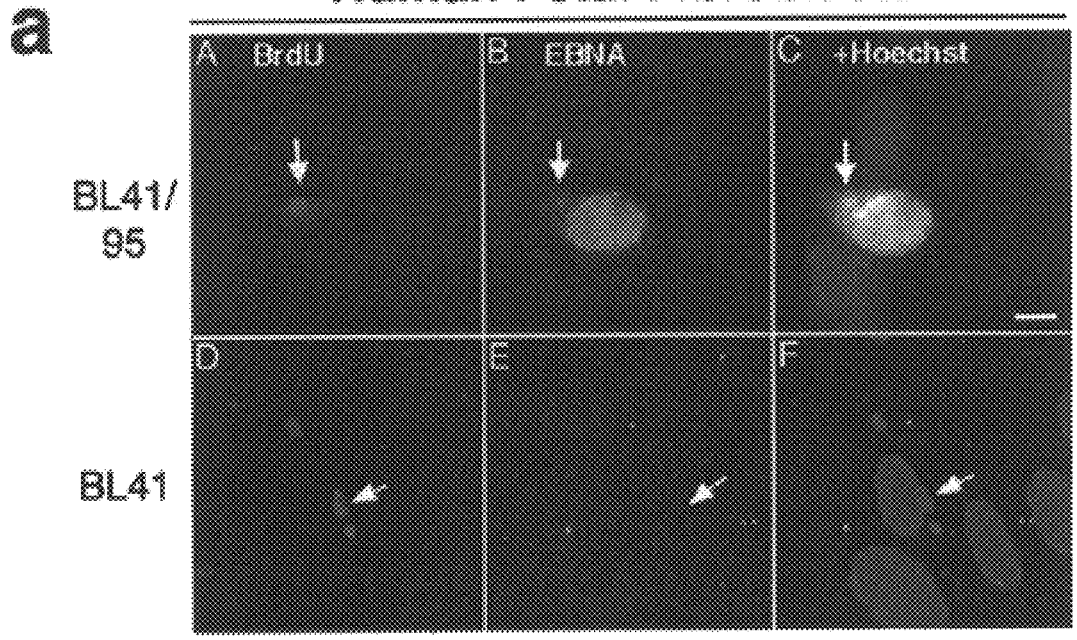
FIG. 2(a) shows the presence of apoptotic bodies in HF cells after 1 week of cocultivation (panels A–F), while 2(b) shows fibroblasts pulsed with BrdU before being cultivated with irradiated BL41/95 cells.
Figure 2:
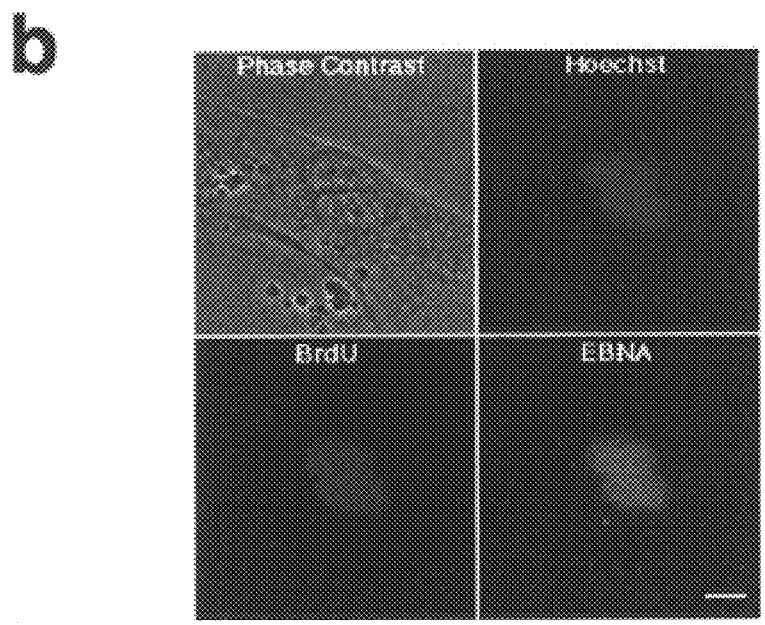

FIG. 2(a) shows presence of apoptotic bodies in HF cells after 1 week of cocultivation. The EBV-positive BL41/95 (A through C) and -negative BL41 (D through F) were labeled for 48 hours with BrdU before irradiation and cultivation with HF cells. DNA from the lymphomas was detected with antibodies against BrdU (A and D). Cells were double-stained with human serum against EBV nuclear antigens (EBNA; B and E). (C) and (F) show Hoechst 33258, anti-EBNA, and anti-BrdU stainings in the same picture. Size bar=5 μm. (b) shows fibroblasts pulsed with BrdU before being cultivated with irradiated BL41/95 cells. Nuclei of fibroblastic origin were detected with antibodies against BrdU. Cells were double-stained with human serum against EBNAs. The picture shows overlapping signals of EBNA, BrdU, and Hoechst 33258 staining in fibroblast nuclei. Size bar=8 μm.

Figure 3:
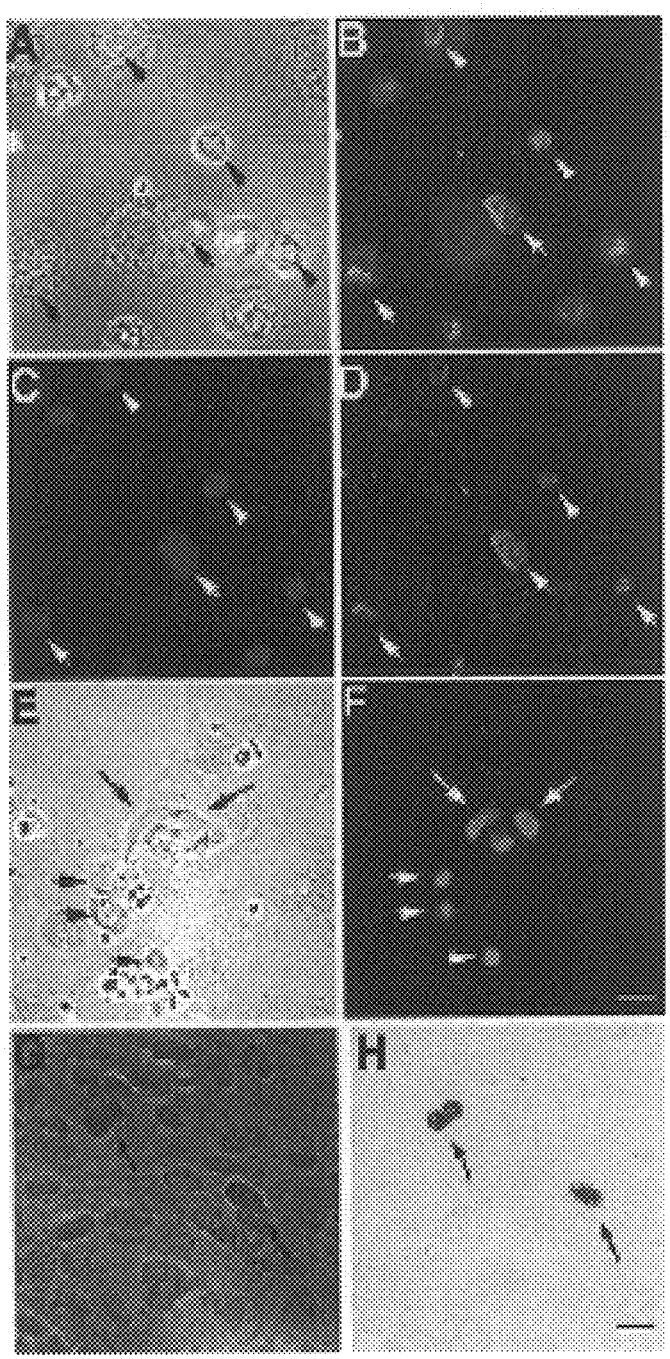
FIGS. 3A–H shows the expression of EBV-specific genes, EBFR1+2 and EBNA1–6, in different cell types after 3 weeks of cultivation with apoptotic bodies from EBV-carrying Namalwa line.

FIG. 3 shows expression of EBV-specific genes, EBER1+2 and EBNA1–6, in different cell types after 3 weeks of cultivation with apoptotic bodies from EBV-carrying Namalwa line. (A) Phase contrast and (B) immunofluorescence staining showing coexpression of macrophage-specific marker CD68 (red) and EDNA (green) in the same cells. (C) shows the location of the macrophage nuclei by Hoechst 33258 DNA staining that overlap with EBNA as shown in (D). Arrows mark the location of the nuclei that are located in the periphery of the cytoplasm of the macrophages. (E) Phase contrast and (F) fluorescence showing EBNA expression in bovine aortic endothelial cells. (G) Phase contrast and (H) bright field view of in situ hybridization analysis of EBER1 and 2 expression in HF cells. Arrows depict positive nuclei. Size bar 20 μm.

Figure 4:
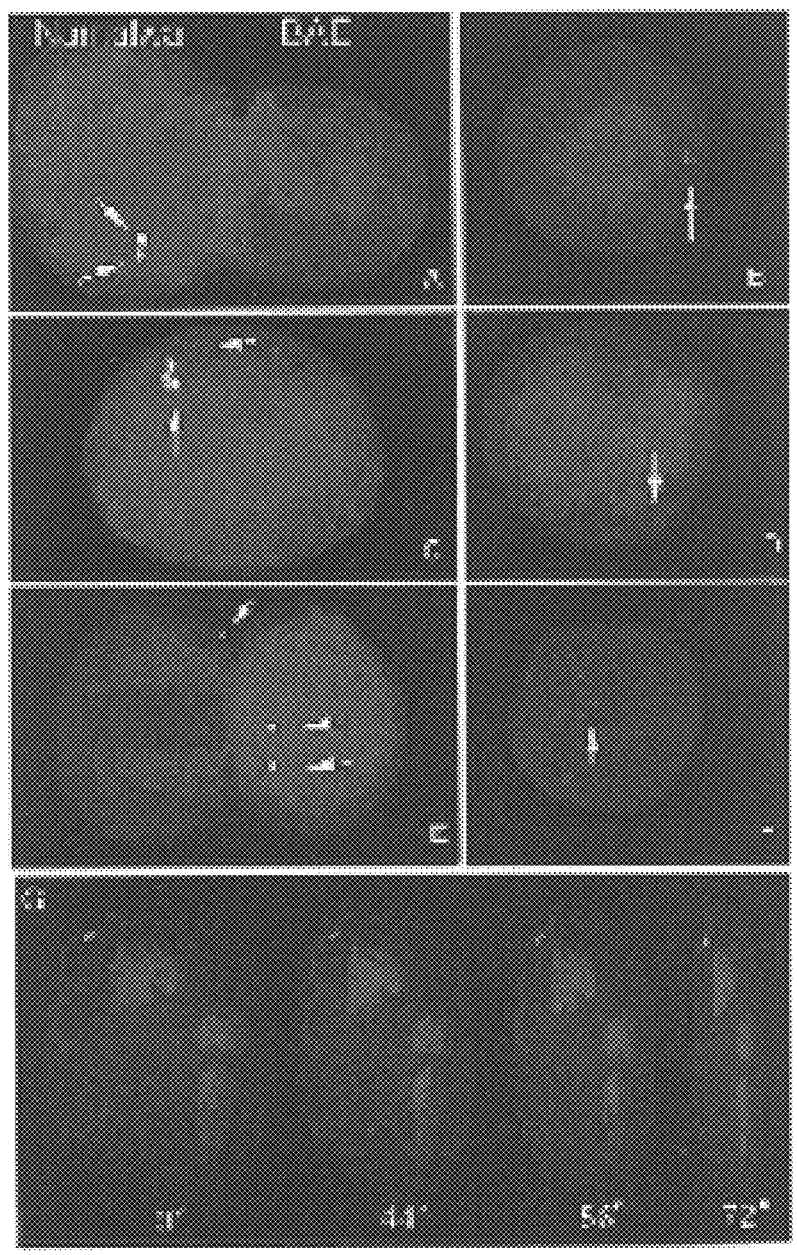
FIG. 4 shows samples hybridized with the BamHI W fragment of EBV, a sequence approximately 3-kb long that is repeated 6 to 10 times in the EBV genome. The nuclei and incoming DNA can be viewed at different angles (0°, 44°, 56°, and 72°) and depths showing that the positive signal was localized within the nuclear cage.

FIG. 4 shows how samples were hybridized with the BamHI W fragment of EBV, a sequence approximately 3-kb long that is repeated 6 to 10 times in the EBV genome. After hybridization, the biotinylated BamHI W probe was detected using the fluorescein-conjugated avidin-biotin amplification system (green signals). Human total genomic DNA was directly labeled with tetra-methyl-rhodamine-dUTP (red signal). The presence of yellow signals indicated overlap of the human and EBV probes. Nuclei were counterstained with the DNA fluorochrome, DAPI (blue). Digital images were captured in gray scale and subsequently pseudo-colored using computer imaging software. (A) Namalwa (left) and BAE nuclei (right) hybridized simultaneously with the EBV BamHI W probe (green) and human genomic DNA probe (red). The Namalwa nucleus shows two distinct signals with the EBV probe and uniform hybridization with the human probe, whereas the bovine nucleus was negative for both probes. (B through E) These figures show four examples from the two-color FISH analysis of the presence of human genomic DNA (red) and EBV-DNA (green) in BAE cells cultured with irradiated Namalwa cells for 1 week Yellow signals indicate overlap of the signals from the EBV BamHI W and the human probes. (F) Simultaneous analysis of presence of EBV-DNA and human DNA in a BAE nucleus after cultivation with the EBV-negative cell line BL41 shows the presence of human DNA but not of EBV DNA in the BAE nucleus. (G) BAE nucleus cultured with irradiated Namalwa cells showing uptake of human DNA (red). A positive signal was analyzed by digital confocal microscopy. Images were sampled in the z-axis and subsequently processed with 3-D rendering software (Openlab) to generate three-dimensional pictures. The nuclei and incoming DNA could be viewed at different angles (0°, 44°, 56°, and 72°) and depths that showed that the positive signal was localized within the nuclear cage.

Figure 5:
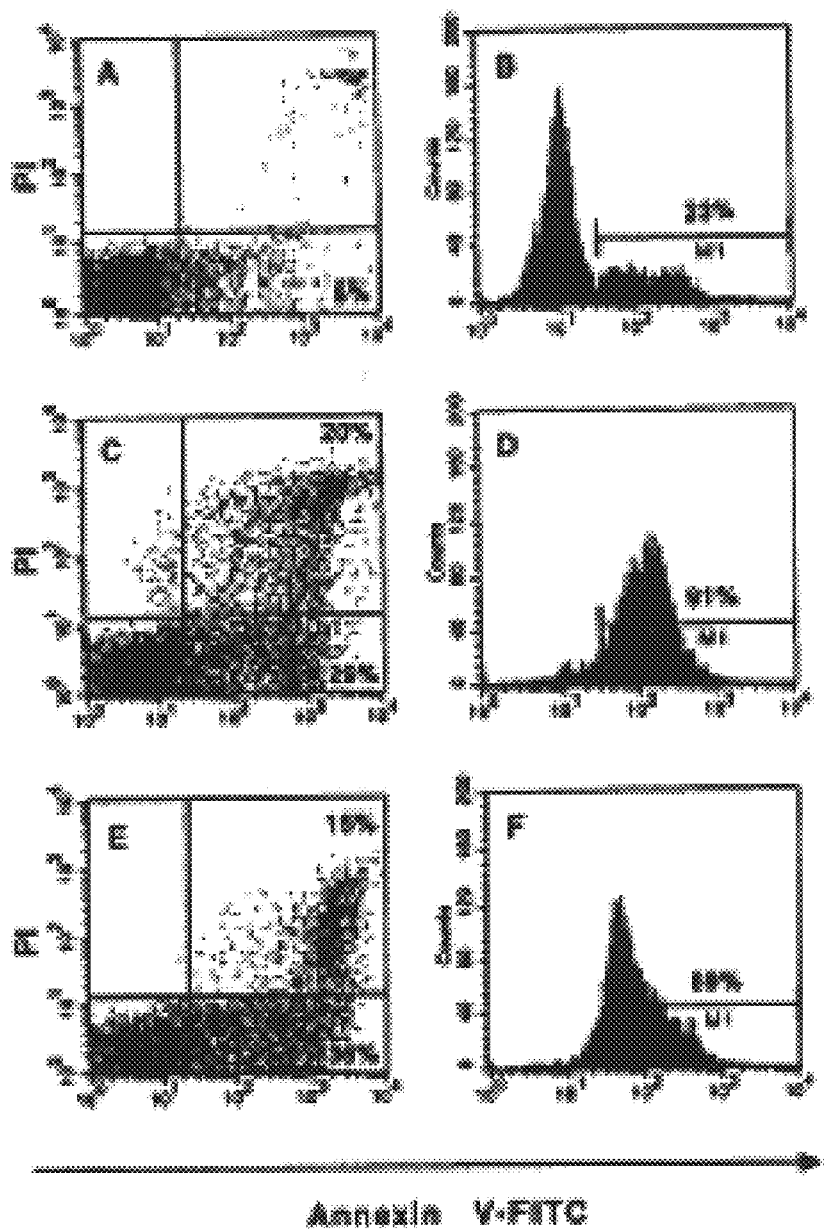
FIG. 5 shows the induction of apoptosis in PBMC and HIV-1-infected T lymphomas. (Results are expressed as $\log_{10}$ of fluorescence.)

FIG. 5 shows the induction of apoptosis in PBMC and HIV-1-infected T lymphomas. PBMC isolated from healthy HIV-1-seronegative blood donors by Ficoll separation (A, C, and E) were stained with annexin V-FITC and PI and analyzed by flow cytometry. No gates were used. HIV-1-infected 8E5/LAV RT⁻ cells (B, D, and F) were stained wit annexin V-FITC and then fixed in 4% paraformaldehyde before analysis by flow cytometry. PBMC or 8E5/LAV RT⁻ cells were untreated in A and B, etoposide treated (16 μg/ml) for 48 h in C and D, or irradiated (150 Gy) 18–24 h before staining in E and F. Results are expressed as $\log_{10}$ of fluorescence, and 10,000 events were collected per sample. One representative experiment of three is shown.

Figure 6:
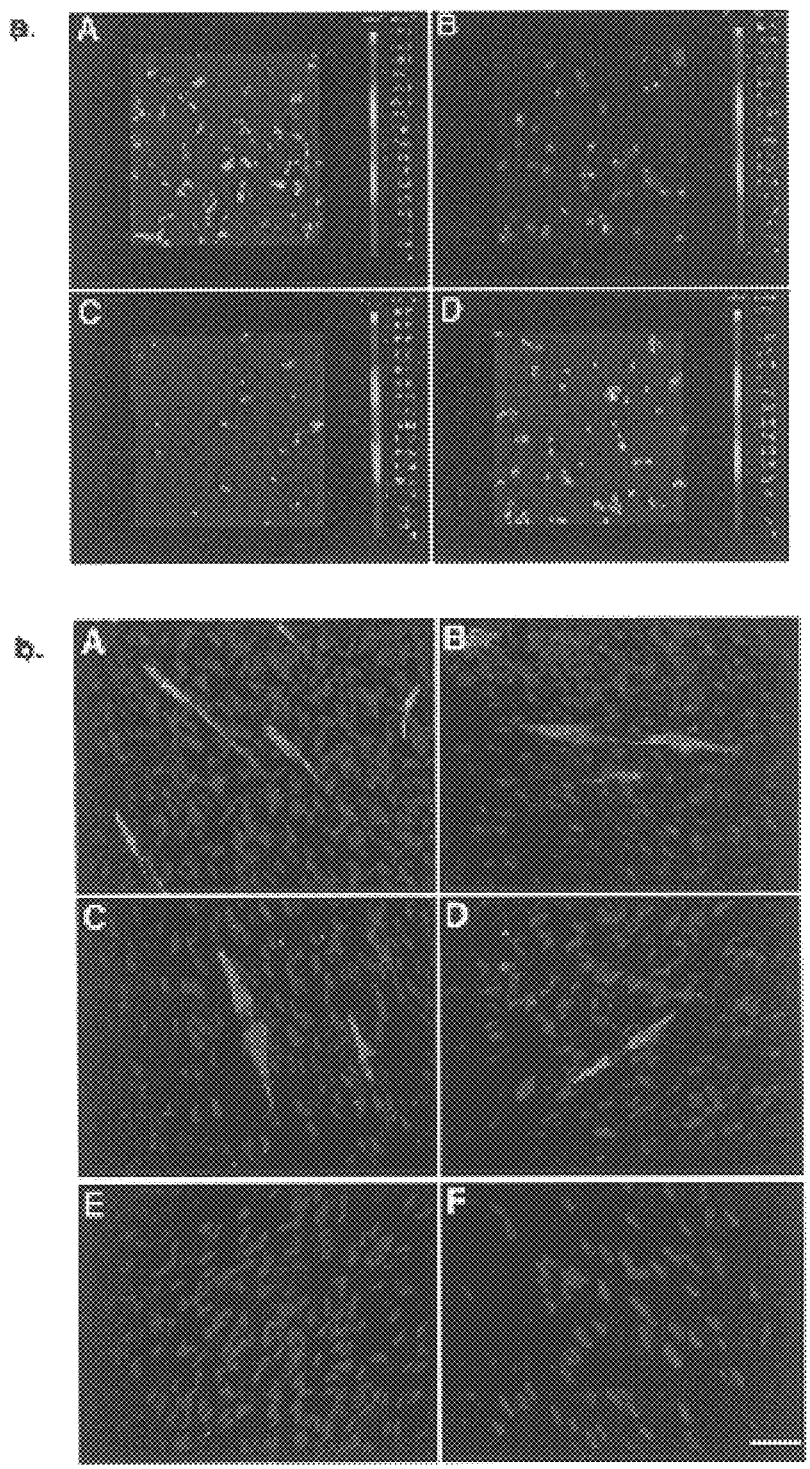
FIG. 6 (a; panels A–D) and (b; panels A–F) show that fibroblasts cocultured with apoptotic HIV-1-infected cells contain HIV-1- DNA and express p24 and gp120.

FIG. 6 shows that fibroblasts cocultured with apoptotic HIV-1-infected cells contain HIV-1-DNA and express p24 and gp120. (a) Fibroblasts were cocultured with apoptotic HIV-1-infected HuT78$_{SF2}$ (A), apoptotic noninfected HuT78 (B), a cell-free primary T cell tropic virus isolate (C), or apoptotic HIV-1-infected cells infected with a defective RT⁻ isolate (8E5/LAV RT⁻ cells; D) (Folks, T. M., Powell, M. Lightfoote, S. Koenig, A. S. Fauci, S. Benn, A. Rabson, D. Daugherty, H. E. Gendelman, M. D. Hoggan, et al. 1986. Biological and biochemical characterization of a cloned Leu-3⁻ cell surviving infection with the acquired immune deficiency syndrome retrovirus. *J. Exp. Med.* 164:280) at ratio of 1:2. After 2 wk of coculture, fibroblast were treated with trypsin and washed in PBS before fixation in Permeafix. HIV-1 gag DNA was detected by FISNA (Patterson, B. K., D. Jiyamapa, E. Mayrand, B. Hoff, R. Abrahamson, and P. M. Garcia. 1996. Detection of HIV-1 DNA in cells and tissue by fluorescent in situ 5'-nuclease assay (FISNA). *Nucleic Acids Res.* 24:3656). Cells containing HIV-1 DNA appear yellow-red-white, with a peak fluorescence intensity of 4095. Uninfected cells appear purple-blue-green, with a peak fluorescence intensity of 2303. Pictures are representative of three experiments. (b) Fibroblasts were cocultured for 2 wk on Lab-Tek chamber slides with apoptotic HIV-1-infected HuT78$_{SF2}$ (A and B), apoptotic 8E5/LAV RT⁻ (Folks, T. M., Powell, M. Lightfoote, S. Koenig, A. S. Fauci, S. Benn, A. Rabson, D. Daugherty, H. E. Gendelman, M. D. Hoggan, et al. 1986. Biological and biochemical characterization of a cloned Leu-3⁻ cell surviving infection with the acquired immune deficiency syndrome retrovirus, *J. Exp. Med.* 164:280) (C and D), or apoptotic noninfected HuT78 cells (E and F) at a ratio of 1:2. Fibroblasts were washed in PBS before they were fixed in paraformaldehyde, permeabilized with saponin, and stained with mAB directed against either p24 (KAL-1, IgG1; A, C, and E) or gp120 (8835, IgG1; B, D, and F) followed by goat anti-mouse Oregon Green-conjugated anti-Ig and Hoechst. One representative experiment of five is shown. The frequency of p24-positive fibroblasts after coculture with apoptotic HuT78$_{SF2}$ or apoptotic 8E5/LAV RT⁻ cells ranged between 0.3–1.7%. One thousand cells per sample were counted. Size bar =20 μm.

Figure 7:
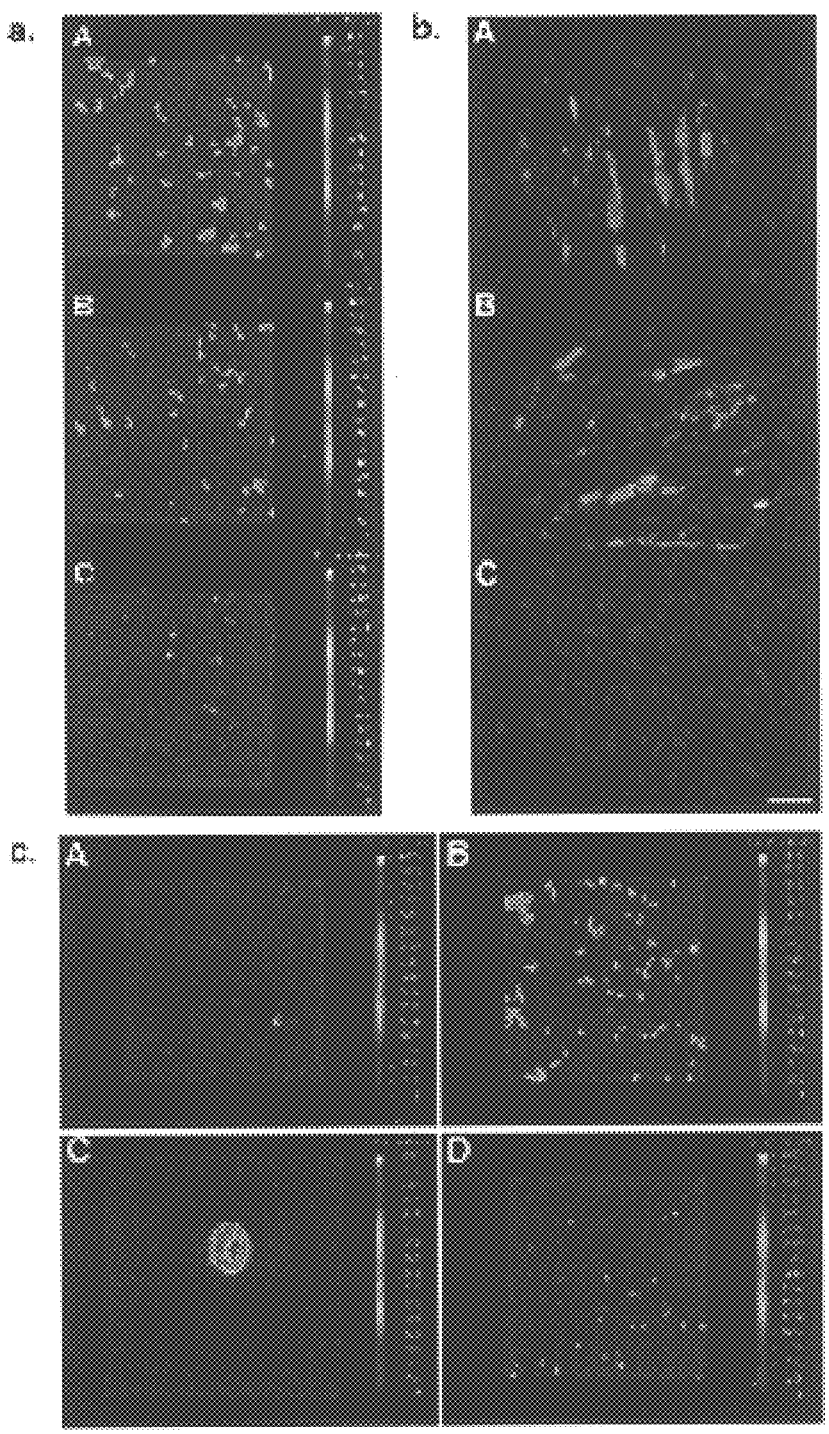
FIG. 7 (a; panels A–C; b: panels A–C; and c: panels A–D) illustrates HIV-1 receptor-independent uptake of HIV-1 DNA by immature dendritic cells.

FIG. 7 shows the HIV-1 receptor-independent uptake of HIV-1 DNA by immature dendritic cells. (a) Immature dendritic cells (3×10⁵/ml) were cocultured with apoptotic 8E5/LAV RT⁻ cells (5×10⁵/ml; A); cell-free Ba-L isolate (B), or apoptotic noninfected HuT78 cells (5×10⁵/ml; C) for 2 wk. The presence of HIV-1 gag DNA was detected FISNA (Patterson, B. K., Jiyampa, E. Mayrand, B. Hoff, R. Abrahamson, and P. M. Garcia. 1996. Detection of HIV-1 DNA in cells and tissue by fluorescent in situ 5'-nuclease assay (FISNA). *Nucleic Acids Res.* 24:3656) using the gag primers SK38/SK39 and the gag probe FTSK19. Cells were examined for the presence of HIV-1 DNA at the single-cell level by a laser confocal microscope. Cells containing HIV-1 DNA appear green-yellow-red, with a peak fluorescence intensity of 3327. Uninfected cells appear purple-blue with a peak fluorescence intensity of 1536. Pictures are representative of two experiments. (b) Functional transfer of HIV-1 DNA by apoptotic PBMC isolated from HIV-1-infected patients. Fibroblasts expressed the HIV-1 Ag p24 after 2 wk of coculture with irradiated (150 Gy), apoptotic PBMC isolated from HIV-1-infected patients (donor 1: HIV RNA, 3,7 log$_{10}$ copies/ml; CD4 count, 50 cells/mm³; A; donor 2: HIV RNA, <2.7 log$_{10}$ copies/ml; CD4 count, 220 cells/mm³; B), while coculture with irradiated apoptotic PBMC from healthy blood donors did not give any staining signal (C). Immunofluorescent stainings were performed with anti-p24 (KAL1 IgG1) followed by Oregon Green-conjugated goat anti-mouse Ig and Hoechst. The frequency of p24 Ag-positive fibroblasts after coculture with apoptotic PBMC isolated from HIV-1-infected patients ranged between 0.6–2.7%. One thousand cells were counted per sample. Size bar=20 μm. (c) Fibroblasts contain HIV-1 DNA after coculture with apoptotic PBMC from HIV-1-infected patients. The presence of gag DNA (yellow-red-white) was analyzed by FISNA (Patterson, B. K., Jiyampa, E. Mayrand, B. Hoff, R. Abrahamson, and P. M. Garcia. 1996. Detection of HIV-1 DNA in cells and tissue by fluorescent in situ 5'-nuclease assay (FISNA). *Nucleic Acids Res.* 24:3656) in fibroblasts cocultured with nonirradiated (A), irradiated (150 Gy) apoptotic PBMC isolated from an HIV-1-infected patient (donor 3; HIV RNA. 6.5 log$_{10}$ copies/ml; CD4 count, 25 cells/mm³; B), irradiated (150 Gy) apoptotic PBMC isolated from another HIV-1-infected patient (higher magnification of donor 4; HIV RNA, 4,2 log$_{10}$ copies/ml; CD4 count, 190 cells/mm³; C), and irradiated apoptotic PBMC from ahealthy HIV-1-seronegative blood donor (D) at a ratio of 1:2. After 2 wk in culture, the presence of HIV-1 gag DNA (yellow-red-white) was detected by FISNA using the gag primers SK38/SK39 and the gag probe FTSK19. Cells containing HIV-1 DNA appear yellow-red-white, with a peak fluorescence intensity of 4095. Uninfected cells appear purple-blue-green, with a peak fluorescence intensity of 2303.

Figure 8:
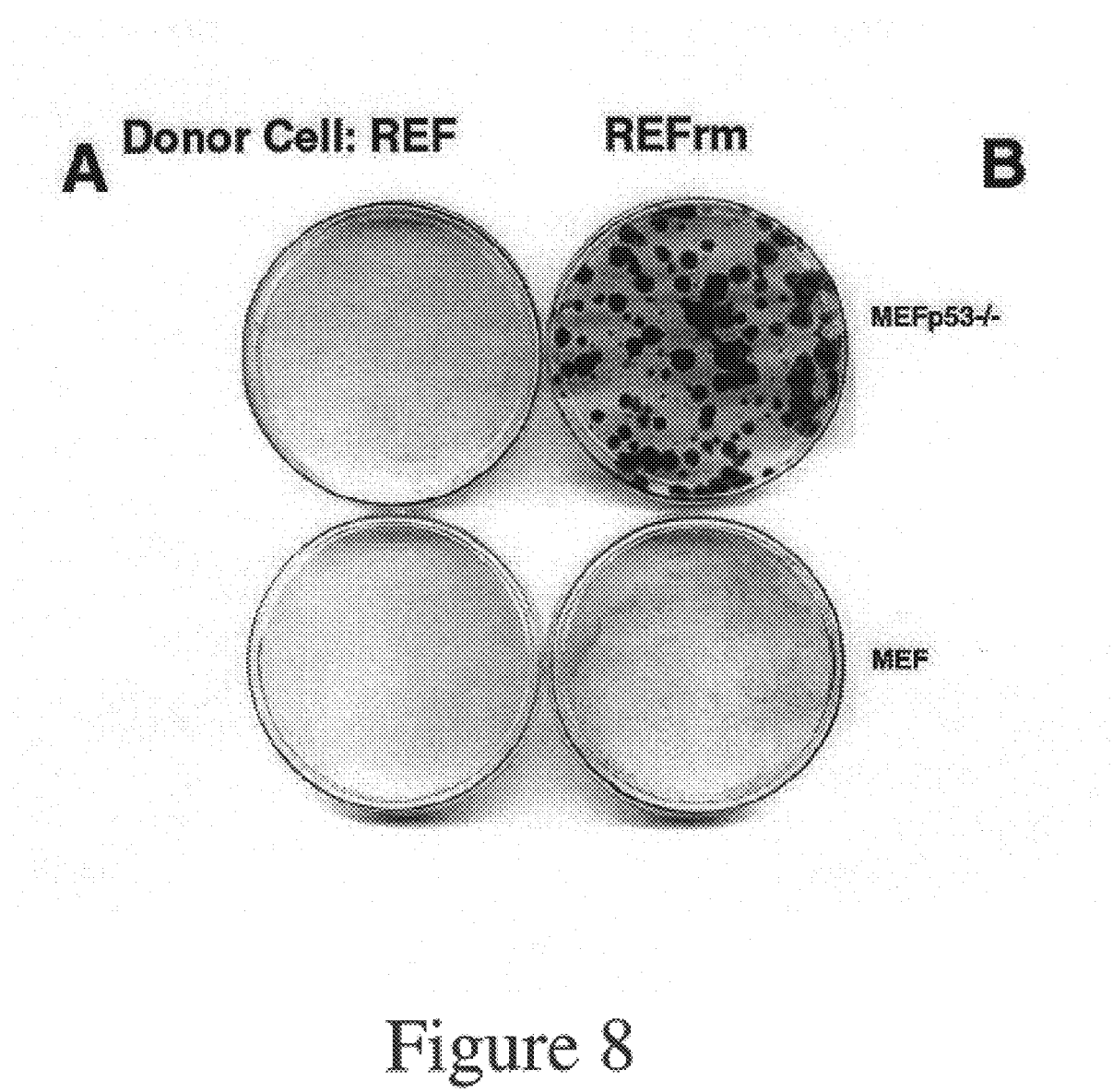
FIG. 8 shows hygromycin resistant colonies after co-cultivation with apoptotic bodies: Left plate, wild type mouse embryonic fibroblasts (MEF), MEF with inactivated p53 cultivated with apoptotic bodies from radiated REF cells lacking the hygromycin resistance gene. Right plate, MEF p53–/– cells cultivated with apoptotic bodies from radiated REF12 cells.

FIG. 8 shows how 2×10⁶ normal mouse embryonic fibroblasts (MEF), p53−/− mouse fibroblasts were trypsinized and transferred to 10 cm petri dishes. The following day these recipient cells were co-cultured together with rat embryonic fibroblasts co-transfected with activated T24 H-ras, c-myc (REF12). These donor cells were also transfected with a neomycin selection marker, neoR and a hygromycin resistance gene fused with green fluorescence protein (pEGFP-hyg, Clontech). As a negative control normal non-transfected REFs were used as donor cells. Apoptosis was induced in 10×10⁶ REF12 and REF non-transfected cells respectively by irradiation (150 Gy) and after washing once in medium (DMEM, Hyclone) they were added to the recipient cells for co-cultivation. As a negative control human fetal lung fibroblasts (HF) were used as recipient cells. The cells were grown in Dulbecco's modified eagle's medium (DMEM, Hyclone) with 10% fetal bovine serum (Hyclone), glutamin and penicillin/streptomycin. The tissue culture medium were changed after 48 hours and then changed every three days. In some of the co-cultivation experiments, selection was started with hygromycin (80 g/ml) 48 hours after the addition of apoptotic bodies. The figure shows hygromycin resistant colonies after co-cultivation with apoptotic bodies. Left plate, wild type mouse embryonic fibroblasts (MEF), MEF with inactivated p53 cultivated with apoptotic bodies from radiated REF cells lacking the hygromycin resistance gene. Right plate, MEF p53−/− cells cultivated with apoptotic bodies from radiated REF12 cells.

Figure 9:
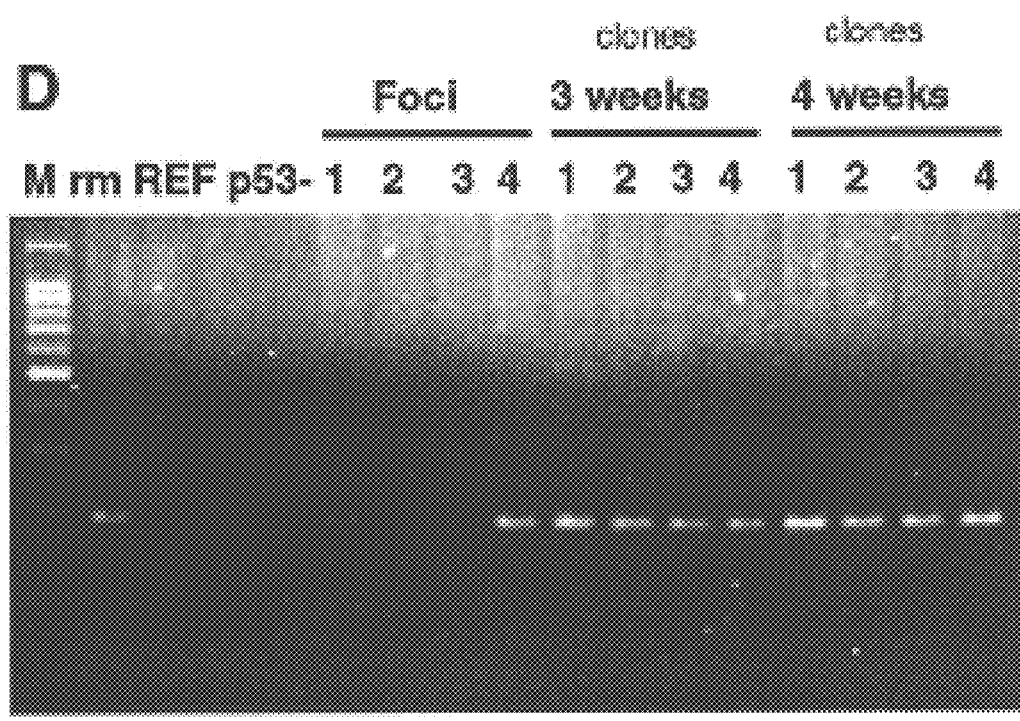
FIG. 9 shows presence of DNA encoding hygromycin resistance in hygromycin resistant clones.

FIG. 9 shows the presence of DNA encoding hygromycin resistance in hygromycin resistant clones. The figure shows presence of the hygromycin resistance gene in stable cell lines after co-cultivation with apoptotic bodies. DNA from resistant colonies were amplified for 30 seconds at 95° C., 45 seconds at 59° C. and 2 minutes at 72° C. for 30 cycles. The primer sequences for the hygromycin resistance gene were 5'-acgtaaacggccacaagttc- and 3,3'-aagtcgtgctgettcatgtg -5'.

Figure 10:
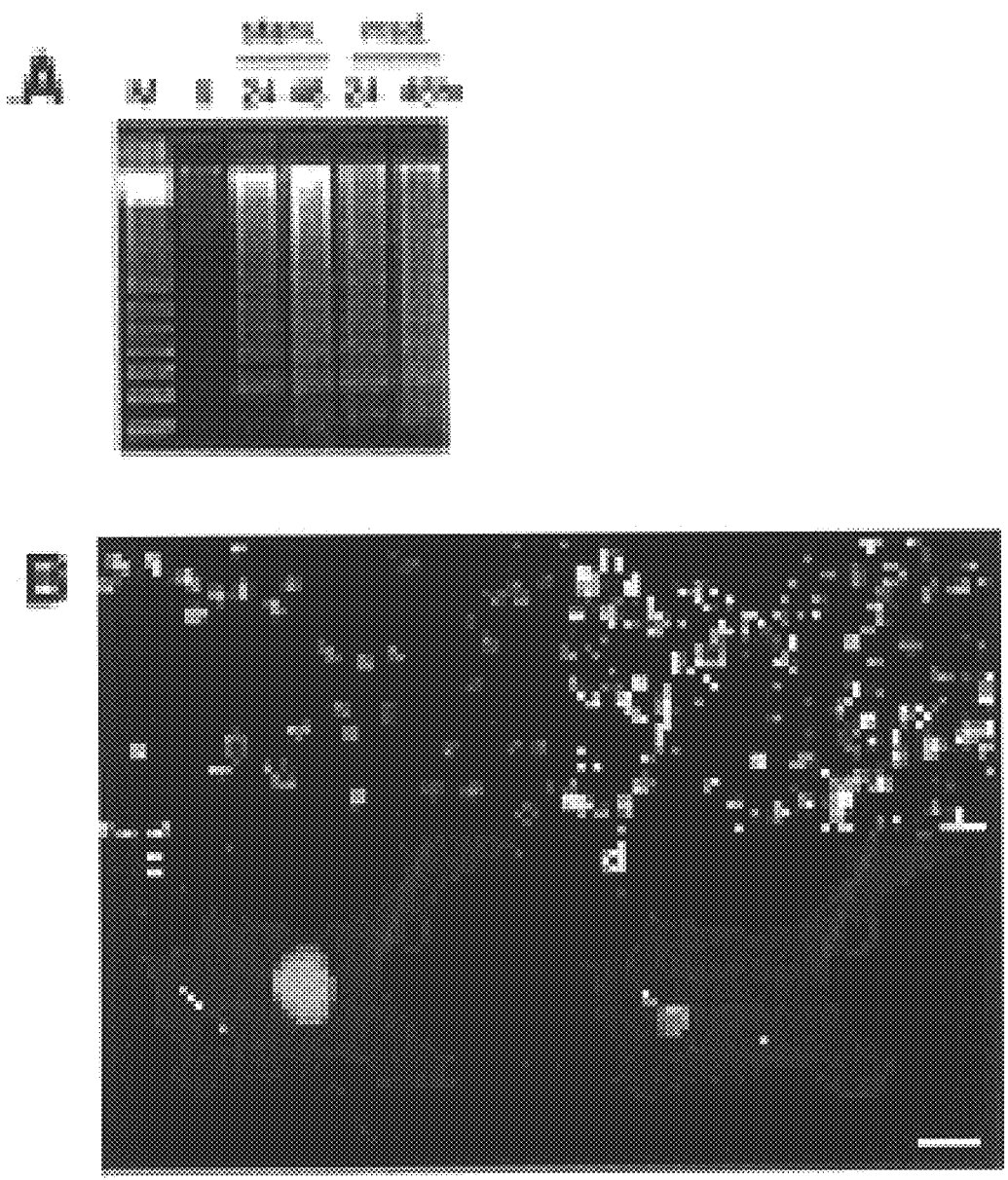
FIGS. 10A–B show internalization of apoptotic bodies by mouse embryonic fibroblasts.

FIG. 10 shows the internalization of apoptotic bodies by mouse embryonic fibroblasts. (A). Apoptosis was induced in REFrm cells either by nutrient depletion or by gamma irradiation as shown by DNA fragmentation before (0) or after 24h and 48h of culture either in nutrient depleted medium (starv.) or after irradiation (irrad.). M=123 bp DNA ladder. (B). Hoechst 33258 staining of REFrm cells (a) and REFrm cells 48h after irradiation (b) showed nuclear condensation after irradiation. F-actin was stained with rhodamine-phalloidin (c and d) to show the phagocytosis of an EGFP-labeled REFrm apoptotic body (arrow) by a mouse embryonic fibroblast. Cellular DNA was stained with Hoechst 33258 (c) and (d), shows the EGFP-positive signal of the phagocytosed REFrm apoptotic body. Size bars a and b=15 µm, c and d=6 µm.

Figure 11:
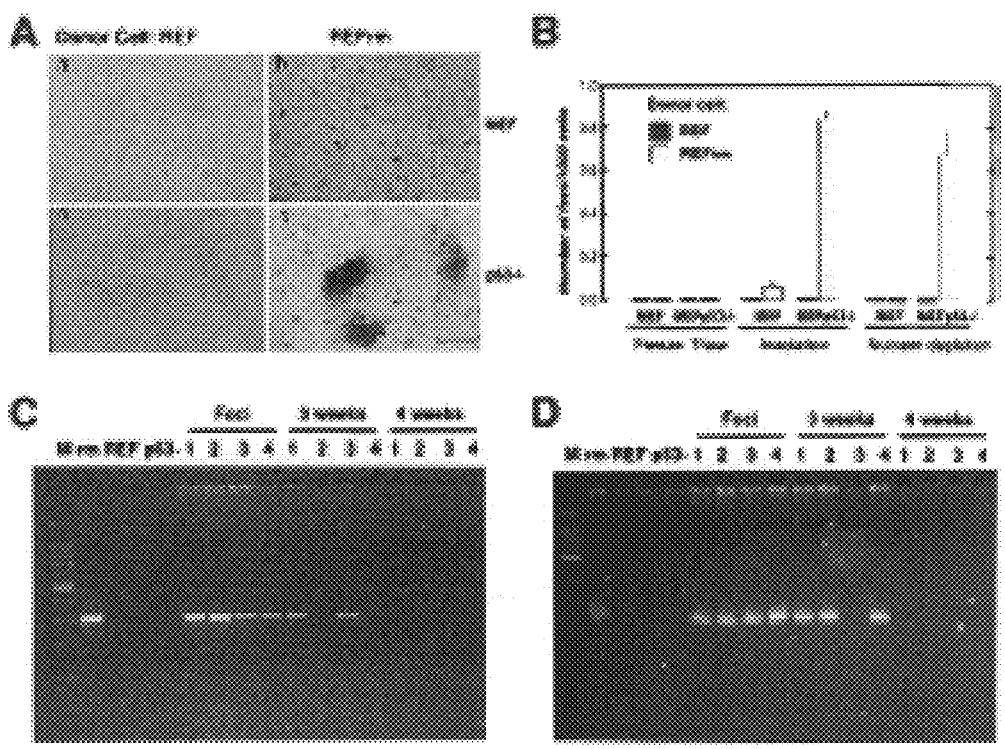
FIGS. 11A–D show apoptotic bodies derived from REFrm cells induce focus formation in MEF p53$^{-/-}$ cells.

FIG. 11 shows how apoptotic bodies derived from REFrm cells induce focus formation in MEF p53$^{-/-}$ cells. (A). MEF (a and b) or MEF p53-/- cells (c and d) were co-cultured with either apoptotic REF (a and c) or REFrm (b and d) and focus formation was analyzed after eight days in culture. Size bar 220 µm (B). frequency of focus formation in MEF and MEFp53-/- cells after co-culture with necrotic cells or apoptotic REF or REFrm cells. Necrosis was induced by freeze thawing and apoptosis was induced either by irradiation or by nutrient depletion as indicated. Results are shown as mean ±S.D. of three independent experiments. (C) and (D). PCR analysis for the presence of H-ras$^{V12}$ (C) and human c-myc (D) in donor REFrm (rm), REF, recipient MEF p53$^{-/-}$ (p53-), foci (1–4) and the resulting cell lines after 3 and 4 weeks of propagation. M=100 bp DNA ladder.

Figure 12:
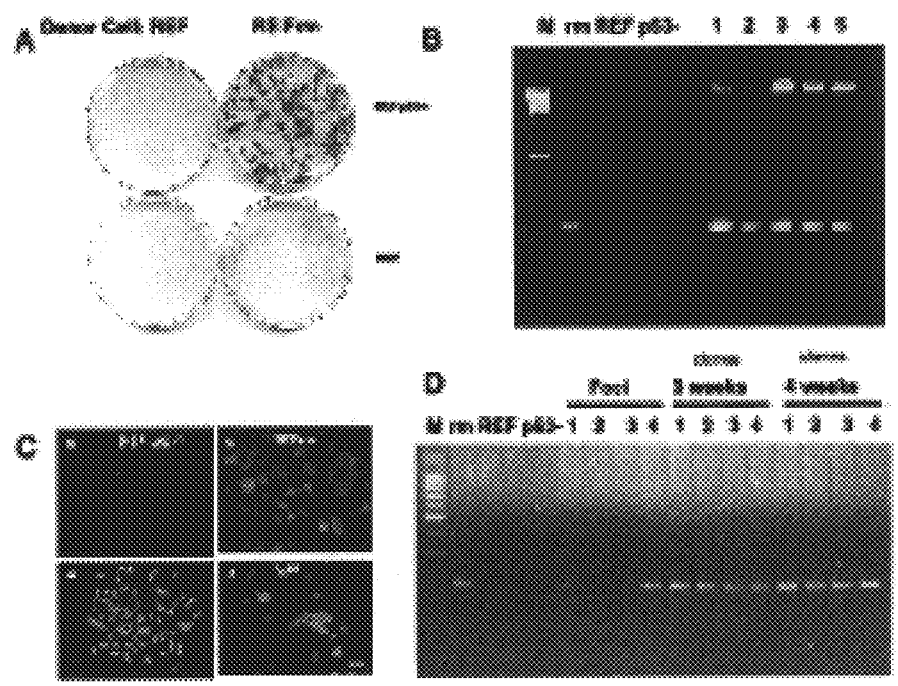
FIGS. 12A–D show induction of hygromycin resistance in MEF p53$^{-/-}$ cells.

FIG. 12 shows the induction of hygromycin resistance in MEF p53$^{-/-}$ cells. (A). MEF or MEF p53$^{-/-}$ cells were cultured with apoptotic bodies from REF or EGFP-Hyg$^r$ expressing REFrm cells. The figure shows Coomassie staining of hygromycin-resistant MEF p53$^{-/-}$ colonies cultured with REFrm apoptotic bodies. (B). PCR detection of the hyg$^r$ gene in donor REFrm (rm), REF, recipient MEF p53$^{-/-}$ (p53-) and the hygromycin resistant REFrm×MEF p53$^{-/-}$ colonies (1–5). (C). Detection of the Hyg$^r$-GFP fusion protein in MEF p53$^{-/-}$ recipient cells, REFrm donor cells and hygromycin-selected REFrm×MEF p53$^{-/-}$ clones C8 and C12. Size bar=10 µm. (D). Detection of the hyg$^r$ gene in foci induced by cultivation of REFrm apoptotic bodies with MEF p53$^{-/-}$ cells. Approximately 60% of the foci were Hyg$^r$-positive without hygromycin selection. The Hyg$^r$ gene could be maintained for over 4 weeks in the presence of hygromycin selection. Positive and negative controls were the same as in (B).

Figure 13:
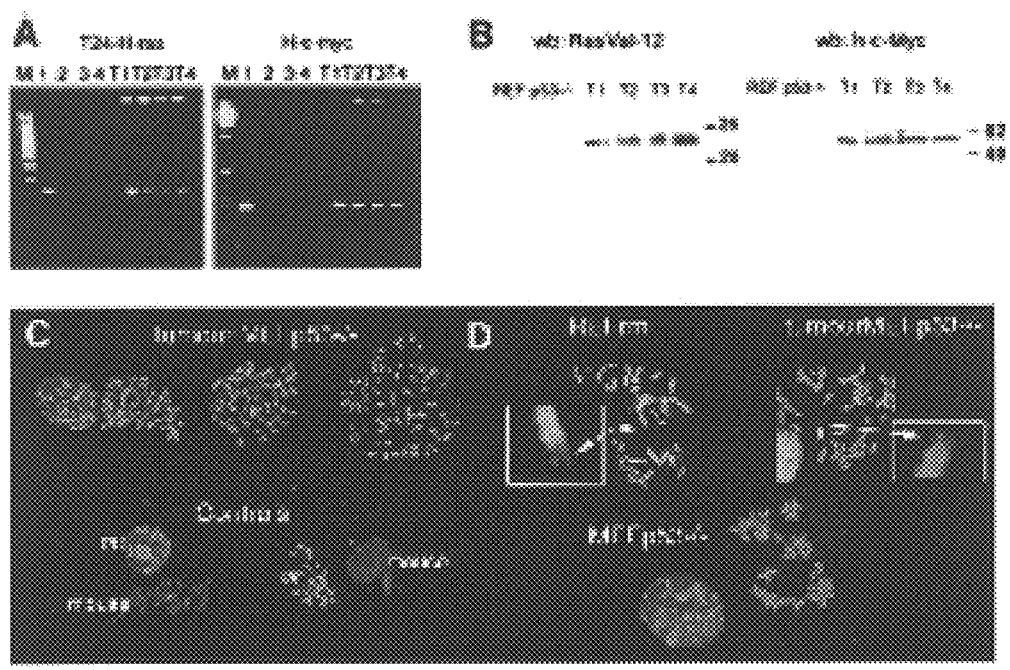
FIGS. 13A–D show that tumors derived from REFrm× MEF p53$^{-/-}$ foci injected into mice contain the H-ras$^{V12}$ and human c-myc genes.

FIG. 13 shows that tumors derived from REFrm×MEF p53$^{-/-}$ foci injected into mice contain the H-ras$^{V12}$ and human c-myc genes. (A). PCR analysis of H-ras$^{V12}$ and c-myc DNA in REFrm×MEF p53$^{-/-}$ tumors showed presence of these oncogenes in tumors 1–4 (T1–T4). Lane 1=REFrm, Lane 2=REF, Lane 3=MEF p53$^{-/-}$, Lane 4=DNA, M=100 bp ladder. (B). Western blot analysis of H-Ras$^{V12}$ and c-Myc protein expression in REFrm×MEF p53$^{-/-}$ tumors (T1–T4). The H-Ras$^{V12}$ antibody is specific to H-Ras$^{V12}$ and the c-Myc antibody is specific to human c-Myc and did not cross-react with REF or MEF p53$^{-/-}$ cells. (C). FISH analysis of rat DNA in meta-phase spreads from REFrm×MEF p53$^{-/-}$ tumors. The FITC-labeled rat DNA painting probe (green) detects rat but not mouse DNA as shown in the controls. Rat chromosomes as well as rat and mouse hybrid chromosomes could be detected in metaphase spreads from REFrm×MEF p53$^{-/-}$ tumors. DNA was counterstained with the DAPI fluorochrome (blue). (D). Detection of the human c-myc gene in meta-phase chromosomal spreads using a human c-myc-specific rhodamine-labeled probe (red). The human c-myc probe was negative in MEF p53$^{-/-}$ chromosomal spreads but is detected in metaphase spreads from REFrm cells and REFrm×MEF p53$^{-/-}$ tumors (arrows). Boxed inserts show the positive signal at a four-fold relative magnification. Blue color shows DAPI DNA staining.

Figure 14:
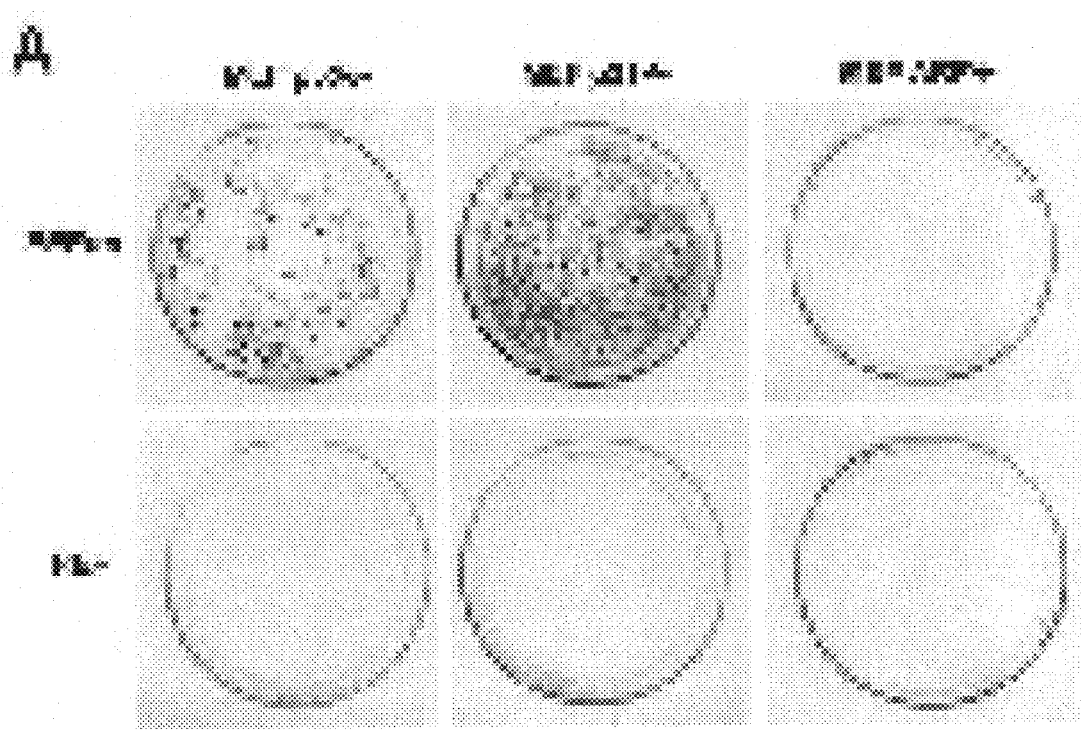
FIG. 14 show how hygromycin resistance is induced in MEF p21–/– and p53–/– cells. The data shows that the hygromycin gene can be transferred to and expressed in cells deficient in either of the p21 or p53 genes.

FIG. 14 shows the induction of hygromycin resistance in MEF p21-/- and p53-/- cells. Wild type MEF, p21-/- and p53-/- cells were cultured with apoptotic bodies from rat embryonic fibroblasts (REF) or REF cells expressing the EGFP-Hygr gene. The figure shows Coomassie staining of hygromycin-resistant MEF p21-/- and p53$^{-/-}$ colonies cultured with REFrm apoptotic bodies. The data shows that the hygromycin gene can be transferred to and expressed in cells deficient in either of the p21 or p53 genes.

Figure 15:
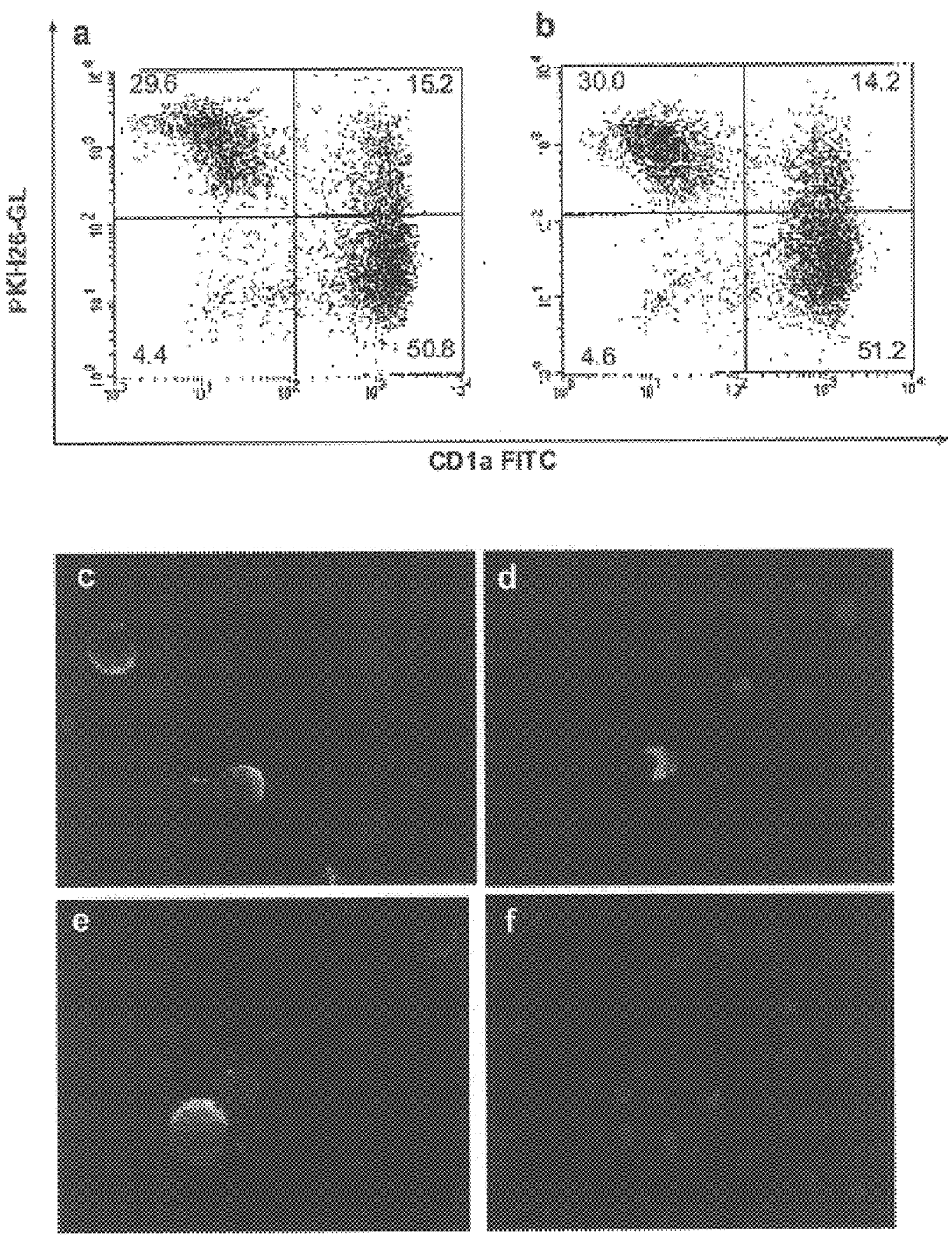
FIGS. 15a–f show how CD1a$^+$ in vitro derived DCs efficiently ingest HIV-1 infected apoptotic bodies and subsequently show HIV-1 p24 expression.

FIG. 15 shows that CD1a$^+$ in vitro derived DCs efficiently ingest HIV-1 infected apoptotic bodies and subsequently show HIV-1 p24 expression. (a) The non-infected HuT78 lymphoma T cell line or (b) HIV-1-infected HuT78$_{SF2}$ lymphoma T cell line were labeled red with the fluorochrome PKH26-GL prior to induction of apoptosis. DCs were allowed to ingest apoptotic bodies for 2h and were subsequently stained with anti-CD1a-FITC. The presented data show one representative experiment out of five. (c–f) Immunofluorescent staining showed that DCs co-cultured with apoptotic HIV-1-infected cells or cell free HIV-1 isolate express HIV-1 p24 protein. Immature DCs were co-cultured with apoptotic HIV-1-infected HuT78$_{SF2}$ cells (c), apoptotic HIV-1 infected 8E5/LAV RT$^-$ cells (d), cell free HIV-1 Ba-L virus isolate (e) or apoptotic non-infected HuT78 cells (f). DC experiment from one representative donor of nine is shown.

Figure 16:
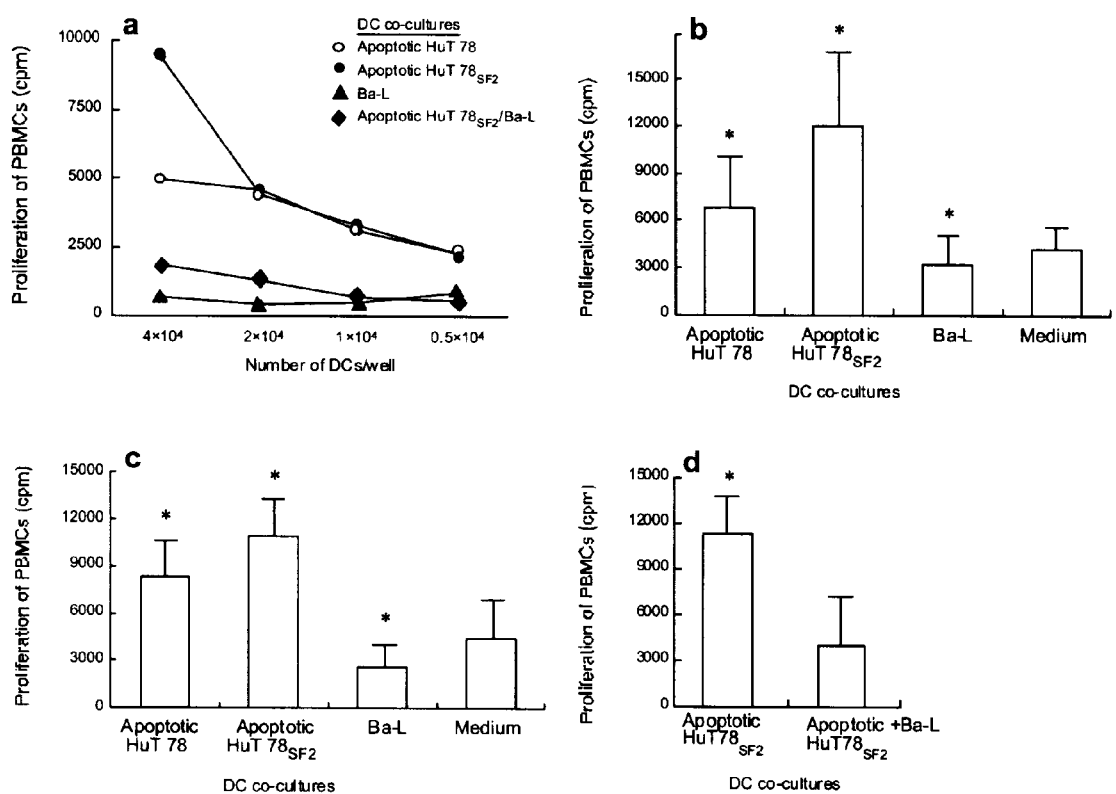
FIGS. 16a–d show how DCs co-cultured with apoptotic HIV-1-infected HuT78$_{SF2}$ cells induced autologous PBMC proliferation whereas DCs incubated with cell free HIV-1 virus isolate Ba-L abrogated this response.

FIG. 16 shows that DCs co-cultured with apoptotic HIV-1-infected HuT78$_{SF2}$ cells induced autologous PBMC proliferation whereas DCs incubated with cell free HIV-1 virus isolate Ba-L abrogated this response. (a) Immature DCs were co-cultured with apoptotic non-infected HuT78 cells (open circle), apoptotic HIV-1 infected HuT78$_{SF2}$ cells (filled circle), or HIV-1 Ba-L isolate (filled triangle) for 6 days. Co-cultured DCs were titrated (0.5–4×10$^4$ DCs/well) prior to addition of autologous PBMCs (1×10$^5$ PBMCs/well), A mixture of DCs co-cultured with apoptotic HuT78$_{SF2}$ cells and DCs exposed to HIV-1 Ba-L (filled diamond) was also included. Proliferation was measured by $^3$H-thymidine uptake. The results represent the mean cpm values from triplicate measurements. One representative experiment of four is shown. DCs (3×10$^4$ DCs/well) were co-cultured as indicated in the (b) presence or (c) absence of LPS. The results represent the mean ±SD from experiments on DCs from four donors. *P<0.05 compared to DC-PBMC cultures grown in medium only. (d) DCs co-cultured with apoptotic HuT78$_{SF2}$ cells induced significant PBMC proliferation compared to a DC mixture composed of DCs exposed to HIV-1 Ba-L for 6 days and DCs co-cultured in parallel with apoptotic HuT78$_{SF2}$ cells for 6 days (*P<0.05).

Figure 17:
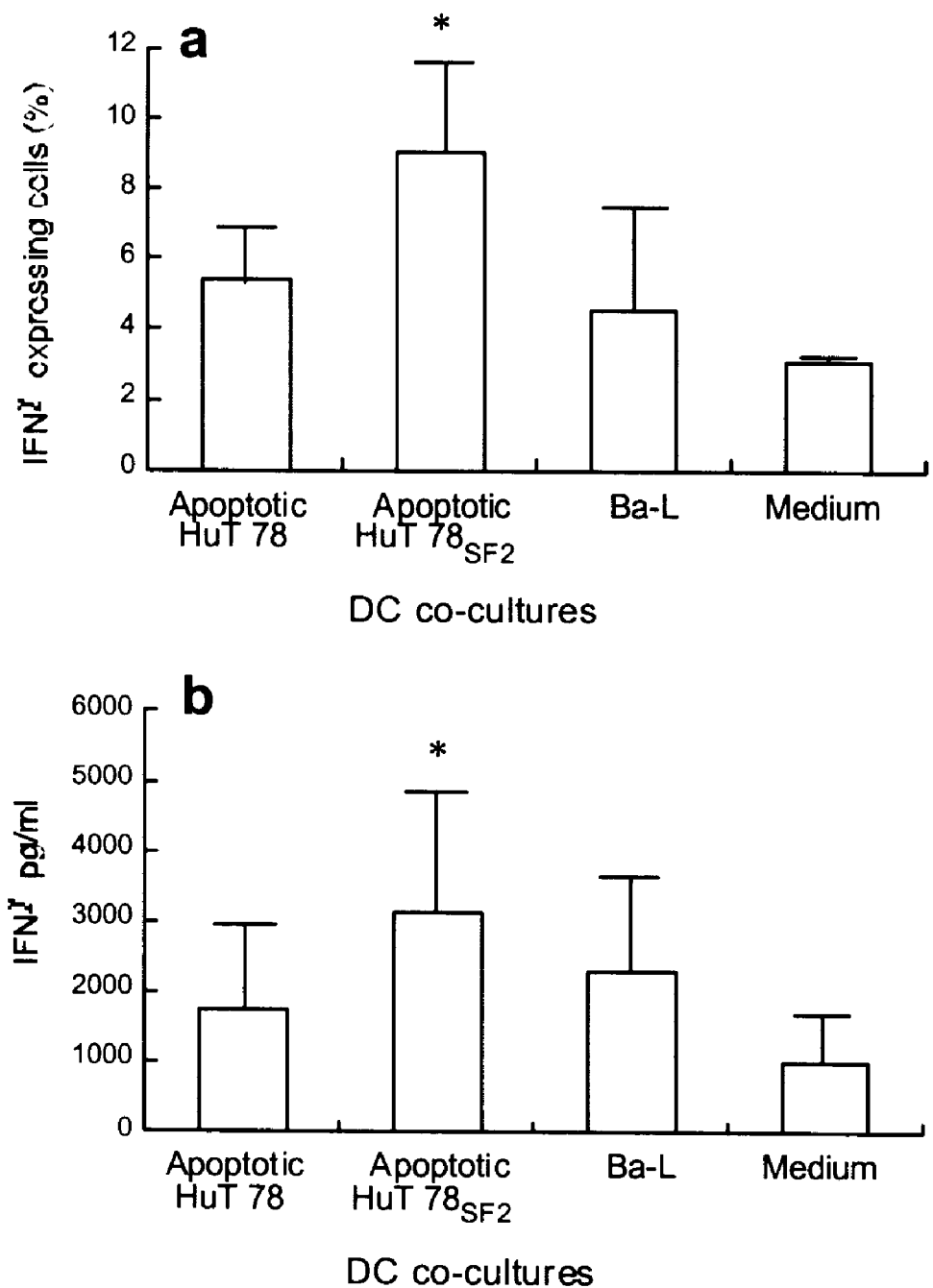
FIGS. 17a–b show induction of IFN-γ production in PBMCs after priming with co-cultured DCs. Graphs show production of IFN-γ in PBMCs induced by the different co-cultures of DCs.

FIG. 17 shows induction of IFN-γ production in PBMCs after priming with co-cultured DCs. Graphs show production of IFN-γ in PBMCs induced by the different co-cultures of DCs. Immature DCs were co-cultured with apoptotic HuT78 cells, apoptotic HuT78$_{SF2}$ cells, exposed to HIV-1 Ba-L or medium only before addition of autologous PBMCs. (a) The frequency of IFN-γ expressing cells was evaluated by in situ imaging. (b) The collected supernatants were assessed for IFN-γ release by ELISA. Bars show mean ±SD values revealed from co-cultures of DCs from four donors. *P<0.05 compared to DC-PBMC cultures grown in medium only.

Figure 18:
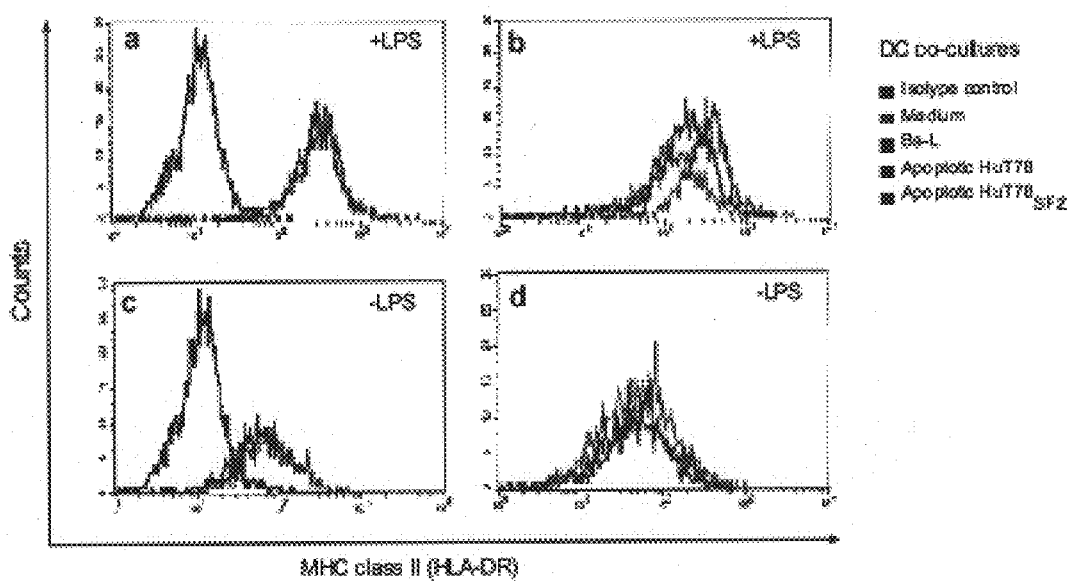
FIGS. 18a–d show that uptake of apoptotic T cell lymphoma cells leads to increased MHC class II expression on DCs in the presence of LPS.

FIG. 18 shows that uptake of apoptotic T cell lymphoma cells leads to increased MHC class II expression on DCs in the presence of LPS. Immature DCs were co-cultured with apoptotic HIV-1-infected HuT78$_{SF2}$ cells (green), apoptotic non-infected HuT78 cells (red), exposed to HIV-1 Ba-L (blue) or medium only (brown). (a–b) DCs co-cultured as indicated in the presence of LPS. (a) No difference in MHC class II expression was detected in DCs co-cultured with apoptotic HIV-1-infected HuT78$_{SF2}$ cells compared to apoptotic non-infected HuT78 cells. (b) DCs co-cultured with apoptotic cells showed increased MHC class II expression compared to DCs exposed to HIV-1 Ba-L or cultured in medium only. Experiments on DCs from one representative donor of six are shown. (c–d) No detectable difference in MHC class II expression was detected in the indicated DC co-cultures in the absence of LPS. Data from experiments on DCs from one representative donor of five is shown.

FIGS. 19A–B illustrates the experiment performed in example 5 of the present application. FIG. 19(A) shows the vaccination scheme for mice vaccinated with apoptotic MuLV-HIV infected syngenic cells: C57B1/6 mice (n=36) were immunized intraperitoneally (i.p.) with either apoptotic virus infected or apoptotic uninfected syngenic spleen cells. Three weeks later the first groups of mice were sacrified (n=12) and the remaining mice received a booster vaccination with apoptotic cells. After additional three weeks, the second groups of mice were sacrificed (n=12) and the remaining mice (n=12) were challenged with pseudotype virus. FIG. 19(B) shows the T-cell proliferation obtained. Spleen cells from immunized mice were stimulated in vitro with ConA, p24, nef or a control protein and proliferation was measured by 3H-thymidine uptake. Mice inoculated with apoptotic HIV-1/MuLV infected spleen cells showed a strong induction of nef-specific lymphocyte proliferation (6 out of 6 mice) after the first vaccination, while mice inoculated with apoptotic uninfected cells (n=6) did not show any nef-induced proliferation.

FIGS. 20A–B show the stimulation index of MuLV-HIV infected cells as compared to control cells after a 1$^{st}$ and a 2$^{nd}$ immunization as obtained in accordance with example 5. ELISA was used to detect presence of IFN-g, IL-2 and IL-4 in the tissue culture supernatants from the in vitro stimulated spleen cells. Mice vaccinated with apoptotic HI-1/MuLV infected spleen cells showed p24 specific induction of IFN-γ in 5 out of 5 mice analyzed. One mouse in the group vaccinated with apoptotic control cells showed induction of IFN-γ in the supernatant but it was not p24 specific since stimulation with the control protein gave a similar induction of IFN-γ.

FIGS. 21A–B show a quantification of the levels of anti-HIV-1 specific antibodies in sera and faeces from mice immunized in accordance with example 5. Vaccination with apoptotic HIV-1/MuLV infected spleen cells resulted in a significant rise in levels of anti-HIV-1 specific antibodies, which was further boosted after challenge.

EXPERIMENTAL

The present examples are included herein for illustrative purposes only and should not be construed as limiting the scope of the application as defined by the appended claims. All references given below and elsewhere in the present specification are included herein by reference.

EXAMPLE 1: Horizontal transfer of DNA

Materials and methods

Cocultivation experiments:

Human fetal lung fibroblasts, bovine aortic endothelial cells (established in the laboratory of Dr Judah Folkman, Children's Hospital, Boston, Mass.), human monocytes (purified from normal human blood as previously described (Freundlich B, Avdalovic N: Use of gelatin/plasma coated flasks for isolating human peripheral blood monocytes. *J Immunol Methods* 62:31, 1983), or human vascular smooth muscle cells (kindly provided by Britt Dahlgren, Karolinska Hospital, Stockholm, Sweden) were trypsinized and transferred to 8-well Lab Tek slides (Nalgene; Nunc, Copenhagen, Denmark) for immunostaining (50,000 cells/well) or 10-cm Petri dishes for fluorescence in situ hybridization (FISH) analysis. The following day, EBV-carrying lymphoid cell lines were irradiated with 150 Gy and added to the cultures at a ratio of 5:1. Alternatively, cells were treated with 16 µg/mL etoposide (Sigma, St Louis, Mo.) for 24 hours, washed three times in phosphate-buffered saline (PBS), and then added to cultures of human fetal fibroblasts. The tissue culture medium was first changed after 48 hours and ten changed every 3 days. Cell lines negative for EBV were also included as negative controls. For immunostaining, cells were washed once with PBS and then fixed in −20° C. methanol:acetone, 2:1 (vol:vol) for 5 minutes and air-dried. Cells were rehydrated in balanced salt solution (BSS) and then incubated with human serum antibodies against EBNA1–6 or with serum from an EBV-negative donor for 15 minutes at 37° C. and washed in 3× BSS (Falk K, Emberg I, Sakthivel R, Davis J, Christensson B, Luka J, Pkano M, Grierson H L, Klein G, Purtilo D T: Expression of Epstein-Barr virus-encoded proteins and B-cell markers in fatal infectious mononucleosis. *Int J Cancer* 46:976, 1990). EBNA1 was detected with human serum preadsorbed with an EBNA1-negative, EBNA2–6-positive cell line E95-A-BL28 (Falk K, et al.,1990, supra). Positive staining was visualized by incubation sequentially with complement and fluorescein isothiocyanate (FITC)-labeled anticomplement antibodies as previously described (Reedman B, Klein G: Cellular localization of an Epstein-Barr-virus (EBV)-associated complement fixing antigen in producer and non-producer lymphoblastoid cell lines. *Int J Cancer* 11:499, 1973). The mouse monoclonal antibody PE2 was also used to detect EBNA2 expression by immunofluorescence (Young L, Alfieri C, Hennessy K, Evans H, O'Hara C, Anderson K C, Ritz J, Shapiro R S, Rickinson A, Kieff E, Cohen J I: Expression of Epstein-Barr virus transformation-associated genes in tissues of patients with EBV lymphoproliferative disease. *N Engl J Med* 321:1080, 1989). The presence of cells in viral lytic cycle was detected by immunostaining against viral capsid antigen (VCA) or early antigen (EA) using FITC-conjugated sera from Burkitt's lymphoma (EA) or nasopharyngeal carcinoma (VCA) patients according to established protocols (Klein G, Dombos L, Gothoskar B: Sensitivity of Epstein-Barr virus (EBV) producer and non-producer human lymphoblastoid cell lines to superinfection with EBV-virus. *Int J Cancer* 10:44, 1972; and Henle W, Henle G E, Horwitz C A: Epstein-Barr virus specific diagnostic tests in mononucleosis. Hum Pathol 5:551, 1974). For detection of EBER1 and 2 nuclear RNAs, cells were fixed in 4% paraformaldehyde for 4 hours, pretreated with 5 µg/mL proteinase K at 37° C. for 30 minutes, and hybridized according to the protocol of the manufacturer (DAKO, Glostrup, Denmark).

Apoptosis assays:

For DNA fragmentation assays, 5×10$^6$ cells were resuspended in 10 mmol/L EDTA, pH 8, 0.5% Triton X-100, and lysed with 10 strokes with a Dounce homogenizer. Cells were pelleted and the resulting supernatant was incubated with 100 µg/mL RNase A at 37° C. for 1 hour. Sodium dodecyl sulfate (SDS) and proteinase K were added to concentrations of 1% (wt/vol) and 200 µg/mL, respectively, and incubated at 50° C. for 2 hours. The DNA was precipitated overnight at −20° C. by adding 1/10 of total volume 5 mol/l NaCl and 2.5 vol of 99% EtOH. Precipitated DNA was collected by centrifugation at 13,000 rpm at 4° C. in a microcentrifuge. Fragmentation was analyzed by electrophoresis in 1.5% agarose gels.

FISH:

Total human genomic DNA from a normal donor was labeled with tetramethyl-rhodamine-dUTP using a nick translation kit (GIBCO-BRL, Grand Island, N.Y.). The BamHI W fragment from the EBV genome was labeled with biotin-11-dUTP with the same method. FISH analysis was performed according to the protocol of Pinkel D, Straume T, Gray J W: Cytogenetic analysis using high-sensitivity fluorescence hybridization. *Proc Natl Acad Sci USA* 83:2934, 1986. Slides were denatured for 5 minutes in 70% formamide, 2x SSC at 75° C. and subsequently dehydrated sequentially in cold 70%, 95% and 100% ethanol and air-dried. Probes were denatured for 10 minutes at 80° C. in the hybridization mix (50% formamide, 2x SSC, and 10% dextran sulphate). Slides were hybridized overnight at 37 ° C. and then washed in 50% formamide, 2x SSC for 4x3 minutes, and for 3x3 minutes in 2x SSC at 46° C. Positive hybridization with the biotinylated BamHI W probe was detected using avidin-conjugated to fluorescein (Vector, Burlingame, Calif.). The tetra-methyl-rhodamine-dUTP-labeled human probe was viewed directly by fluorescence microscopy without signal amplification. Cells were counterstained with the DNA fluorochrome 4,6-diamidino-2-phenyl indole (DAPI) and mounted in anti-bleach medium. Results were analyzed using a fluorescence microscope (Leitz-DMRB; Leica, Heidelberg, Germany) equipped with a Hamamatsu 4800 COD camera (Hamamatsu, Herrsching, Germany). Digital images were processed in Adobe Photoshop (Adobe, Mountain View, Calif.). For three-dimensional imaging, pictures were sampled in the 2-axis and deconvoluted using digital confocal imaging (Openlab, Improvision, Coventry, UK). The resulting images were processed using the 3-D rendering software (Openlab).

RESULTS EXAMPLE 1

Expression of EBV-encoded genes in fibroblasts after uptake of apoptotic bodies:

The EBV-negative Burkitt's lymphoma cell line BL41 and its EBV-positive derivative BL41/95 was used for cocultivation with human fetal fibroblasts (HF). The BL41/95 is an in vitro EBV-infected BL41 cell line that carries integrated copies of EBV that express the EBNA1 and 2 (as detected by immunofluorescence) but does not produce virus (Cordier M, Calendar A, Billoud M, Zimber U, Rousselet C, Pavlish O, Banchereay J, Tursz T, Bornkamm C, Lenoir G M: Stable transfection of Epstein-Barr virus (EBV) nuclear antigen 2 in lymphoma cells containing the EBV P3H3R1 genome induces expression of B-cell activation molecules CD21 and CD23. *J Virol* 64:1002, 1990; and Nakagomi H, Pisa P, Pisa E K, Yamamoto Y, Halapi E, Backlin K, Juhlin C, Kiessling R: Lack of interleukin-2 (IL-2) expression and selective expression of IL-10 mRNA in human renal cell carcinoma. *Int J Cancer* 63:366, 1995). (Barbro Ehlin-Eriksson, personal communication, December 1998). Apoptosis was reproducibly induced by irradiating cells at 150 Gy. Radiation induced DNA ladder formation as analyzed by DNA gel electrophoresis. Staining of nuclei with the DNA fluorochrome Hoechst 33258 showed nuclear condensation of DNA and fragmentation of nuclei into apoptotic bodies (FIGS. 1A and B). Irradiation resulted in 100% cell death after 4 days, as analyzed by trypan blue exclusion (FIG. 1C).

Apoptotic bodies cultivated with human fetal fibroblasts became phagocytosed and internalized within 1 hour, as previously reported (Hall S E, Savill J S, Henson P M, Haslett C: Apoptotic neutrophils are phagocytosed by fibroblasts with participation of the fibroblast vitronectin receptor and involvement of a mannose/fucose-specific lectin. *J Immunol* 153:3218, 1994). To follow the fate of internalized DNA, the BL-41 and BL41/95 were labeled with 2, 3 Bromo-deoxyuridine (BrdU) for 48 hours before irradiation. The irradiated cells and HF cells were cocultivated for 1 week, as previously described (Jones K, Rivera C, Sgadari C, Franklin J, Max E E, Bhatia K, Tosato C: Infection of human endothelial cells with Epstein-Barr virus. *J Exp Med* 182:1213, 1995). The presence of BL41 and BL41/95 DNA in HF cells was detected by immunostaining with antibodies against BrdU. In both cell lines, apoptotic bodies were still detectable in a perinuclear location in the cytoplasm of the HF cells after 1 week of cocultivation (FIG. 2a). Double staining with KF human serum against the EBNA complex 1–6 showed that nuclei of HF cells containing a BL41/95 apoptotic body stained positive for EBNA (FIG. 2a). The presence of EBNA1 in cocultures of HF cells was shown by staining with human serum preadsorbed with an EBNA1-negative, EBNA2–6-positive cell line E95-A-BL28. Control experiments in which fibroblasts were cultivated with the original EBV-negative BL41 cell line were always negative (FIG. 2a). EBV did not infect HF cells, as shown by the lack of positive EBNA staining after incubation with B95-8 virus (Miller G, Lipman M: Release of infectious Epstein-Barr virus by transformed marmoset leukocytes. *Proc Natl Acad Sci USA* 70:190, 1973) that could infect and transform B cells in parallel cultures (Table 1).

One explanation for the present findings is that the EBNA1-positive nuclei were derived from entire lymphoid nuclei taken up by the fibroblast cells. To exclude this possibility, fibroblasts were pulsed with BrdU before cocultivation with irradiated (unlabeled) BL41/95 cells. Double-staining of cells with BrdU and EBNA1 antibodies showed EBNA1 staining in nuclei that also were positive for BrdU. Sporadic cells could be detected containing more than one EBNA1-staining nuclei. These nuclei were always of fibroblastic origin, as shown by positive BrdU staining (FIG. 2b).

Integrated ABV-DNA but not episomal induces expression of EBV-encoded genes in fibroblasts:

It was next investigated whether cocultivation of apoptotic bodies derived from other EBV-carrying cell lines could induce EBNA expression to HF cells. Apoptosis was elicited by irradiation in 9 EBV-carrying cell lines and 3 EBV-negative cell lines. The resulting apoptotic bodies were cultivated with HF cells for 3 weeks. Subsequently, the cells were tested for the presence of the EBV-encoded RNAs, EBER1 and 2, by in situ hybridization analysis and for EBNA1 expression by immunofluorescence staining (Table 1 and FIGS. 3G and H). The donor cell lines could be divided into two groups: apoptotic bodies from 5 of the cell lines (Table 1, upper part) induced EBNA1 and EBER expression in HF, whereas the other 4 could not. The lines that could act as EBV donors induced EBNA1 and EBER expression in 1% to 5% HF cells. The other cell lines induced little or no EDNA or EBER expression in the recipient cells (<5 of 500,000 cells in 5 experiments). The cell lines that could induce expression of EBV markers in HF cells carried integrated EBV genomes (Lawrence J B, Villnave Calif., Singer R H: Sensitive, high resolution chromatin and chromosome mapping in situ: Presence and orientation of two closely integrated copies of EBV in a lymphoma line. *Cell* 52:51, 1988; Hurley E A, Klaman L D, Agger S, Lawrence J B, Thorley-Lawson D A: The prototypical Epstein-Barr virus-transformed lymphoblastoid cell line IB-4 is an unusual variant containing integrated but no episomal viral DNA. *J. Virol* 65:3958, 1991; Henderson A, Ripley S, Heller M, Kieff E: Chromosome site for the Epstein-Barr virus DNA in a Burkitt tumor cell line and lymphocytes growth transformed in vitro. *Proc Natl Acad Sci USA* 80:1987, 1983; and Hurley E A, Agger S, McNeil J A, Lawrence J B, Calendar A, Lenoir G, Thorley-Lawson D A: When Epstein-Barr virus persistently infects B-cell lines, it frequently integrates. *J Virol* 65:1245, 1991) whereas the ineffective cell lines contained episomal EBV-DNA (Table 1) (Gulley M L, Raphael M, Lutz C T, Ross D W, Raab-Traub N: Epstein-Barr virus integration in human lymphomas and lymphoid cell lines. *Cancer* 70:185, 1992).

The induction of EBNA1 in HF cells was not restricted to radiation-induced apoptosis, because a similar effect was observed with cells treated with etoposide (Table 2). Interestingly, cocultivation of HF cells with Namalwa cells exposed to hypo-osmotic shock did not affect EDNA1 expression in HF cells. This finding indicates that transfer of expression of EBV-encoded genes is mediated by EBV-carrying apoptotic by not necrotic cells.

Host-dependent expression of EBNA2

It was next investigated whether the expression pattern of EBV-encoded genes depended on the phenotype of the donor or the host. Earlier findings have shown that EBNA2 is only expressed in immunoblastic lines (Emberg I, Falk K, Minarovits J, Busson P, Tursz T, Masucci M G, Klein G: The role of methylation in the phenotype-dependent modulation of Epstein-Barr nuclear antigen 2 and latent membrane protein genes in cells latently infected with Epstein-Barr virus. *J Gen Virol* 70:2989, 1989). EBNA2 was expressed in all donor lines studied, with the exception of Rael, P3H3, and EHR-A-BL41 (Emberg I, Falk K, Minarovits J, Busson P, Tursz T, Masucci M G, Klein G: The role of methylation in the phenotype-dependent modulation of Epstein-Barr nuclear antigen 2 and latent membrane protein genes in cells latently infected with Epstein-Barr virus. *J Gen Virol* 70:2989, 1989; Emberg I, Kallin B, Dillner J, Falk K, Ehlin-Eriksson B, Hammarskjöld M-L, Klein G: Lymphoblastoid cell lines and Burkitt-lymphoma-derived cell lines differ in the expression of a second Epstein-Barr virus encoded nuclear antigen. *Int J Cancer* 38:729, 1986, and Trivedi P, Cuomo L, de Campos-Lima P O, Imreh M P, Kvarnung K, Klein C, Masucci M G: Integration of a short Epstein-Barr virus DNA fragment in a B95–8 virus converted Burkitt lymphoma line expressing Epstein-Barr nuclear antigens EBNA2 and EBNA5. *J Gen Virol* 74:1393, 1993). It was investigated whether the expression pattern of EBNA2 was downregulated in EBNA1- and EBER-expressing HF cells. No detectable EBNA2 staining could be observed with either the PE2 anti-EBNA2 monoclonal antibody or adsorbed EBNA-2 specific human serum (Table 1). This finding is consistent with the lack of EBNA2 expression in EBV-carrying non-B cells, including somatic cell hybrids between B and non-B cells with a dominating fibroblastic or epithelial phenotype (Contreras-Brodin B A, Anvret M, Imreh S, Altiok E, Klein G, Masucci M G: B cell phenotype-dependent expression of the Epstein-Barr virus nuclear antigens EBNA-2 to EBNA-6:Studies with somatic cell hybrids. *J Gen Virol* 72:3025, 1991).

TABLE 1

Induction of EBNA1 and EBER Expression in HF Cells After Coculture With Apoptotic Bodies From Lymphoid Cell Lines.

| | | HF Phenotype after Cocultivation | | |
|---|---|---|---|---|
| Donor Cell | EBV Status | EBNA1 | EBNA2 | EBER1 + 2 |
| BL41/95 | Integrated | 2.5% ± 0.4% | — | 1.2% ± 0.3% |
| EHR-A-BL41 | Integrated | 1.9% ± 0.4% | — | 1.4% ± 0.4% |
| IB-4 | Integrated | 3.0% ± 0.2% | — | 3.4% ± 0.8% |
| Namalwa | Integrated | 4.3% ± 0.4% | — | 2.9% ± 0.3% |
| Raji | Integrated/episomal | 4.0% ± 0.3% | — | ND |
| Jijoye M13 | Episomal | <1/500,000 | — | <1/500,000 |
| P3H3 | Episomal | <1/500,000 | — | <1/500,000 |
| Rael | Episomal | <1/500,000 | — | <1/500,000 |
| CBMI Ral Sto | Episomal | <1/500,000 | — | <1/500,000 |
| BL41 | Negative | — | — | — |
| Ramos | Negative | — | — | — |
| BL28 | Negative | — | — | — |
| B95.8 virus | Virus | — | — | — |
| No donor | — | — | — | — |

Expression of EBV markers, EBNA1, EBNA2, and EBER1 + 2, in HF cells after cocultivation for 3 weeks with irradiated EBV-positive or -negative lymphoid cell lines. EBV-carrying cell lines could be divided into those with integrated EBV genomes and those with episomal genomes. EBNA1 and 2 expression was analyzed by immunofluorescence staining and EBER1 + 2 expression was detected by in situ hybridization analysis. The percentage of positive cells was estimated by counting a minimum of 500 cells in triplicate samples. Experiments were repeated at least three times for each cell line.
Abbreviation: ND, not detected.

TABLE 2

Expression of EBNA 1–6 in Human Fetal Fibroblasts After 3 Weeks of Coculture With Apoptotic/Necrotic Namalwa Cells

| Induction of Cell Death | EBNA 1–6 Expression In HF cells |
|---|---|
| Radiation | 4.1% |
| Etoposide | 2.5% |
| Osmotic shock | ND |

Expression of EBNA1–6 in human fetal fibroblasts after 3 weeks of coculture with Namalwa cells treated with irradiation, etoposide, or hypo-osmotic shock.
Abbreviation: ND, not detectable.

High efficiency transfer of expression EBV to macrophages and endothelial cells:

It was have also tested whether integrated EBV can be transferred with similar efficiency to other cell types. Apoptotic bodies derived from Namalwa cells were cultured with either bovine aortic endothelial (BAE) cells, human monocytes, or vascular smooth muscle cells for 3 weeks. Both monocytes and BAE cells showed a high percentage of EBNA1–6-positive cells (20% to 50% positive EBNA1–6 staining after 3 weeks of cocultivation; FIGS. 3A through F and Table 3). Smooth muscle cells exhibit a significantly lower frequency of uptake and expression of EBNA1–6 (<0.01%). The high efficiency with which monocytes and endothelial cells are induces to express EBNA1 may relate to their normally high phagocytotic activity.

Presence of DNA from apoptotic cells in the nuclei of recipient cells:

The maintenance of high EBNA1 and EBER expression over more than 3 weeks, the integration dependent expression of these genes, and the recipient cell type-related expression pattern (EBNA1$^+$, EBNA2$^-$) suggested that integrated EBV sequences were transferred to the phagocytotic host during cocultivation. It was therefore examined whether DNA from apoptotic lymphoid cell lines was transferred to the nuclei of the recipient cells. FISH analysis was used to follow the fate of EBV as well as genomic DNA after phagocytosis by bovine endothelial cells. (Coculture of cells from two different species permitted us to distinguish between the DNA of the donor cells from that of the recipient cells. Total human genomic DNA was labeled with tetra-methyl-rhodamine-dUTP and used as a probe to identify DNA of human origin. Hybridization of human DNA to Namalwa interphase nuclei resulted in a uniform hybridization pattern with no detectable cross-reactivity to bovine nuclei (FIG. 4A). The presence of EBV-DNA was assayed by FISH analysis using a biotin-labeled BamHI W fragment as a probe (a 3-kb fragment that is repeated 6 to 10 times in the EBV genome) (Lawrence J B, Villnave C A, Singer R H: Sensitive, high resolution chromatin and chromosome mapping in situ: Presence and orientation of two closely integrated copies of EBV in a lymphoma line. *Cell* 52:51, 1988; and Skare J, Strominger J: Cloning and mapping of BamHI endonuclease fragments of DNA from the transforming strain B95-S strain of the Epstein-Barr virus. *Proc Natl Acad Sci USA* 77:3860, 1980). The BamHI W probe gave two distinct signals in Namalwa nuclei, as previously reported, Lawrence J B et al, 1988, supra and Skare J et al, 1980, supra, whereas all BAE nuclei were negative (FIG. 4A).

The transfer of EBV and human DNA was then analyzed in bovine endothelial cells cultured with apoptotic Namalwa cells. Using the human DNA- and EBV-specific probes simultanously, it was shown that approximately 17% of the bovine endothelial nuclei contained human DNA and 15% of the bovine nuclei analyzed a positive signal with the BamHI W (FIG. 4 and Table 4). Similar frequencies were also observed in nuclei from BAE cells cultured with apoptotic IB4 cells (Table 4). In the bovine nuclei showing positive hybridization with both probes, signals overlapped in the same nuclear compartment (FIGS. 4B through D). Transfer of human DNA was also detectable in 3% of the nuclei after coculture of BAE cells and the EBV-negative BL41 line (FIG. 4F). As expected, no positive signal could be detected in these cells with the BamHI W probe. To exclude the possibility that the positive signal was originating from cytoplasmic apoptotic DNA, positive signals were also analyzed by digital confocal microscopy. Images were sampled in the z-axis and subsequently processed with 3-D rendering software to generate three-dimensional pictures (FIG. 4G). The nuclei and incoming DNA could be viewed at different angles and depths that showed that the positive signal was residing within the nuclear cage.

TABLE 3

Expression of EBNA1–6 After Culture With
Apoptotic Bodies From the Namalwa Cell Line

| Recipient Cell Type | EBNA1–6 | EBNA2 |
| --- | --- | --- |
| Human monocytes | 51% | — |
| BAE cells | 20% | — |
| Human fetal fibroblasts | 4% | — |
| Human smooth muscle cells | <0.01% | — |

Expression of EBNA1–6 in human fetal lung fibroblasts, BAE cells, human monocytes, or human vascular smooth muscle cells cocultivated for 3 weeks with irradiated Namalwa cells. Cells were analyzed by immunofluorescent staining using human serum against EBNA1–6 and EBNA2. The table shows values from a representative experiment. The experiments were performed three times (except for the cultivation with macrophages, which was performed twice).

TABLE 4

Frequency of DNA Transfer From Apoptotic
Bodies to Bovine Endothelial Cells

| Probes | BL41* + BAE | Namalwa* + BAE | IB4* + BAE |
| --- | --- | --- | --- |
| Human DNA | 3% | 17% | 12% |
| EBV BamHI W | 0% | 15% | 11% |

Frequency of transfer of human and EBV-DNA in BAE cells after 3 weeks of culture with apoptotic bodies derived from BL41 (EBV-negative), Namalwa cells, or IB-4-cells (both with integrated copies of EBV). Two-color FISH analysis was used to estimate the percentage of nuclei that were positive for the human-specific of EBV-specific probes.
*Irradiated cells.

EXAMPLE 2: Transfer of HIV DNA by a receptor-independent mechanism

Materials and Methods

Cell cultures and HIV-1 strains:

Human fetal lung fibroblasts and a human endothelial cell line (EaHy 926) (Edgell, C. J., C. C. McDonald, and J. B. Graham. 1983 Permanent cell line expressing human factor VIII-related antigen established by hybridization, *Proc. Natl. Acad. Sci. USA*, 80:3734) were cultured in DMEM (HyClone Europe, Perstorp, Sweden) supplemented with 2 mM L-glutamine (Life Technologies, Täby, Sweden), penicillin and streptomycin (Life Technologies) HEPES (Life Technologies), and 10% FCS (HyClone). These cells were treated with trypsin-EDTA (Life Technologies), washed twice in PBS supplemented with 10% FCS, and transferred to Lab-Tek chamber slides (Nunc. Naperville, Ill.; $5 \times 10^4$ cells/well) 1 day before addition of $1 \times 10^5$ apoptotic cells or cell-fee primary r cell tropic virus isolates (100 tissue culture 50% infectious dose). Dendritic cells were generated from PBMC by culture in human rIL-4 (450 U/ml; Genzyme, Cambridge, Mass.) and GM-CSF (250 ng/ml; Leucomax, Shering-Plough, Brinny, Ireland) as previously described (Sallusto, F., and A. Lanzavecchia. 1994. Efficient presentation of soluble antigen by cultured human dendritic cells is maintained by granulocyte/macrophage-colony stimulating factor plus interleukin 4 and downregulated by tumor necrosis factor. *J. Exp. Med.* 179:1109; Romani, N., D. Reider, M. Heuer S. Ebner, E. Kampgen, B. Eibl, D. Niederwieser, and G. Schuler. 1996. Generation of mature dendritic cells from human blood: an improved method with special regard to clinical applicability. *J. Immunol. Methods* 196:137; and Loré, K., A. Sönnerborg, A. L. Spetz, U. Andersson, and J. Andersson. 1998. Immnunocytochemical detection of cytokines and chemokines in Langerhans cells and in vitro derived dendritic cells. *J. Immunol. Methods* 218:173). Generated immature dendritic cells were used for cocultured experiments on day 6 or 7. Apoptotic cells ($5 \times 10^5$ dendritic cells/ml) were added to $3 \times 10^5$ dendritic cells/ml in a 24-well plate. The HIV-1 B3a-L isolate (500 tissue culture 50% infectious dose) (Gartner, S., P. Markovits, D. M. Markovitz, M. H. Kaplan, R. C. Gallo, and M. Popovic. 1986. The role of mononuclear phagocytes in HTLV-III/LAV infection. *Science* 233:215), HuT78$_{SF2}$ (Levy, J. A., A .D. Hoffman, S. M. Kramer, J. A. Landis, J. M Shimabukoro, and L. S. Oshiro. 1984. isolation of lymphocytopathic retroviruses from San Francisco patients with AIDS. *Science* 225:840), and 8E5/LAV RT$^-$ cells (Folks, T. M., D. Powell, M. Lightfoote, S. Koenig, A. S. Fauci, S. Benn, A. Rabson, D. Daugherty, H. E. Gendelman, M. D. Hoggan, et al. 1986. Biological and biochemical characterization of a cloned Leu-3⁻ cell surviving infection with the acquired immune deficiency syndrome retrovirus, *J. Exp. Med.* 164:280) were obtained through the AIDS Research and Reference Reagent Program, National Institutes of Health (McKesson BioServices, Rockville, Md.), and HuT78 cells were obtained from American Type Culture Collection (Manassas, Va.)

PBMC from HIV-1-infected patients or HIV-1-seronegative blood donors were isolated from EDTA-blood by density centrifugation on Ficoll-Hypaque gradients (Pharmacia, Uppsala, Sweden). Plasma HIV-1 viremia was measured by a branch DNA assay (Chiron, Emeryville, Calif.). CD4 T cells counts were performed by routine clinical laboratory testing. Apoptosis was induced either by gamma irradiation (150 Gy) 1–3 h before addition to the cultures or by treatment with etoposide 16 $\mu$g/ml for 48 h.

Immunofluorescence:

Stainings were performed as previously described (Sander, B., J. Andersson, and U. Andersson 1991. Assessment of cytokines by immunofluorescence and the paraformaldehyde-saponin procedure. *Immunol. Rev.* 119:65). In brief, cells were washed with PBS before fixation in 3.7% paraformaldehyde in PBS for 10 min. To reduce nonspecific Ab binding, cells were first incubated with 2% FCS in Earle's balanced salt solution (Life Technologies) supplemented with 0.01 M HEPES buffer (Life Technologies). Cells were then permeabilized with 0.1% saponin dissolved in balanced salt solution to allow intracellular entrance of HIV-1-specific Abs. To prevent unspecific binding of secondary Abs, 1% goat serum (Dako, Glostrup, Denmark) was added during incubation with primary Abs. Primary Abs diluted in balanced salt solution-saponin were added and left to incubate for 45 min at 37° C. After several washes with balanced salt solution-saponin the secondary Ab and Hoechst 33258 (Sigma, Stockholm, Sweden) were added and left to incubate for 30 min at room temperature. Cells were examined in a Leica RXM microscope (Leica, Wetzlar, Germany). The following mouse mAbs were used: anti-p24 (KAL-1, IgG1, Dako), anti-gp120 (8835, IgG1, Chemicon, Temecula, Calif.), anti-CXCR4 (12G5, IgG2a, PharMingen, San Diego, Calif.), anti-CCR5 (2D7, IgG2a, PharMingen), anti-CD4 (IgG1, Becton Dickinson, San Diego, Calif.), and anti-vimentin (Dako). Secondary goat anti-mouse Abs were Oregon Green-conjugated anti-Ig (Molecular Probes, Eugene, Oreg.).

Quantification of cell HIV-1 DNA content:

Adherent cells (5–20×10⁴ cells/sample) were trypsinized and washed in PBS twice before fixation in Permeafix (Ortho Diagnostics, Raritan, N.J.), Dendritic cells (1×10⁵ cells/sample) were washed in PBS and thereafter stored in Permeafix. HIV-1 gag DNA was detected by a fluorescent in situ 5'-nuclease assay (FISNA) (Patterson, B. K., Jiyampa, E. Mayrand, B. Hoff, R. Abrahamson, and P. M. Garcia. 1996. Detection of HIV-1 DNA in cells and tissue by fluorescent in situ 5'-nuclease assay (FISNA). *Nucleic Acids Res.* 24:3656:and Andersson, S., T. E. Fehniger, B. K. Patterson, J. Pottage, M. Agnoli, P. Jones, H. Behbahani, and A. Landay. 1998. Early reduction of immune activation in lymphoid tissue following highly active HIV therapy. *AIDS* 12:F123). The PCR was performed in cell suspension (1× PCR buffer II; 0.35 mM MgCl$_2$; 200 $\mu$M each of dATP, dCTP, dGTP, and dTTP; 200 $\mu$M each of gag primers SK38/SK39, sequences 5'-ATAATCCACCT ATCCCAGTAGGAGAAAT-3' and 5'-TTTGGTCCTTGTCTTATGTCCAGAATGC-3', and 100 nM of gag probe FTSK19 (FAM served as the reporter dye and TAMRA served as the quenching dye), sequence 5'-ATOCTGGATTAAATAAAATAGTAAGAATGTATAG CCCTAC-3' (10UAmpli-Taq DNA Polymerase IS) using the Gene Amp PCR System 2400 (PE Applied Biosystems, Foster City, Calif.). Reaction tubes were heated to 95° C. for 5 min followed by 30 cycles consisting of 94° C. for 45 s and 56° C. for 2 min, followed by a 15° C. soak. The cells were thereafter washed in PBS and put on slides by cytospin. Autofluorescence was quenched by incubation with trypan blue. The cells were evaluated for the presence of HIV-1 gag DNA at the single-cell level by an ACAS 570 laser confocal microscope (Insight Biomedical, Manchester, N.H.). The frequencies were manually counted. The cut-off values were determined based on fluorescence emitted from noninfected cells.

Quantitative kinetic, RT-PCR

RNA was purified from fibroblasts cocultured with apoptotic HUT78$_{SF2}$, 8E5/LAV RT⁻ or noninfected HuT78 cells for 1 or 2 wk as well as adherent PBMC (macrophages) cultured in RPMI-10% FCS for 1 wk, by Trizol reagent (Life Technologies) according to the manufacturer's protocol. RNA pellets were resuspended in 1× transcription buffer (Promega, Madison, Wis.) with 2 U RQ1 RNase-free DNase (Promega) and incubated for 30 min at 37° C. to remove contaminating DNA. The mixture was extracted once with phenol/chloroform/isoamyl alcohol and once with chloroform/isoamyl alcohol. The aqueous layer was removed, and the RNA was precipitated in 3 vol of ethanol and ¹⁄₄₀ vol of 3 mol/l, sodium acetate overnight at −20° C. Quantitative kinetic RT-PCR (Patterson, B. K., Landay, J. Andersson, C. Brown, H. Behbahani, D. Kiyampa, Z. Burki, D. Stanislawski, M. A. Czemiewski, and P. Garcia, P. 1998. Repertoire of chemokine receptor expression in the female genital tract: implication for human immunodeficiency virus transmission. *Am. J. Pathol.* 153:481) was performed by adding 45 $\mu$l of reaction mix (1× RT Taqman EZ buffer (PE Applied Biosystems, Foster City, Calif.), 4.0 mmol/L Mn(O) Ac$_2$, 300 $\mu$mol/L dATP, 300 $\mu$mol/L dCTP, 300 $\mu$mol/L dGTP, 300 $\mu$mol/L dTTP, 200 nmol/L upstream primer, 200 mol/L downstream primer, 200 nmol/L internally conserved fluorogenic probes, and 10 U of TTH polymerase) directly to 100 ng of total RNA in 5 $\mu$l of Rnase- and DNasefree water (Ambion, Austin, Tex.). Input RNA was normalized using glyceraldehyde-3-phosphate dehydrogenase mRNA quantification (PE Applied Biosystems). RT and thermal amplification were performed using the following linked profile: RT, 30 min at 60° C; cDNA denaturation, 5 min at 95° C., 40 cycles of denaturation (95° C. for 15 s); and annealing/extension, 60° C. for 1 min in a 7700 sequence detection system (PE Applied Biosystems). Duplicate standard curves with copy number controls ranging from 10 to 10⁵ copies were run with each optical 96-well plate (PE Applied Biosystems). In addition, no template controls were included. with each plate The primers and their respective probes were previously described (Patterson, B. K., Landay, S. Andersson, C. Brown, H. Behbahani, D. Kiyampa, Z. Burki, D. Stanislawski, M. A. Czemiewski, and P. Garcia, P. 1998. Repertoire of chemokine receptor expression in the female genital tract :implication for human immunodeficiency virus transmission. *Am. J. Pathol.* 153:481).

Lenti-RT activity assay:

Culture supernatants from dense cultures with 8E5/LAV RT⁻, HuT78$_{SF2}$, and noninfected HuT78 cells were tested for the presence of RT using a sensitive Lenti-RT activity assay (Cavidi Tech, Uppsala, Sweden) according to the manufacturer's protocol.

Flow cytometry:

Irradiated or etoposide-treated PBMC, HuT78, or 8E5/LAV RT− cells were stained with annexin V-FITC (Boehringer Mannheim, Mannheim, Germany) and propidium iodide (PI) according to the manufacturer's protocol. Early apoptosis was defined by annexin $V^+PI^-$ staining as determined by FACScan or FACSCalibur (Becton Dickinson). The kinetics of cell death after irradiation (2, 4, 10, 18, 24, 48 h) or etoposide treatment (12, 24, 48 h) were studied in noninfected cells, since HIV-1-infected cells were always fixed in paraformaldehyde before analyses by flow cytometry. Fluorescence intensity was measured using a $log_{10}$ scale, and 10,000 events were analyzed per sample.

RESULTS EXAMPLE 2

Transfer of HIM-1 DNA to fibroblasts:

Human fetal fibroblasts that lacked detectable mRNA and protein expression of CD4, CCR5, and CXCR4, as shown by immunofluorescent stainings and quantitative kinetic RT-PCR (Table 4 and data not shown), were used to study HIV-1 receptor-independent transfer of HIV-1. Freshly isolated PBMC or HuT78 cells were used as positive controls for inmmunofluorescent stainings of CD4, CCR5, and CXCR4, while macrophages (adherent PBMC cultured for 1 wk) were used as a positive control for the expression of CCR5 and CXCR4 mRNA (Table 4). To investigate whether HIV-1 DNA could be transferred by the uptake of apoptotic bodies in coculture experiments, HIV-1-infected and noninfected T cell lymphomas as well as PBMC were induced to undergo apoptosis before addition to fibroblast cultures. Apoptisis, as detected by annexin V binding was induced by either gamma irradiation (150 Gy) or treatment with etoposide (FIG. 5). Freshly isolated PBMC contained some debris and dead cells that were annexin $V^+PI^-$ and a few cells bound annexin V but did not take up PI (FIG. 5A). HIV-1-infected T cell lymphomas contained about 10–20% annexin-$V^-$ debris and cells before induction of apoptopsis (FIG. 5B). Almost all HIV-1-infected T lymphomas (FIGS. 5, D and F) and around 50% of PBMC (FIGS. 5, C and E) bound annexin V after 48 h of etoposide treatment or 18–24 h after irradiation. Approximately 15–20% of PBMC also took up PI, a sign of secondary necrosis. Fibroblasts were cocultured with apoptotic $HIV_{SF2}$-infected or noninfected HuT78 cells, and the first analyses were performed after 2 wk of culture. The presence of HIV-1 DNA after uptake of apoptotic bodies was detected using FISNA (Patterson, B. K., Jiyampa, E. Mayrand, B. Hoff, R. Abrahamson, and P. M. Garcia. 1996. Detection of HIV-1 DNA in cells and tissue by fluorescent in situ 5'-nuclease assay (FISNA). *Nucleic Acids Res.* 24:3656). Evaluation showed that fibroblasts cocultured with apoptotic $HuT78_{SF2}$ cells contained intracellular localized HIV-1 gag DNA, which remained throughout the culture period of 8 wk. However, fibroblasts cocultured with a cell-free primary T cell-tropic virus isolate or apoptotic noninfected HuT78 cells showed no presence of HIV-1 gag DNA (FIG. 6a and Table 5). An immortalized human endothelial cell line was analyzed following coculture with apoptotic $HUT78_{SF2}$ cells in parallel with fibroblasts, but did not show any gag DNA-positive cells. The endothelial cells thus served as a negative control for fibroblast cocultures analyzed by FISNA (Table 5).

To verify whether the presence of gag DNA in fibroblasts was due to transfer of HIV-1 DNA and not to uptake of free viruses released from apoptotic $HUT78_{SF2}$ cells, cocultures with apoptotic bodies derived from a T lymphoma infected with a defective virus were analyzed. 8E5/LAV RT− cells contain one integrated copy of an HIV-1 strain that lacks RT and consequently cannot produce complete viral particles, but can produce some HIV-1-encoded protein (Folks, T. M., Powell, M. Lightfoote, S. Koenig, A. S. Fauci, S. Benn, A. Rabson, D. Daugherty, H. E. Gendelman, M. D. Hoggan, et al 1986. Biological and biochemical characterization of a cloned Leu-3− cell surviving infection with the acquired immune deficiency syndrome retrovirus. *J. Exp. Med.* 164:280). Culture supernatants from 8E5/LAV RT− cells were analyzed by a sensitive RT assay at several time points to assure that the cells lacked RT (data not shown). Fibroblasts cocultured up to 8 wk with apoptotic bodies from 8E5/LAV RT− cells contained gag DNA, showing that the intracellular presence of HIV-1 DNA was not due to infection with viral particles derived from the apoptotic T lymphomas (FIG. 6a).

To exclude that HIV-1 detected in fibroblasts were due to remaining apoptotic bodies, the expressions of CXCR4 and CCR5 mRNA, originating from HuT78 cells, were followed by quantitative kinetic RT-PCR. Fibroblasts that were cocultured with apoptotic 8E5/LAV RT−, $HuT78_{SF2}$, or noninfected HuT78 cells for 1 wk had detectable CCR5 and CXCR4 mRNA expression as assessed by quantitative kinetic RT-PCR. Apoptotic bodies were also detected by Hoechst staining in the cytoplasm of fibroblasts after 1 wk of cocultivation with apoptotic HuT78 or 8E5/LAV RT− cells (See Example 1 above) After 2 wk of coculture, however, no remaining apoptotic bodies were found in the fibroblasts as detected by either Hoechst staining or quantitative kinetic RT-PCR (Table 4).

TABLE 4

Human fetal lung fibroblasts lack expression of CCR5 and CXCR4 mRNA

|  | CCR5 mRNA[a] | | CXCR4 mRNA[a] | |
| --- | --- | --- | --- | --- |
|  | Mean | SD | Mean | SD |
| One week of coculture | | | | |
| Fibroblast + apoptotic 8E5/LAV RT− | 0 | 0 | 3 | 1 |
| Fibroblast + apoptotic $HuT78_{SF2}$ | 0.1 | 0.2 | 71 | 24 |
| Fibroblast + apoptotic noninfected HuT78 | 0.2 | 0.2 | 247 | 51 |
| Two weeks of coculture | | | | |
| Fibroblast + apoptitic 8E5/LAV RT− | 0 | 0 | 0 | 0 |
| Fibroblast + apoptotic $HUT78_{SF2}$ | 0 | 0 | 0 | 0 |
| Fibroblast + apoptotic noninfected HuT78 | 0 | 0 | 0 | 0 |
| Macrophages[b] | 66 | 13 | 1966 | 537 |

[a]Human fetal lung fibroblasts were transferred to Lab-Tek chamber slides ($5 \times 10^4$ cells/well) before addition of apoptotic ($1 \times 10^5$ cells/well) 8E5/LAV RT− T cells infected with a defective RT− HIV-1 isolate, or apoptotic HIV-1-infected $HuT78_{SF2}$ T cells or apoptotic noninfected HuT78 T cells. After 1 or 2 wk of coculture, chemokine receptor nRNA was quantified by RT-PCR. Values (mean and SD from duplicates) equal number of chemokine receptor mRNA copies per 10,000 G3PDH mRNA copies.
[b]PBMC were cultured for 1 wk. The recovered adherent cells were analyzed for CCR5 and CXCR4 expression and used as positive control.

HIV-1 p24 and gp120 detected in fibroblasts after uptake of apoptotic bodies:

To investigate whether the transferred HIV-1 DNA was transcribed, fibroblasts were analyzed for protein expression of HIV-1 p24 and gp120 Ags. Immunofluorescent labelings showed expression of the HIV-1-encoded gene products p24 and gp120 in fibroblasts after 2 wk of coculture with apoptotic 8E5/LAV RT− and apoptotic $HuT78_{SF2}$ cells (FIG. 6b). The staining pattern was characterized by the accumulation of protein in the cytosol. Fibroblasts cocultured with noninfected HuT78 cells did not express p24 or gp120 as expected (FIG. 6b). The frequency of p24 Ag-positive fibroblasts after coculture with apoptotic 8E5/LAV RT⁻ and apoptotic HuT78$_{SF2}$ cells ranged between 0.3–1.7% in five independent experiments.

HIV-1-receptor-independent uptake of HIV DNA by dendritic cells,

Dendritic cells can present Ag derived from apoptotic cells, stimulating MHC class I-restricted Ag-specific CD8⁺ cytotoxic T cells (Albert, M. L., B. Sauter, and N. Bhardwaj. 1998. Dendritic cells acquire antigen from apoptotic cells and induce class 1-restricted CTLs. *Nature* 392:86). It was therefore investigated whether HIV-1 DNA could be transferred to dendritic cells by uptake of apoptotic bodies. Dendritic cells express HIV-1 receptors (Granelli-Piperno, A., B. Moser, M. Pope, D. Chen, Y. Wei, F. Isdell U. O'Doherty, W. Paxton, W. R. Koup, S. Mojsov, et al. 1996. Efficient interaction of HIV-1 with purified dendritic cells via multiple chemokine co-receptors. *J. Exp. Med.* 184:2433), an expression pattern that seems to be tightly regulated during dendritic cell maturation (Sallusto, F., P. Schaerli, P. Loetscher, C. Schaniel, D. Lenig, C. R. Mackay, S. Quin, and A. Lanzavecchia. 1998. Rapid and coordinated switch in chemokine receptor expression during dendritic cell maturation. *Eur. J. Immunol.* 28:2760). Apoptotic 8E5/LAV R⁻ T cells infected with the defective, RT-negative virus were therefore used in cocultures with dendritic cells. Dendritic cells were prepared from peripheral blood precursors of healthy donors by in vitro culture in the presence of rIL-4 and GM-CSF (Sallusto, F., and A. Lanzavecchia. 1994. Efficient presentation of soluble antigen by cultured human dendritic cells is maintained by granulocyte/macrophage-colony stimulating factor plus interleukin 4 and downregulated by tumor necrosis factor. *J. Exp. Med.* 179;1109; Romani, N., D. Reider, M. Heuer, S. Ebner, E. Kampgen, B. Eibl, D. Niederwieser, and G. Schuler, 1996. Generation of mature dendritic cells from human blood: an improved method with special regard to clinical applicability. *J. Immunol. Methods* 196:137; and Loré, K., A. S önnerborg, A. L. Spetz, U. Andersson, and J. Andersson. 1998. Immunocytochemical detection of cytokines and chemokines in Langerhans cells and in vitro derived dendritic cells. *J. Immunol. Methods* 218:173). Apoptotic 8E5/LAV RT⁻ cells were added to the in vitro differentiated dendritic cells after 6–7 days of culture. At this time dendritic cells were CD14⁻, HLA-DR⁺, CD83⁻, and CD86⁻ (Loré, K. Et al, 1998, supra), characteristic of an immature phenotype with phagocytosing capacity (Banchereau, J., and R. M.. Steinman. 1998. Dendritic cells and the control of immunity. *Nature* 392:245). HIV-1 gag DNA could be detected by FISNA in approximately 18% of dendritic cells after 2 wk of coculture with apoptotic 8E5/LAV RT⁻ cells and in 9% after infection with a cell-free macrophage-tropic Ba-L isolate (FIG. 7a and Table 5). Dendritic cells cocultured with noninfected cells or without any virus isolate did not emit positive signals for gag DNA. These results show that HIV-1 DNA can be transferred to dendritic cells by uptake of apoptotic bodies.

TABLE 5

Detection of HIV-1 DNA in cocultures by FISNA[a]

| Cocultures[b] | % HIV-1 DNA Containing cells | |
|---|---|---|
| | 2 wk coculture | 8 wk coculture |
| Fibroblast + apoptotic 8E5/LAV RT⁻ | 19 | 5.2 |
| Fibroblast + apoptotic HuT78$_{SF2}$ | 46 | 68 |
| Fibroblast + apoptotic noninfected HuT78 | 0.3 | 0.1 |
| Fibroblast + apoptotic PBMC HIV-1 infected donor | 51 | 7.1 |
| Fibroblast + apoptotic PBMC seronegative donor | 0.1 | 0.1 |
| Fibroblast + T cell tropic primary virus isolate | 0.1 | 0.6 |
| Dendritic cells + apoptotic 8E5/LAV RT⁻ | 18 | ND |
| Dendritic cells + apoptotic noninfected HuT78 | 0.1 | ND |
| Dendritic cells + Ba-L isolate | 8.9 | ND |
| Dendritic cells | 0.1 | ND |
| Endothelial apoptotic 8E5/LAV RT⁻ | 1.3 | 0.3 |
| Endothelial + apoptotic noninfected HuT78 | 0.1 | ND |
| Endothelial + apoptotic PBMC HIV-1 infector donor | 0.9 | 0.9 |
| Endothelial + apoptotic PBMC seronegative donor | 0.1 | 0.1 |
| Endothelial + T cell tropic primary virus isolate | 0.3 | 0.1 |

[a]HIV-1 DNA was detected by FISNA (Patterson, B. K., Jiyampa, E. Mayrand, B. Hoff; R. Abrahamson, and P. M. Garcia. 1996. Detection of HIV-1 DNA in cells and tissue by fluorescent in situ 5'-nuclease assay (FISNA). Nucleic Acids Res. 24:3656. The cells were evaluated for presence of HIV-1 DNA at the single cell level by an ACAS 570 laser confocal microscope. Values above 1.5% are considered positive. One representative experiment of at least two is shown.
[b]Human fetal lung fibroblasts and human endothelial cells were transferred to Lab-Tek chamber slides (5 × 10⁴ /well) 1 day before addition of indicated apoptotic cells (1 × 10⁵ cells/well) or cell-free virus isolates 100 TCID$_{50}$. Dendritic cells were generated from PBMC from blood donors by culture in medium containing human rIL-4 and GM-CSF. Generated immature dendritic cells were used for coculture experiments at day 6 or 7. Apoptotic cells (5 × 10⁵ cells/ml) were added to 3 × 10⁵ dendritic cells/ml. HIV-infected HuT78$_{SF2}$ (Levy, J. A., A. D. Hoffman, S. M. Kramer, J. A. Landis, J. M. Shimabukoro, and L. S. Oshiro. 1984. Isolation of lymphocytopathic retroviruses from San Francisco patients with AIDS. Science 225:840), noninfected HuT78, 8E5/LAV RT⁻ cells (Folks, T. M., D. Powell, M. Lightfoote, S. Koenig, A. S. Fauci, S. Benn, A. Rabson, D. Daugherty, H. E. Gendelman, M. D. Hoggan, et al. 1986. Biological and biochemical characterization of a cloned Leu-3⁻ cell surviving infection with the aquired immune deficiency syndrome retrovirus. J. Exp. Med. 164:280), and PBMC isolated from HIV-1 infected patients or healthy blood donors, were irradiated 150 Gy, before addition to the cultures.

Transfer of HIV DNA by apoltotic HIV-1-infected PBMC:

PBMC from HIV-1-infected patients contain cells that are latently infected and in which the viral cDNA is integrated within host cell DNA (Stevenson, M. 1997. Molecular mechanisms for the regulation of HIV replication, persistence and latency. *AIDS* 11:S25). To assess whether PBMC isolated from HIV-1-infected patients could transfer HIV-1 by uptake of apoptotic bodies, fibroblasts were cocultured with apoptotic PBMC isolated from HIV-1-infected patients. PBMC were isolated from five patients with HIV RNA levels of <2.7–6.5 log$_{10}$ copies/ml of plasma and CD4 cell counts between 25–220/mm³. Fibroblasts cocultured with apoptotic bodies derived from PBMC isolated from HIV-1-infected donors contained gag DNA after 2–8 wk of culture at a frequency of 6–51% (FIG. 7c and Table 5). Freshly isolated PBMC (from the same HIV-1-infected patients) that had not been induced to undergo apoptosis by irradiation as well as apoptotic PBMC from HIV-1 seronegative donors did not transfer HIV-1 DNA to cocultured fibroblasts (FIG. 7c and Table 5).

Fibroblasts cocultured with apoptotic PBMC isolated from HIV-1-infected patients also expressed the HIV-1 Ag p24 (FIG. 7b). The frequencey of intracellular p24 Ag-positive fibroblasts detected by immunofluorescence after 2 wk of coculture with apoptotic PBMC isolated from HIV-1-infected patients ranged between 0.6–2.7%, thus similar to the frequency detected in cocultures with apoptotic 8E5/LAV RT⁻ and apoptotic HuT78$_{SF2}$ cells (0.3–1.7%).

EXAMPLE 3: Horizontal transfer of oncogenes by uptake of apoptotic bodies

Methods

Cell culture:

Rat embryonic fibroblasts (REF), mouse embryonic fibroblasts (MEF) and MEF p53$^{-/-}$ (Donehower, L. A., Harvey, M., Slagle, B. L., McArthur, M. J., Montgomery, C. A. J., Butel, J. S. & Bradley, A. (1992) *Nature* 356, 215–221) were isolated as described (Spector, D. L., Goldman, R. D. & Leinwand, L. A. (1997) *Cells: a laboratory manual.* (Cold Spring Harbor Laboratory Press, Plainview N.Y.) and grown in Dulbecco's Modified Eagle's Medium (DMEM, Hyclone) with 10% foetal bovine serum (Hyclone), glutamine and penicillin/streptomycin. REFrm cells are REF cells transfected with H-ras$^{V12}$, human c-myc (kindly provided by Dr R. N. Eisenman) and a hygromycin resistance gene fused with green fluorescence protein (pEGFP-hyg, Clontech). For co-culture experiments, 2×10⁶ MEF or MEF p53$^{-/-}$ cells were trypsinised and transferred to 10-cm Petri dishes. Apoptosis was induced in 10×10⁶ REFrm and REF non-transfected cells by irradiation (150 Gy) or by nutrient depletion for 24 h. Irradiated or nutrient depleted cells were incubated with MEF or MEF p53$^{-/-}$ cells at a ratio of 5:1 for the time points indicated in the figure legends. The tissue culture media were changed after 48 hours and then changed every three days. Focus formation was recorded by microscopy after eight days in culture as previously described (Shih, C., Shilo, B. Z., Goldfarb, M. P., Dannenberg, A. & Weinberg, R. A. (1979) *Proc Natl Acad Sci USA*. 11, 5714–5718).

Apoptosis detection:

DNA fragmentation was analyzed as described (Holmgren, L., Szeles, A., Rajnavölgyi, E., Klein, G., Folkman, J., Ernebrg, I. & Falk, K. (1999) *Blood* 93, 3956–63). The morphology of apoptotic nuclei was detected by Hoechst 33258 (Sigma) staining.

PCR analysis and immunoblotting:

DNA was isolated using the Qiaamp Blood Kit (Qiagen) and PCR analysis were performed with specific primers for H-ras$^{V12}$ (5'-ggcaggagacectgtaggag-3', 3'-gtattcgtccacaaaatggttct-5'), human c-myc (5'-gaggctattctgcccatttg-3',3'-cagcagetcgaatttcttcc-5') and hyg$^r$ (5 '-acgtaaacggccacaagttc -3,3'-aagtcgtgctgcttcatgtg -5). Conditions for PCR amplification were as follows: H-ras$^{V12}$: 30 sec. 95° C., 45 sec. 61° C., 2 min. 72° C., 30 cycles, human c-myc and hyg$^r$:30 sec. 95° C., 45 sec. 58° C. 2 min. 72° C. for 30 cycles. For immunoprecipitation and western blot analysis, 3×10⁷ cells were lysed in RIPA buffer (10 mM Tris-HCl pH 7.4, 150 mM NaCl, 1% NP40, 1% DOC, 0,1% SDS, 0,5% aprotinin) at +4° C. for 10 minutes. After sonication (Soniprep 150, Labassco) for 30 s at 50 Watt, cells were centrifuged for 15 minutes, 3000 rpm, at +4° C., The supernatant was incubated with antibody for 1 hour at +4° C. (H-ras$^{V12}$ R02120, Transduction Laboratories; c-myc (N-262) sc-764, Santa Cruz Biotech. Inc.), 35 µl ImmunoPure® Immobilised Protein C; (20398, Pierce) was added to each sample and incubated overnight at +4° C. The precipitates were centrifuge for 5 minutes, 2500 rpm and washed three times in lysis buffer. Immunoprecipitates were analyzed by SDS PAGE and western blot analysis as previously described (Henriksson, M., Bakardjiev, A., Klein, G. & Lüscher, B. (1993) *Oncogene* 8, 3199–3209). Filters were blocked with 5% milk (BioRad Non-fat dry milk, 170–6404) for 1 hour at RT, the membrane was incubated with the primary antibody (pan-H-Ras$^{V12}$ Val-12, OP38, Oncogene Research Products; c-Myc (9E10) , Santa Cruz Biotech) overnight at 4° C. After washing with 0,2% Tween20 in PBS the membrane was incubated with an anti-mouse horseradish peroxidase conjugated secondary antibody (NA 931, Amersham Pharmacia, Life Science) for 2 hours at RT. The membrane was developed using the ECL detection system according to the protocol of the manufacturer (RPN2209, Amersham Pharmacia Biotech.).

Tumorigenicity assays:

Immunodeficient SCID mice were maintained in a pathogen-free environment. Approximately 4×10⁶ MEF p53$^{-/-}$ cells cultivated with either apoptotic REF or REFrm cells were injected into the dorsal subcutaneous space of 6–7 weeks old SCID mice. Injection of MEF p53$^{-/-}$ cells and REFrm cells served as negative and positive controls.

FISH and GFP analysis:

Interphase nuclei and metaphase chromosomes were analyzed on standard cytogenetic preparations, as previously described (Szeles, A., Bajalica-Lagercrantz, S., Lindblom, A., Lushnikova, T., Kashuba, V. I., Imreh, S., Nordenskjold, M., Klein, G. & Zabarovsky, E. (1996) *Chromosome Res.* 4, 310–313). The rat genomic DNA was labeled by nick translation with biotinylated- 16-dUTP (Boehringer Mannheim) using the BIONICK labeling kit (GIBCO-BRL). The human c-myc DNA probe was labeled with Spectrum Orange (Vysis). Hybridization was performed in 50% formamide, 2×SSC, and 10% dextran sulphate at 37° C. overnight as described (Szeles, A., Bajalica-Lagercrantz, S., Lindblom, A., Lushnikova, T., Kashuba, V. I., Imreh, S., Nordenskjold, M., Klein, G. & Zabarovsky, E. (1996) *Chromosome Res.* 4, 310–313). Biotin signals were detected with fluorescein isothiocyanate (FITC)-avidin DCS (Vector Laboratories) and amplified with one layer of biotinylated anti-avidin antibody (Vector Laboratories), followed by one layer of FITC-avidin (Pinkel, D., Straume, T. & Gray, J. W. (1986) *Proc Natl Acad Sci USA* 83, 2934–2938). Chromosomes and nuclei were counterstained with di-aminophenyl-indole (DAPI). The slides were examined with a Leica DMRBE microscope equipped with a cooled CCD camera (Hamamatsu 4800) and filter sets specific for the fluorochromes (DAPI, FITC and Spectrum Orange). GFP staining was visualized as previously described (Cheng, L., Fu, J., Tsukumoto, A. & Hawley, R. G. (1996) *Nature Biotech.* 14, 606–609).

RESULTS EXAMPLE 3

Tumor apoptotic bodies induce foci formation:

In the previous examples, it was shown that integrated viral genes maybe horizontally transferred via the uptake of DNA from apoptotic bodies. In this example, the question was raised of whether engulfment of apoptotic bodies derived from cells carrying oncogenes may cause transformation of the recipient cell. Wild type rat embryonic fibroblasts (REF) or REF cells co-transfected with the H-ras$^{V12}$ and human c-myc (REFrm) oncogenes were used as donor cells. Cell death was induced in REF or REFrm by irradiation or by nutrient depletion. Both methods induced ladder formation of DNA purified from the cytoplasmic fraction of the cell lysates (FIG. 10A). In addition, irradiation or nutrient depletion induced nuclear condensation, which is consistent with cell death by apoptosis (FIG. 10B and data not shown). In example 1, it was shown that fibroblast cells are capable of ingesting apoptotic bodies by phagocytosis. Indeed, addition of apoptotic bodies to murine embryonic fibroblasts (MEF) resulted in rapid internalization (FIG. 10B).

Next, it was assessed whether horizontally transferred DNA from apoptotic bodies derived from REFrm cells could induce loss of contact inhibition in mouse embryonic fibroblasts. Apoptosis was induced as described and dying cells were cultured with wild type MEF. Focus formation could be detected in MEF cells cultured with irradiated REFrm cells (FIGS. 11A and B). However, these cells became senescent or died during propagation. The p53 tumor suppressor gene is considered as the guardian of the genome and is activated by DNA damage (Lane, D. P. (1992) *Nature* 358, 15–16, Levine, A. J. (1997) *Cell* 88, 323–331). In addition, transformation of primary rodent cells by the ras oncogene results in accumulation of the p53 protein resulting in permanent G1 arrest and senescence (Serrano, M., Lin, A. W., McCurrach, M. E., Beach, D. & Lowe, S. W. (1997) *Cell* 88, 593–602). It was therefore tested whether inactivation of p53 would influence the frequency of focus formation and facilitate propagation of cells expressing oncogenic ras. Co-culture of the MEF p53$^{-/-}$ recipient cells with wild type REF apoptotic bodies did not result in detectable focus formation (FIG. 11A). However, numerous foci, growing as spheroids, were detected when REFrm apoptotic bodies were co-cultured with p53$^{-/-}$ cells (FIGS. 11A and B). The addition of necrotic REFrm cells did not induce any detectable foci in this assay. The cells derived from the REFrm× MEF p53$^{-/-}$ foci were harvested and could be propagated in vitro. Primers were generated against the transfected H-ras$^{V12}$ and c-myc genes. These primers did not detect the endogenous mouse or rat genes. PCR analysis showed that all foci were positive for PCR amplification with H-ras$^{V12}$ and human c-myc specific primers (FIGS. 11C and D). However, the positive signals gradually disappeared during culture and were lost in all clones after 4 weeks.

Positive selection pressure favors propagation of apoptotic DNA:

To test whether positive selection pressure would favor propagation of DNA engulfed by phagocytosis, it was studied whether uptake of apoptotic bodies would confer resistance to hygromycin drug selection. Apoptosis was induced in the REFrm cells transfected with the gene encoding hygromycin resistance fused to the enhanced green fluorescent marker (Hyg$^r$-EGFP) or in REF cells and the resulting apoptotic cells were incubated with either MEF or MEF p53$^{-/-}$ cells. Hygromycin selection was started after 48 h of culture and was maintained for 4 weeks. In three independent experiments, 90±15 resistant colonies per 10 cm Petri dish were scored in cultures with MEF p53$^{-/31}$ cells fed with REFrm apoptotic cells (FIG. 12A). No resistant colonies were detected in plates with MEF cells incubated with REF apoptotic bodies. PCR analysis showed that the hygromycin resistant colonies contained the Hyg$^r$ gene (FIG. 12B). In addition, colonies expressed the Hyg$^r$-EGFP fusion protein as detected by fluorescence microscopy (FIG. 12C). Approximately 60% of the foci derived from REFrmxMEF p53$^{-/-}$ co-culture contained the Hyg$^r$ gene which, in contrast to the H-ras$^{V12}$ and c-myc genes, could be maintained during culture in the presence of drug selection (FIG. 12D). Taken together, these data suggest that stable propagation of DNA derived from apoptotic cells is dependent on whether or not the encoded genes provide a positive selection advantage.

Oncogenic activity of apoptotic bodies:

The loss of H-ras$^{V12}$ and human c-myc DNA during cultivation of cells derived from REFrmxMEF p53$^{-/-}$ foci indicates that the selection pressure did not favor maintenance of the transferred oncogenes in vitro. In order to test whether transferred once genes could be propagated in vivo, REFrmxMEF p53$^{-/-}$ foci were injected into SCID mice, MEF or MEF p53$^{-/-}$ cells co-cultured with REF cells were used as negative controls. Tumors were formed within three weeks after injection of the cells derived from transformed foci, showing that a fully tumorigenic potential had developed, as shown in table 6 below.

TABLE 6

Formation of tumors in SCID mice

| Cells | Number of tumors/number of injections |
|---|---|
| REFrm x MEF p53-/- | 6/10 |
| REFxMEF p53-/- | 0/10 |
| REFrm | 20/20 |
| MEF p53-/- | 0/20 |

In table 6, tumor formation in SCID mice is shown. Focus forming cells derived from one 10 cm dish were injected subcutaneously into SCID mice. Negative controls included equal numbers of MEF p53$^{-/-}$ co-cultured with apoptotic REF or untreated MEF p53$^{-/-}$. Injection of 4×10$^6$ REFrm cells served as a positive control.

MEF p53$^{-/-}$ cells cultured with non-transformed REF cells did not induce tumor growth. Tumor cells were isolated from the mice and subjected to PCR analysis. The H-ras$^{V12}$ and c-myc DNA as well as the corresponding protein could be detected in all tumors analyzed (FIGS. 13A and B). After the in vivo passage the transferred oncogenes could then be propagated in vitro. This was shown by the fact that the peresence of transferred oncogenes in tumor-derived cells was stable for over three months in culture and maintained a tumorigenic potential when re-injected into mice (data not shown).

Next fluorescence in situ hybridization (FISH) analysis was used to investigate how the transferred DNA was propagated in the REFrmxp53$^{-/-}$ tumor cells. In order to follow the fate of the DNA internalized by phagocytosis, a probe was used which distinguished between the DNA of the donor cells from that of the recipient cells. Rat genomic DNA was labeled with biotinylated-16-dUTP and subsequently used to identify DNA derived from apoptotic bodies. This probe hybridized specifically to rat DNA interphase nuclei or metaphase chromosome spreads with no detectable cross hybridization to mouse DNA (FIG. 13C). Analysis of metaphase spreads from cells derived from REFrmxp53$^{-/-}$ tumors revealed the presence of rat chromosomes as well as hybrid rat/mouse chromosomes. In addition, FISH-analysis using a rhodamine-labeled probe specific for the human c-myc gene showed that human c-myc was present in all tumors analyzed (FIG. 13D).

Discussion

Example 3 reports for the first time that activated oncogenes are transferred in a horizontal manner by the uptake of apoptotic bodies. Uptake of apoptotic bodies derived from H-ras[12] and c-myc transfected cells induced loss of contact inhibition, anchorage independence as well as tumorigenicity in SCID mice after transfer to recipient p53$^{-/-}$ cells. In contrast, apoptotic bodies derived from normal REF cells did not affect the growth of the recipient cells in any of these assays. Furthermore, no transformation was detected when apoptotic bodies were cultured with mouse embryonic fibroblasts with intact p53 indicating that p53 may protect cells from incorporation of activated oncogenes derived from apoptotic bodies. There are several possible explanations why normal fibroblasts are not transformed by tumor apoptotic bodies. For example, phagocytosed apoptotic DNA may be identified by the cell as damaged DNA resulting in the accumulation of p53 protein that may induce either cell cycle arrest or apoptosis. Previous publications have shown that transfection of oncogenic ras in normal fibroblasts results in p53-mediated permanent G1 arrest. In addition, inactivation of p53 in cells in culture has been shown to be correlated with aneuploidy (26) which may explain why whole rat chromosomes are propagated in REFrm×MEF p53$^{-/-}$ tumours (FIG. 13C).

The present invention shows that the transferred DNA is lost unless it confers a strong selective advantage to the recipient cell. Interestingly, the H-ras$^{V12}$ and c-myc genes could not be maintained during continous propagation in vitro whereas the Hygr gene could be maintained for more than 4 months in the presence of hygromycin. This may reflect that the transferred DNA is inefficiently replicated in the new host or that there is no selection for these oncogenes in vitro. However, when these cells were injected into SCID mice all resulting mouse tumors expressed both H-ras$^{V12}$ and human c-myc. The size of the transferred DNA indicates that the entire genome is not fragmented under the conditions in which the experiments were performed. The fragmentation of DNA as shown in FIG. 10 represents only the soluble fraction of the total DNA and hence shows that only a fraction of the total DNA is fragmented. This is consistent with previous studies that have shown that nuclear condensation and apoptosis are independent of DNA degradation (Oberhammer, F., Fritsch, G., Schmied, M., Pavelka, M., Printz, D., Purchio, T., Lassmann, H. & Schulte-Hermann, R. (1993) *J. Cell. Sci.* 104, 317–326, Nagata, S. (2000) *Exp Cell Res.* 256, 12–18).

Cancer is a genetic disease that requires the accumulation of genetic alterations that are necessary for malignancy (Bishop, J. M. (1991) *Cell* 64, 235–248, Hanahan, D. & Weinberg, R. A. (2000) *Cell* 100, 57–70). Most tumor cells are genetically unstable as manifested by the genomic heterogeneity between cells within the tumor. This genetic instability may accelerate tumor progression by promoting mutations that confer a growth advantage. The increase in mutation frequency in cancer cells may be explained by the inactivation of genes involved in maintaining the integrity of the genome. These include the p53 tumor suppressor gene, the mismatch repair genes and genes involved in controlling the replication and segregation of chromosomes during mitosis (Jackson, A. L. & Loeb, L. A. (1998) *Seminars in Cancer Biology* 8, 421–429). The present invention proposes that the uptake of DNA via apoptotic bodies may be one possible mechanism by which genetic instability and genetic diversity is generated within a tumor.

EXAMPLE 4: Induction of immune responses by dendritic cells after uptake of apoptotic HIV-1 infected cells Materials and Methods Cell cultures PBMCs from HIV-1 sero-negative blood donors were isolated from EDTA-blood by density centrifugation on Ficoll hypaque gradients (Pharmacia, Uppsala, Sweden). DCs (Dendritic Cells) were derived from adherent monocytes by culture in media (RPMI 1640 with 2 mM L-glutamine, Gibco, Paisley, UK, 10% FCS, Gibco, 1% streptomycin and penicillin, Gibco) supplemented with human recombinant IL-4 (450 U/ml, R&D Systems, Minneapolis, Mass.) and GM-CSF (250 ng/ml, Leucomax, Shering-Plough, Brinny, Ireland) as described (Romani, N., S. Gruner, D. Brang, E. Kampgen, A. Lenz, B. Trockenbacher, G. Konwalinka, P. O. Fritsch, R. M. Steinman, and G. Schuler. 1994. Proliferating dendritic cell progenitors in human blood. *J Exp Med* 180:83; Sallusto, F., and A. Lanzavecchia. 1994. Efficient presentation of soluble antigen by cultured human dendritic cells is maintained by granulocyte/macrophage colony-stimulating factor plus interleukin 4 and downregulated by tumor necrosis factor alpha. *J Exp Med* 179:,1109; and Lore, K., A. Sonnerborg, A. L. Spetz, U. Andersson, and J. Andersson. 1998.) Immunocytochemical detection of cytokines and chemokines in Langerhans cells and in vitro derived dendritic cells". *J Immunol Methods* 218:173. Immature CD14$^-$, CD1a$^+$, CD80$^{low}$, and CD86$^{low}$ DCs were used for co-culture experiments after 6–7 days of differentiation. The HuT78$_{SF2}$ lymphoma T cell line (Levy, J. A., A. D. Hoffman, S. M. Kramer, J. A. Landis, J. M. Shimabukuro, and L. S. Oshiro. 1984. Isolation of lymphocytopathic retroviruses from San Francisco patients wit AIDS. *Science* 225:840) and the 8E5$_{LAV}$ RT$^-$ lymphoma T cell line (Folks, T. M., D. Powell, M. Lightfoote, S. Koenig, A. S. Fauci, S. Benn, A. Rabson, D. Daugherty, H. E. Gendelman, M. D. Hoggan, and et al. 1986. Biological and biochemical characterization of a cloned Leu-3- cell surviving infection with the acquired immune deficiency syndrome retrovirus. *J Exp Med* 164:280) were obtained through the AIDS Research and Reference Reagent Program, NIH, (McKesson BioServices, Rockville, Md.) and the HuT78 lymphoma T cell line from the American Type Culture Collection (ATCC, Rockville, Md.). Apoptosis of the lymphoma cell lines was induced by γ-irradiation (150 Gy). Early apoptosis was defined by annexin V$^+$ propidium iodide staining and evaluated by flow cytometry analysis as previously described (Holmgren, L., A. Szeles, B. Rajnavolgyi, J. Folkman, G. Klein, I. Ernberg, and K. I. Falk. 1999. Horizontal transfer of DNA by the uptake of apoptotic bodies [see comments]. *Blood* 93:3956; Spetz, A. L., B. K. Patterson, K. Lore, J. Andersson, and L. Holmgren. 1999. Functional gene transfer of HIV DNA by an HIV receptor-independent mechanism. *J Immunol* 163:736). Apoptotic cells were added to 2-5×10$^5$ DCs/ml at a ratio of 1:1 in 24 well plates (Costar corp., New York, N.Y.). DCs were exposed to the cell free HIV-1 Ba-L isolate (obtained after centrifugation of infectious cell culture supernatants) using 32 TCID$_{50}$ (Tissue Culture Infectious Dose$_{50}$) in each experiment (Gartner, S., P. Markovits, D. M. Markovitz, M. H. Kaplan, R. C. Gallo, and M. Popovic. 1986. The role of mononuclear phagocytes in HTLV-II/LAV infection. *Science* 233:215). After 5–7 days of co-culture the DCs were washed and titrated (0.1–4×10$^4$ DCs/well) into 96 well plates (Costar corp.) before addition of newly thawed or freshly isolated autologous PBMCs (1×10$^5$ cells/well). In order to induce further maturation of DCs a small amount of LPS (50 ng/ml, purified from *E. coli* BR 055:35, Dept. of Bacteriology, Karolinska institute, Stockholm, Sweden) was added to the culture medium 3 days prior to addition of the PBMCs.

Phagocytosis assay

HuT78 or HuT78$_{SF2}$ cells were stained with PKH26-GL, a red fluorescent linker, according to the manufacturer's protocol (Sigma, St. Louis, Mo.) and apoptosis was subsequently induced by γ-irradiation. After 2 h of incubation with apoptotic cells, DCs were harvested, stained with FITC conjugated anti-CD1a (DAKO, Glostrup, Denmark) followed by analysis using a FACS Calibur flow cytometer (Becton Dickinson, San Jose, Calif.). The frequency of double positive cells was used to quantify the efficiency of phagocytosis.

Immunofluorescence analysis of p24 expression:

Staining was performed as previously described (see example 2 above) in order to analyze intracellular HIV-1 p24 protein expression in DCs after uptake of apoptotic bodies or exposure to the cell free HIV-1 Ba-L isolate. In brief, DCs from the different co-cultures were transferred to adhesion slides (BioRad Lab, Munich, Germany) and fixed in buffered 3.7% formaldehyde (Sigma, St. Louis, Mo.). Cells were permeabilized with 0.1% saponin (Riedel-de Haen AG, Seelze, Germany) dissolved in PBS followed by incubation with the intracellular HIV-1 specific anti-p24 antibodies (KAL-1, IgG1, DAKO or FITC conjugated KC 57, (Coulter Corp., Miami, Fla.). The secondary FITC conjugated goat anti-mouse Ig Fab'2 (DAKO) was then applied. The cells were mounted and examined in a Leica RXM microscope (Leica, Wetzlar, Germany) or analyzed by flow cytometry using a FACS Calibur (Becton Dickinson, San Jose, Calif.).

Proliferation assay:

PBMC proliferation was measured in the DC-PBMC cultures by adding 1 μCi/well $^3$H-thymidine (specific activity 6.7 Ci/mmol, DuPont, Wilmington, Del.) for 6–9 h 2–7 days after adding the autologous PBMCs. PBMCs stimulated with PHA (2.5 μg/ml, Sigma) were used as positive controls. DCs and PBMCs grown in medium only were used to reveal background proliferation values. Liquid scintillation counting was used to reveal the cpm.

Immunocytochemical detection of intracellular IFN-γ expression:

After 6–7 days of culture with DCs exposed to LPS, the PBMCs (and remaining DCs) were harvested, put on adhesion slides and fixed in formaldehyde. The staining procedure has been previously described (Lore, K., A. Sonnerborg, A. L. Spetz, U. Andersson, and J. Andersson. 1998. Immunocytochemical detection of cytokines and chemokines in Langerhans cells and in vitro derived dendritic cells". *J Immunol Methods* 218:173; Sander, B., J. Andersson, and U. Andersson. 1991. Assessment of cytokines by immunofluorescence and the paraformaldehyde-saponin procedure. *Immunol Rev* 119:65), and all steps were performed in 0.1% saponin dissolved in 1× Earl's balanced salt solution (Gibco). The cells were incubated with the biotinylated anti-IFN-γ antibody (7B6-1, Mabtech AB, Nacka, Sweden) followed by incubation with an avidin-biotin horseradish peroxidase complex (Vectastain, Vector Laboratories Inc., Burlinggame, Calif.). A brown color reaction was developed by 3'-diaminobenzidine tetrahydrochloride (Vector Laboratories Inc.). The cells were counterstained with hematoxylin and the slides were mounted in buffered glycerol. Digital images of stained samples were transferred from a DMR-X microscope (Leica), into a computerised image analysis system, Quantimet 5501W (Leica, Cambridge, UK). Quantification of IFN-γ was achieved by marking the positive and negative cells manually in the digital image, which were then counted by a specialized in situ imaging computer program. The evaluation was performed on at least 500 cells per sample.

ELISA for assessment of IFN-γ production:

The IFN-γ that was released into the supernatants of the DC-PBMC cultures was measured using the Quantikine ELISA kit (R&D Systems) according to the manufacturer's instructions.

Flow cytometry for cell surface expression:

Expression of MHC class II (HLA-DR) and the co-stimulatory molecules CD86 and CD80 was detected by flow cytometry as previously described (Lore, K., A. Sonnerborg, J. Olsson, B. K. Patterson, T. P. Fehniger, L. Perbeck, and J. Andersson. 1999. HIV-1 exposed dendritic cells show increased pro-inflammatory cytokine production but reduced IL-1ra following lipopolysaccharide stimulation *Aids* 13:2013; Lore, K., A. Spetz, T. E. Fehniger, A. Sonnerborg, A. L. Landay, and J. Andersson. 2001. Quantitative single cell methods that identify cytokine and chemokine expression in dendritic cells, *J Immunol Methods* 249:207). The DCs co-cultured for 6–7 days in the presence or absence of LPS were harvested and washed in PBS and blocked with 10% human AB-serum. The cells were then exposed to the antigen specific mAbs; PerCP-conjugated anti-HLA-DR (Becton Dickinson), PE-labelled anti-CD86 (Becton Dickinson), and FITC-labelled anti-CD80 (PharMingen, San Diego, Calif.) at 4° C. for 30 min. After washes, the cell surface expression was assessed by a FACS Calibur flow cytometer. Analyses were performed with at least 20,000 cells per sample. The results presented as the log of the fluorescence intensity values.

Statistical Analysis:

Statistical significance was assessed by the Wilcoxon's paired t-test and considered significant at a two-tailed p-value of <0.05.

RESULTS EXAMPLE 4

DCs engulf HIV-1 infected apoptotic cells:

The HIV-1 tat antigen has previously been shown to inhibit phagocytosis of apoptotic bodies (reviewed in (Rubartelli, A., A. Poggi, R. Sitia, and M. R. Zocchi. 1998. HIV-I Tat: a polypeptide for all seasons. *Immunol Today* 19:543). To investigate whether uptake of HIV-1 infected apoptotic bodies can occur in the absence of free HIV-1 virions, the HIV-1 infected lymphoma T cell line HuT78$_{SF2}$ or the equivalent non-infected HuT78 lymphoma T cell line were labeled with the red fluorescent linker PKH26-GL. The cells were induced to undergo apoptosis and after 16 h the apoptotic cells were fed to in vitro differentiated immature DCs. The DCs were stained with anti-CD1a-FITC and analyzed by flow cytometry. Numerous DCs (20–50%) were found to have internalized apoptotic cells after 2 h of incubation (FIGS. 15a–b). There were no quantitative differences in the uptake of apoptotic non-infected (HuT78) or HIV-1 infected (HuT78$_{SF2}$) cells by the DCs (FIGS. 15a–b).

DCs express HIV-1 p24 after engulfing HIV-1 containing apoptotic cells;

Immunofluorescence was used to visualize HIV-1 p24 protein expression in DCs after 7–10 days of co-culture (FIGS. 15c–f). The HIV-1 p24 protein was detected in DCs co-cultured with apoptotic bodies obtained from the lymphoma T cell line HUT78$_{SF2}$, infected with complete HIV-1, (FIG. 15c) and 8E5$_{LAV}$RT$^-$, which contains an integrated HIV-1 genome with a deletion of the RT (Reverse Transcriptase) gene (FIG. 15d). The 8E5$_{LAV}$RT$^-$ cells do not produce infectious virions and thus direct receptor dependent HIV-1 infection of DCs was excluded. The percentage of HIV-1 p24 expressing DCs in co-culture with apoptotic HIV-1 infected cells was 1–2% of the total number of DCs from nine different donors. DCs exposed to the cell free HIV-1 Ba-L isolate also expressed HIV-1 p24 protein at similar frequencies (1–2% of DCs) (FIG. 15e) while DCs co-cultured with apoptotic bodies from the non-infected T cell line HuT78 did not display any HIV-1 p24 specific staining (FIG. 15f). Flow cytometry analyses confirmed that the frequency of p24 expression in DCs co-cultured with apoptotic HuT78$_{SF2}$ cells did not differ from DCs exposed to the HIV-1 Ba-L isolate (data not shown).

Induction of proliferation by DCs after engulfment of apototic HIV-1 infected cells:

To investigate the ability of DCs to induce PBMC proliferation after ingestion of apoptotic bodies, the DCs were co-cultured with apoptotic HuT78$_{SF2}$ cells or apoptotic HuT78 cells or exposed to HIV-1 Ba-L isolate. Autologous PBMCs were subsequently added to these co-cultures and cell proliferation was measured by $^3$H-thymidine uptake. Different DCs: PBMC ratios and different DC-PBMC cultivation times were tested (FIG. 16a). An experimental design of 3–4×10$^4$ DCs and 1×10$^5$ PBMCs per well showed optimal proliferation responses after 6–7 days of culture. DCs exposed to HIV-1 Ba-L 6 days prior to addition of the PBMCs showed a significantly reduced proliferation compared to the DCs cultured in medium only (FIGS. 16b–c). In contrast, DCs co-cultured with apoptotic cells from both HuT78$_{SF2}$ and HuT78 for 6 days induced a significantly increased proliferation of PBMCs compared to DCs exposed to HIV-1 Ba-L or DCs cultured in medium only (p<0.05). The highest proliferation response was observed after priming the DCs with co-cultured apoptotic HuT78$_{SF2}$ bodies (FIGS. 16b–c). LPS was added to the culture medium to further differentiate DCs into more potent immunostimulatory cells (FIG. 16b). However, the addition of LPS did not significantly increase PBMC proliferation, neither did the variation in induced proliferation between the different co-cultures change in the presence or absence of LPS (FIGS. 16b–c), A mixture of HIV-1 Ba-L exposed DCs and DCs co-cultured with apoptotic HuT78$_{SF2}$ cells resulted in an inhibition of the proliferation otherwise induced by the DCs co-cultured with apoptotic HuT78$_{SF2}$ cells (p<0.05) (FIGS. 16a, d).

Induction of IFN-γ production in PBMCs after priming with co-cultured DCs:

The functional properties of the immune responses induced by DCs were further investigated by assessment of IFN-γ production in DC-PBMC co-cultures. The different DC cultures were incubated for 6 days prior to addition of PBMCs and then cultured for an additional 6 days before IFN-γ production was measured. The highest frequency of IFN-γ expressing cells, both when analyzed by in situ imaging (FIG. 17a) and by ELISA (FIG. 17b), was detected in cultures where DCs were fed with apoptotic HuT78$_{SF2}$ cells (p<0.05). The DCs co-cultured with apoptotic HuT78 cells or exposed to HIV-1 Ba-L showed comparable induction of IFN-γ production as DCs grown in medium only.

Ingestion of apoptotic bodies leads to increased MHC class II expression in DCs in the presence of LPS:

To determine whether apoptotic bodies could provide maturation signals to immature DCs, the expression of MHC class II and the co-stimulatory molecules CD86 and CD80 were investigated. Immature DCs from six out of six donors co-cultured with apoptotic cells, both from HuT78$_{SF2}$ and HuT78 cells in the presence of LPS, exhibited up-regulation of MHC class II compared to DCs co-cultured with medium only in six out of six donors (FIG. 18b). No difference in MHC class II expression was detected between DCs fed with apoptotic HuT78$_{SF2}$ or HuT78 cells (FIG. 18a). DCs cultured with the HIV-1 Ba-L isolate showed a similar or slightly higher MHC class II expression than DCs cultured in medium only (FIG. 18b). No significant alteration in the expression of the co-stimulatory molecules CD80 and CD86 was detected in the different co-cultures (data not shown). Furthermore DCs co-cultured with the apoptotic cells, HIV-1 Ba-L or medium only in the absence of LPS supplementation did not show any detectable changes in the expression of either MHC class II (FIGS. 18c–d), CD80 or CD86 (data not shown).

Discussion

Many investigators have used DC-based vaccines with various forms of antigen delivery to induce immunity. Potent anti-tumor responses have been observed using apoptotic bodies to deliver antigens to DCs. Uptake of apoptotic bodies and the presentation of viral antigens from influenza, CMV and EBV by DCs have furthermore been shown to induce immune responses in vitro. Targeting HIV-1 antigens to mature DCs using a canarypox virus as a vector, which also may involve presentation of apoptotic cells, were shown to elicit HIV-1 specific responses. Processing of ingested apoptotic material may result in delivery of antigen to the cytoplasm. This leads to degradation in the proteasomes as well as binding of peptides to MHC class I molecules via a TAP-dependent mechanism for subsequent peptide presentation on the cell surface in order to prime CD8' T cell responses. This alternative (exogenous) MHC class I pathway may be a physiological antigen presenting pathway and has been suggested to be obligatory to initiate innate CD8$^+$ T cell responses to viruses that infect non-haematopoetic cells. The present invention shows that EBV DNA and HIV-1 DNA may be transferred by uptake of apoptotic cells and result in transcription of genes as well as translation into proteins (see ex 1 and 2 above). These findings indicate that DNA derived from apoptotic cells is expressed and the corresponding proteins presented as antigens by the DCs.

In the present example it is shown that DC s express HIV-1 p24 protein after uptake of apoptotic bodies obtained from lymphoma cell lines with integrated HIV-1 (HuT78$_{SF2}$ and 8E5$_{LAV}$RT$^-$). Furthermore DCs fed with apoptotic HIV-1 infected or non-infected apoptotic cells showed increased MHC class II expression compared to DCs exposed to an HIV-1 Ba-L isolate or DCs grown in medium only. Delivering HIV-1 into DCs in vitro through uptake of apoptotic cells therefore provided a maturation signal to the DCs. It was however necessary to add an additional maturation stimulus such as LPS to detect increased MHC class II expression. In vivo the complex multi-step DC maturation process probably requires several interactions. Maturation can be accomplished by multiple stimuli such as, tumor necrosis factor-α (TNF-α), IL-1β, IFN-γ, LPS, CD40 Ligation or CpG oligonucleotides (Lore, K., A. Sonnerborg, J. Olsson, B. K. Patterson, T. E. Fehniger, L. Perbeck, and J. Andersson. 1999. HIV-1 exposed dendritic cells show increased pro-inflammatory cytokine production but reduced IL-1ra following lipopolysaccharide stimulation. *Aids* 13:2013; Caux, C., C. Massacrier, B. Vanbervliet, B. Dubois, C. Van Kooten, I. Durand, and J. Banchereau. 1994. Activation of Human Dendritic Cells through CD40 Crosslinking. *J Exp Med* 180:1263; Sallusto, F., M. Cella, C. Danieli, and A. Lanzavecchia. 1995. Dendritic cells use macropinocytosis and the mannose receptor to concentrate macromolecules in the major histocompatibility complex class II compartment, downregulation by cytokines and bacterial products. *J Exp Med* 182:389; Roake, J. A., A. S. Rao, P. J. Morris, C. P. Larsen, D. P. Hankins, and J. M. Austyn. 1995. Dendritic cell loss from nonlymphoid tissues after systemic administration of lipopolysaccharide, tumor necrosis factor, and interleukin 1. *J Exp Med* 181:2237; De Smedt, T., B. Pajak, E. Muraille, L. Lespagnard, E. Heinen, P. De Baetselier, J. Urbain, O. Leo, and M. Moser. 1996. Regulation of Dendritic Cell Numbers and Maturation by Lipopolysaccharide In Vivo. *J Exp Med* 184:1413; and Sparwasser, T., E. S. Koch, R. M. Vabulas, K. Heeg, C. B. Lipford, J. W. Ellwart, and H. Wagner. 1998. Bacterial DNA and immunostimulatory CpG oligonucleotides trigger maturation and activation of murine dendritic cells. *Eur J Immunol* 28:2045). Signals for maturation of DCs may be provided by cells that are virally infected or by other means are "stressed" or necrotic, but not by healthy cells or apoptotic cells (Gallucci, S., M. Lolkema, and P. Matzinger. 1999. Natural adjuvants: endogenous activators of dendritic cells. *Nat Med* 5:1249). This hypothesis is in line with the histological definition of apoptosis, which in contrast to necrosis does not include signs of inflammation in vivo. Here γ-irradiation has been used to induce apoptosis in T cell lymphoma cell lines. It cannot be excluded that γ-irradiation may induce as yet ill-defined adjuvant ("stress") effects. The heat shock proteins in these cell lines may furthermore have contributed to the maturation of the DCs (Tamura, Y., P. Peng, K. Liu, M. Daou, and P. K. Srivastava. 1997. Immunotherapy of tumors with autologous tumor-derived heat shock protein preparations. *Science* 278:117). The present findings therefore support a role for additional "danger" signals mediated for example by Toll-like receptor interactions, apart from virus infected apoptotic bodies, to accomplish terminal DC maturation (Sauter, B., M. L. Albert, L. Francisco, M. Larsson, S. Somersan, and N. Bhardwaj. 2000. Consequences of cell death: exposure to necrotic tumor cells, but not primary tissue cells or apoptotic cells, induces the maturation of immunostimulatory dendritic cells. *J Exp Med* 191:423).

Mature DCs but not immature DCs have been shown to generate vigorous immune responses after targeting with antigen (Engelmayer, J., M. Larsson, A. Lee, M. Lee, W. I. Cox, R. M. Steinman, and N. Bhardwaj. 2001. Mature Dendritic Cells Infected with Canarypox Virus Elicit Strong Anti-Human Immunodeficiency Virus CD8(+) and CD4(+) T-Cell Responses from Chronically Infected Individuals. *J Virol* 75:2142; Larsson, M., D. Messmer, S. Somersan, J. F, Fonteneau, S. M. Donahoe, M. Lee, P. R. Dunbar, V. Cerundolo, I. Julkunen, D. F. Nixon, and N. Bhardwaj. 2000. Requirement of mature dendritic cells for efficient activation of influenza A-specific memory CD8+ T cells. *J Immunol* 165:1182). Nevertheless, according to the present invention, DCs co-cultured with HIV- I infected or uninfected apoptotic allogeneic lymphoma T cells either with or without addition of LPS were capable of inducing autologous T cell proliferation in vitro. DCs incubated with cell free HIV-1 for more than 24 h have previously been shown to be unable to present antigen to T cells and to suppress the induction of T cell proliferation (Knight, S. C., S. Patterson, and S. E. Macatonia. 1991. Stimulatory and suppressive effects of infection of dendritic cells with HIV-1. *Immunol Lett* 30:213). In the present example it is shown that DCs co-cultured with apoptotic HIV-1 infected cells, subsequently expressed HIV-1 antigens and had the ability to induce T cell proliferation and IFN-γ production. The T cell proliferation observed in the present study was suppressed if the DCs co-cultured with apoptotic HIV-1 infected cells were mixed with DCs exposed to the cell free HIV-1 Ba-L virions prior to the addition of the PBMCs. This indicates that HIV-1 virions trapped by DCs are capable of inhibiting immune responses that are otherwise induced by DCs, presenting antigens that originate from apoptotic material. This could be one reason why antigen presentation of immunogenic "apoptotic material" may not occur efficiently in HIV-1 infection during high viral load. Induction of immune responses after immunization and improved responses to recall antigens can however be achieved when viral loads are kept in control by effective anti-retroviral treatment (Kroon, F. P., G. F. Rimmelzwaan, M. T. Roos, A. D. Osterhaus, D. Hamann, F. Miedema, and J. T. van Dissel. 1998. Restored humoral immune response to influenza vaccination in HIV-infected adults treated with highly active antiretroviral therapy. *Aids* 12:F217; Hel, Z., D. Venzon, M. Poudyal, W. P. Tsai, L. Giuliani, R. Woodward, C. Chougnet, G. Shearer, J. D. Altman, D. Watkins, N. Bischofberger, A. Abimiku, P. Markham, J. Tartaglia, and G. Franchini. 2000Viremia control following antiretroviral treatment and therapeutic immunization during primary SIV251 infection of macaques. *Nat Med* 6,1140; and Blazevic, V., N. Sahgal, H. A. Kessler, A. L. Landay, and G. M. Shearer. 2000. T cell responses to recall antigens, alloantigen, and mitogen of HIV-infected patients receiving long-term combined antiretroviral therapy. *AIDS Res Hum Retroviruses* 16:1887). The ability of DCs to prime T cells after internalization of apoptotic bodies has implications for vaccine development. As discussed above, such a vaccination strategy does not necessarily require the use of a vector. In one embodiment, administration of apoptotic bodies with integrated HIV-1 genes is sufficient to elicit an efficient immune response.

EXAMPLE 5: Induction of HIV-1 specific protective immunity in mice after vaccination with apoptotic HIV-1/MuLV pseudovirus infected syngenic cells Materials and methods Experimental procedures HIV-1 virus stock:

Amphotropic MuLV (A4070) in the CEM-1B cell line was used to prepare pseudovirus with the HIV-1 LAI strain as previously described (Andäng et al., 1999). The stock virus was titrated on human and murine cells as previously described (Hinkula et al, 01).

Preparation of apoptotic HIV-1/MuLV infected cells:

Spleen cells from C57BL/6 mice were infected in vitro as previously described. Virus infected stocks were quantified according to methods well known in the art and frozen in 10% DMSO until use. Cells were thawn and washed prior to g-irradiation (150 Gy).

Mice

10–12 weeks old C57BL/6 mice obtained from the Embryo and Genome Research core facility at Karolinska Institutet, Stockholm, Sweden, were kept at germ free pathogen-defined barrier conditions. The local animal research ethical committee approved of animal care and experimental procedures. Each experimental group contained 6 animals. Irradiated HIV-1/MuLV infected or uninfected cells were inoculated i.p. ($1\times10^6$ apoptotic cells/mouse). Two groups of mice were sacrified after one immunisation and the remaining mice received a boost immunisation after 3 weeks. Two additional groups of mice were sacrified after two immunisations. 3 weeks after the last immunisation two groups of mice were challenged with 100 000 TCID cell free HIV-1 pseudovirus i.p. in 1 ml PBS. The pseudovirus system was kindly provided by Drs. D. H.

and S. A. Spector at the University of California, San Diego, Calif. 10–12 days after challenge mice were sacrificed. Blood, spleen cells, peritoneal cells and fecal pellets were collected and analysed.

RESULTS EXAMPLE 5

Figure 19:
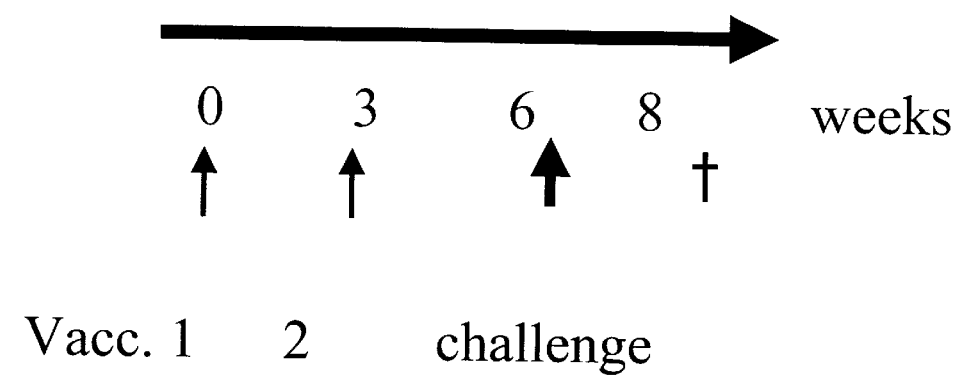
FIGS. 19A–B illustrates the experiment performed in example 5 of the present application. (A) shows the vaccination scheme for mice vaccinated with apoptotic MuLV-HIV infected syngenic cells while (B) shows the T-cell proliferation obtained.
Figure 19:
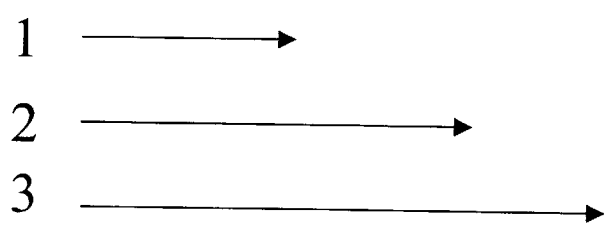
Figure 19:
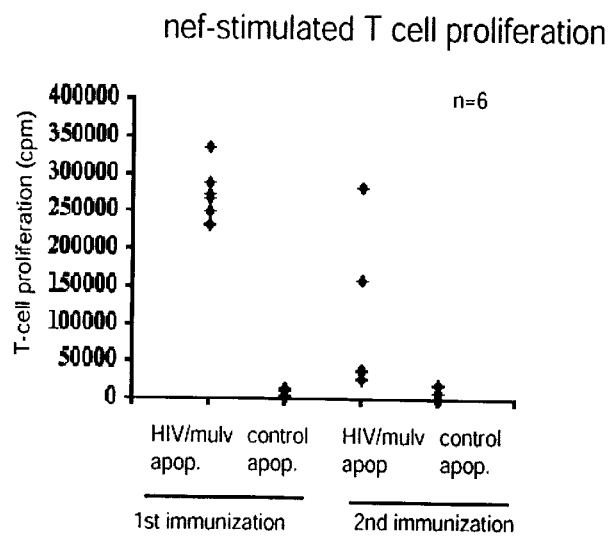

HIV-1 specific T cell responses induced after vaccination with apoptotic HIV-1/MuLV infected cells:

C57B1/6 mice (n=36) were immunized intraperitoneally (i.p.) with either apoptotic virus infected or apoptotic uninfected syngenic spleen cells. Three weeks later the first groups of mice were sacrificed (n=12) and the remaining mice received a booster vaccination with apoptotic cells. After additional three weeks, the second groups of mice were sacrificed (n=12) and the remaining mice (n=12) were challenged with pseudotype virus. Spleen cells from immunized mice were stimulated in vitro with ConA, p24, nef or a control protein and proliferation was measured by 3H-thymidine uptake, see FIG. 19. Mice inoculated with apoptotic HIV-1/MuLV infected spleen cells showed a strong induction of nef-specific lymphocyte proliferation (6 out of 6 mice) after the first vaccination, while mice inoculated with apoptotic uninfected cells (n=6) did not show any nef-induced proliferation (FIG. 19A). After receiving a prime and boost vaccination with apoptotic HIV-1/ MuLV infected spleen cells the nef-induced proliferation was lower compared to the response observed after only one inoculation. Mice immunized two times with apoptotic syngenic spleen cells did not show any nef-specific induction of lymphocyte proliferation, The spleen cells from the different groups were also stimulated with p24 or a control protein (FIG. 19B). P24-specific lymphocyte proliferation was induced after one inoculation with apoptotic HIV-1/MuLV infected spleen cells, but was more pronounced after a second boost. Mice inoculated with apoptotic control spleen cells did not show any p24specific lymphocyte proliferation.

Figure 20:
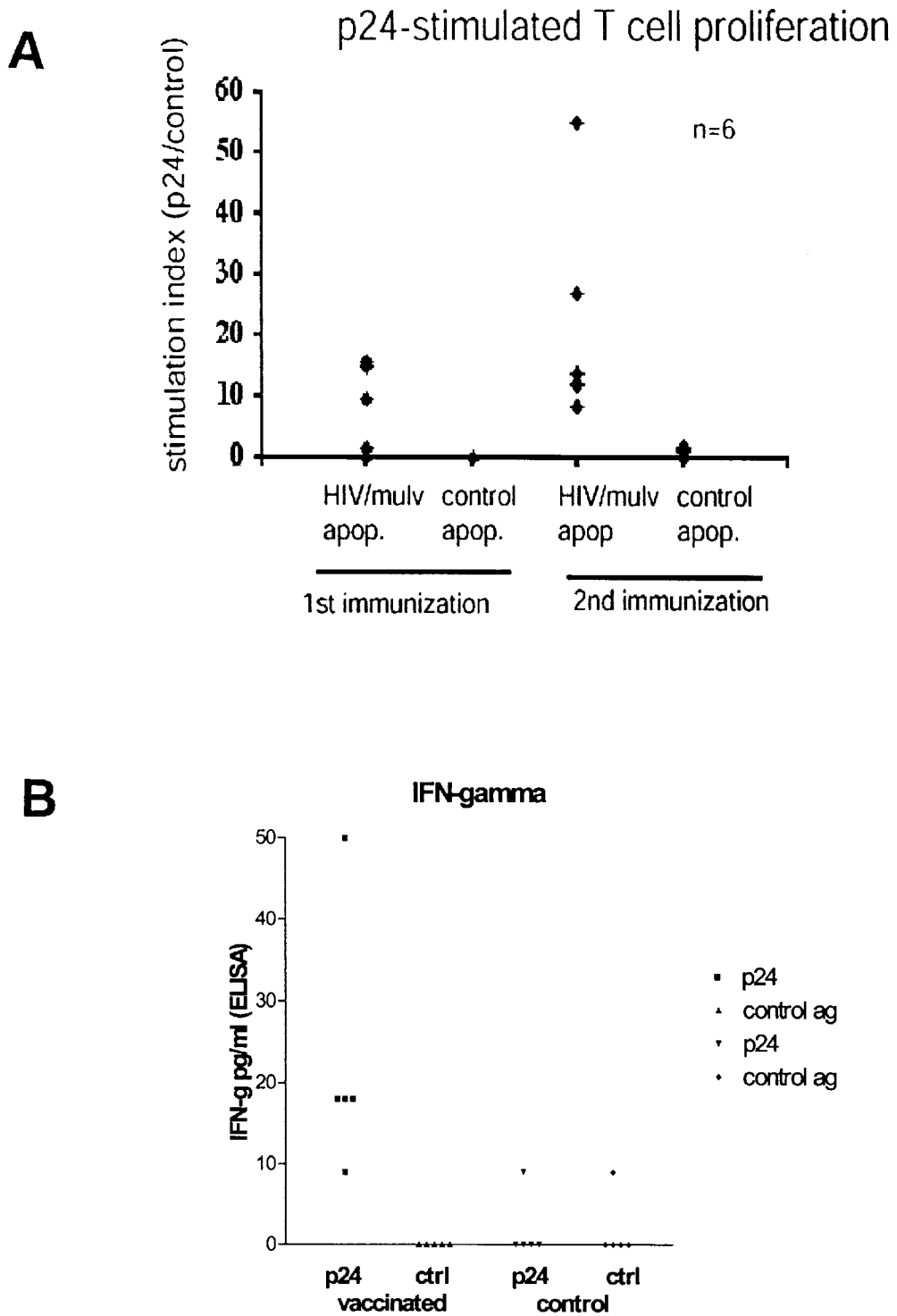
FIGS. 20A–B shows the stimulation index of MuLV-HIV infected cells as compared to control cells after a $1^{st}$ and a $2^{nd}$ immunization as obtained in accordance with example 5.

ELISA was used to detect presence of IFN-g, IL-2 and IL-4 in the tissue culture supernatants from the in vitro stimulated spleen cells (FIG. 20). Mice vaccinated with apoptotic HIV-1MuLV infected spleen cells showedp24 specific induction of IFN-$\gamma$ in 5 out of 5 mice analyzed. One mouse in the group vaccinated with apoptotic control cells showed induction of IFN-$\gamma$ in the supernatant but it was not p24 specific since stimulation with the control protein gave a similar induction of IFN-$\gamma$ (FIG. 20).

Figure 21:
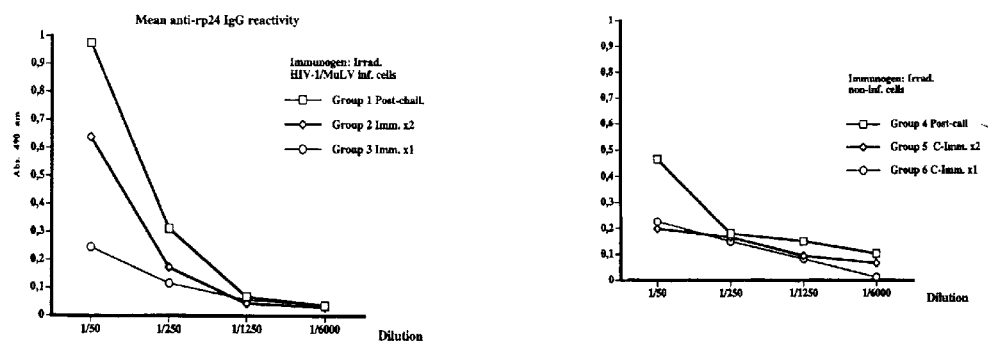
FIGS. 21A–B shows a quantification of the levels of anti-IIIV-1 specific antibodies in sera and faeces from mice immunized in accordance with example 5.
Figure 21:
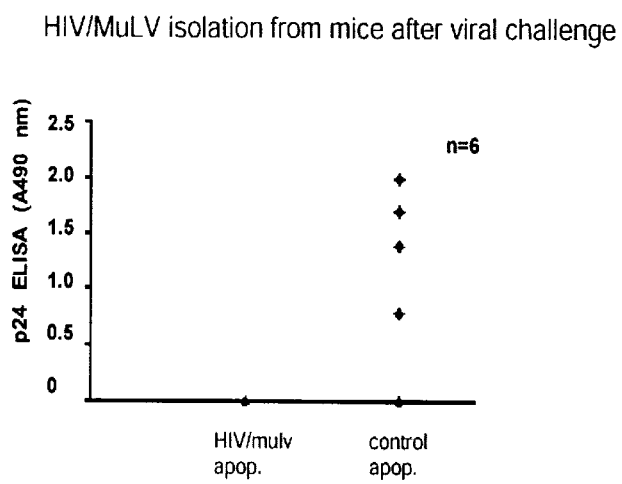

HIV-1 specific systemic and mucosal B cell responses induced after vaccination with apoptotic HIV-1 MuLV infected cells:

ELISA was used to quantify the levels of anti-HIV-1 (p24, rev, gp160, tat and nef) specific antibodies in sera and faeces from immunised mice (FIG. 21). Vaccination with apoptotic HIV-1/MuLV infected spleen cells resulted in a significant rise in levels of anti-HIV-1 specific antibodies, which was further boosted after challenge. Mice receiving apoptotic control cells showed a low induction of anti-HIV-1 antibodies only after challenge with pseudotype virus.

Mice vaccinated with apoptotic HIV-1/MuLV infected spleen cells are protected against challenge with HIV-1 /MuLV virus:

Mice vaccinated two times with either apoptotic HIV-1/MuLV infected spleen cells or apoptotic control cells were challenged i.p. with HIV-1/MuLV. Ten days later mice were sacrificed and the peritoneal cells were collected to attempt virus isolation as previously described (Hinkula, 01). Two of six mice vaccinated with apoptotic control cells showed positive virus isolation after 10 days and after 17 days in culture it was raised to 4 out of 6 mice. No virus could be isolated from mice vaccinated with apoptotic HIV-1/MuLV infected spleen cells (n=6).

What is claimed is:

1. A method of transferring genomic DNA from apoptotic bodies to engulfing cells, wherein DNA is transferred from a donor cell to a recipient cell, which method includes
    (a) providing somatic donor cells comprising genomic DNA;
    (b) generating apoptotic bodies of said donor cells;
    (c) incubation of the apoptotic bodies with engulfing recipient cells under biological conditions allowing uptake of DNA from the apoptotic bodies by said recipient cells; and, optionally,
    (d) selection of recipient cells which have integrated DNA from the apoptotic bodies.

2. A method according to claim 1, wherein the donor cell is selected from the group consisting of native or genetically modified blood cells, liver cells, bone marrow cells, tumor cells, and immortalized cell lines.

3. A method according to claim 1, wherein the engulfing cell is an antigen presenting cell.

4. A method according to claim 1, wherein the engulfing cell is selected from the group consisting of native or genetically modified macrophages, dendritic cells, endothelial cells and fibroblasts.

5. A method according to claim 1 for the generation of a pharmaceutical composition, which comprises a further step of admixture of recipient cells with a pharmaceutically acceptable carrier.

6. A method for the generation of a pharmaceutical composition, which comprises admixture of apoptotic bodies with a pharmaceutically acceptable carrier.

7. A method according to claim 1 for the identification of genes involved in pathological and/or biological processes.

8. A kit for performing a method according to claim 7, which comprises means for generating apoptotic bodies from donor cells; a compartment for coincubation of apoptotic bodies with recipient cells capable of engulfing DNA; a compartment for expression of protein products from recipient cell lines and means for identification of expression products.

9. A method of preventing and/or treating a clinical condition in a patient, which comprises
    (a) isolating donor cells comprising genomic DNA;
    (b) generating apoptotic bodies of said cells;
    (c) incubation of said apoptotic bodies with engulfing recipient cells under biological conditions allowing uptake of DNA from the apoptotic bodies by said recipient cells;
    (d) optionally a step for selection of recipient cells which have integrated DNA from the apoptotic bodies; and
    (e) administering of recipient cells in a pharmaceutically acceptable carrier to the patient, thus allowing a protective and/or therapeutic reaction against the clinical condition,
wherein the administered cells are capable of expression of protein product(s) encoded by the engulfed DNA in the patient.

10. A method according to claim 9, wherein the donor cell is selected from the group consisting of native or genetically modified blood cells, liver cells, bone marrow cells, tumor cells and immortalized cell lines.

11. A method according to claim 9, wherein the donor cell originates from the patient.

12. A method according to claim 9, wherein the engulfing cells are antigen presenting cells.

13. A method according to claim 9, wherein the engulfing cells are selected from the group consisting of native or genetically modified macrophages, dendritic cells, endothelial cells and fibroblasts.

14. A method according to claim 9, which is a vaccination against a pathogen.

15. A method according to claim 9, which is a method of inducing tolerance in an autoimmune disorder or a method of inducing tolerance against a transplant.

16. A method according to claim 9, which is a method of reconstituting absent or malfunctioning genes in the patient.

17. A method of preventing and/or treating a clinical condition in a patient, which comprises
 (a) isolating donor cells comprising genomic DNA;
 (b) generating apoptotic bodies of said cells;
 (c) administering of apoptotic bodies in a pharmaceutically acceptable carrier to the patient, thus allowing a protective and/or therapeutic reaction against the clinical condition,
wherein the apoptotic bodies are engulfed by recipient cells and thereby provides expression of protein product(s) encoded by said DNA in the patient.

18. A method according to claim 17, which is a vaccination against a pathogen.

19. A method according to claim 17, which is a method of inducing tolerance in an autoimmune disorder or a method of inducing tolerance against a transplant.

20. A method according to claim 17, which is a method of reconstituting absent or malfunctioning genes in the patient.

21. A method according to claim 14, in which the pathogen is a bacteria or a virus.

22. A method according to claim 21, which is a vaccination against human immunodeficiency virus.

23. A method according to claim 14, which is a vaccination against tumor growth.

24. A method according to claim 18, in which the pathogen is a bacteria or a virus.

25. A method according to claim 24, which is a vaccination against human immunodeficiency virus.

26. A method according to claim 18, which is a vaccination against tumor growth.

27. A method according to claim 15, which is a vaccination against an autoimmune disorder selected from the group consisting of rheumatoid arthritis, multiple sclerosis, systemic lupus erythematosus, diabetes, Crohn's syndrome and ulcerative colitis.

28. A method according to claim 15, which is a vaccination against autoimmune disorder selected from the group consisting of rheumatoid arthritis, multiple sclerosis, systemic lupus erythematosus, diabetes, Crohn'syndrome and ulcerative colitis.

* * * * *